United States Patent
Rothberg et al.

(10) Patent No.: US 10,605,730 B2
(45) Date of Patent: Mar. 31, 2020

(54) OPTICAL SOURCES FOR FLUORESCENT LIFETIME ANALYSIS

(71) Applicant: Quantum-Si Incorporated, Guilford, CT (US)

(72) Inventors: Jonathan M. Rothberg, Guilford, CT (US); Jason W. Sickler, Madison, CT (US); Lawrence C. West, San Jose, CA (US); Faisal R. Ahmad, Guilford, CT (US); Brendan Huang, South Pasadena, CA (US); Paul E. Glenn, Wellesley, MA (US); Jonathan C. Schultz, Guilford, CT (US); Jose Camara, Saratoga, CA (US)

(73) Assignee: Quantum-Si Incorporated, Guilford, CT (US)

( * ) Notice: Subject to any disclaimer, the term of this patent is extended or adjusted under 35 U.S.C. 154(b) by 751 days.

(21) Appl. No.: 15/161,067

(22) Filed: May 20, 2016

(65) Prior Publication Data
US 2016/0341664 A1     Nov. 24, 2016

Related U.S. Application Data

(63) Continuation-in-part of application No. 14/821,656, filed on Aug. 7, 2015, now Pat. No. 9,759,658.
(Continued)

(51) Int. Cl.
*H05B 33/08*     (2006.01)
*G01N 21/64*     (2006.01)
(Continued)

(52) U.S. Cl.
CPC ....... *G01N 21/6408* (2013.01); *G01N 21/645* (2013.01); *G01S 7/484* (2013.01);
(Continued)

(58) Field of Classification Search
CPC ............ G01N 21/6408; G01N 21/645; G01N 21/6458; G01N 2021/6439;
(Continued)

(56) References Cited

U.S. PATENT DOCUMENTS 4,295,226 A * 10/1981 Dombrowski ........... H03K 5/02
                                                      250/551
5,108,179 A     4/1992 Myers
(Continued)

FOREIGN PATENT DOCUMENTS

EP     0472318 A2     2/1992
EP     0542480 A2     5/1993
(Continued)

OTHER PUBLICATIONS

Araki, T., et al., "An ultraviolet nanosecond light pulse generator using a light emitting diode for test of photodetectors," Rev. Sci. Instr. vol. 68, 1365, Mar. 1997, pp. 1364-1368.
(Continued)

*Primary Examiner* — Jimmy T Vu
(74) *Attorney, Agent, or Firm* — Wolf, Greenfield & Sacks, P.C.

(57) ABSTRACT

Compact optical sources and methods for producing short and ultrashort optical pulses are described. A semiconductor laser or LED may be driven with a bipolar waveform to generate optical pulses with FWHM durations as short as approximately 85 ps having suppressed tail emission. The pulsed optical sources may be used for fluorescent lifetime analysis of biological samples and time-of-flight imaging, among other applications.

75 Claims, 20 Drawing Sheets

Related U.S. Application Data

(60) Provisional application No. 62/164,485, filed on May 20, 2015, provisional application No. 62/164,506, filed on May 20, 2015, provisional application No. 62/164,464, filed on May 20, 2015, provisional application No. 62/296,546, filed on Feb. 17, 2016, provisional application No. 62/310,398, filed on Mar. 18, 2016.

(51) Int. Cl.
| | |
|---|---|
| H01S 5/042 | (2006.01) |
| H01L 27/146 | (2006.01) |
| G01S 7/484 | (2006.01) |
| H05B 45/00 | (2020.01) |
| H05B 47/16 | (2020.01) |
| G01S 7/4863 | (2020.01) |

(52) U.S. Cl.
CPC ...... *H01L 27/14603* (2013.01); *H01S 5/0428* (2013.01); *H05B 45/00* (2020.01); *H05B 47/16* (2020.01); *G01N 21/6458* (2013.01); *G01N 2021/6439* (2013.01); *G01N 2021/6441* (2013.01); *G01N 2201/0612* (2013.01); *G01N 2201/0621* (2013.01); *G01N 2201/0697* (2013.01); *G01S 7/4863* (2013.01)

(58) Field of Classification Search
CPC ... G01N 2021/6441; G01N 2201/0612; G01N 2201/0621; G01N 2201/0697; G01S 7/4863; G01S 7/484; H01L 27/14603; H01S 5/0428; H05B 33/08; H05B 33/0842; H05B 37/02; H05B 37/0281
See application file for complete search history.

(56) References Cited

U.S. PATENT DOCUMENTS

| | | | |
|---|---|---|---|
| 5,471,515 | A | 11/1995 | Fossum et al. |
| 5,627,853 | A | 5/1997 | Mooradian et al. |
| 5,674,743 | A | 10/1997 | Ulmer |
| 5,822,472 | A | 10/1998 | Burkhard et al. |
| 6,355,420 | B1 | 3/2002 | Chan |
| 6,393,035 | B1 | 5/2002 | Weingarten et al. |
| 6,437,345 | B1 | 8/2002 | Bruno-Raimondi et al. |
| 6,716,394 | B2 | 4/2004 | Jensen et al. |
| 6,825,921 | B1 | 11/2004 | Modlin et al. |
| 6,834,064 | B1 | 12/2004 | Paschotta et al. |
| 7,052,847 | B2 | 5/2006 | Korlach et al. |
| 7,170,050 | B2 | 1/2007 | Turner et al. |
| 7,179,654 | B2 | 2/2007 | Verdonk et al. |
| 7,394,841 | B1 | 7/2008 | Konttinen et al. |
| 7,595,883 | B1 | 9/2009 | El Gamal et al. |
| 7,738,086 | B2 | 6/2010 | Shepard et al. |
| 7,820,983 | B2 | 10/2010 | Lundquist et al. |
| 7,873,085 | B2 | 1/2011 | Babushkin et al. |
| 7,968,702 | B2 | 6/2011 | Wegener et al. |
| 7,981,604 | B2 | 7/2011 | Quake |
| 8,274,040 | B2 | 9/2012 | Zhong et al. |
| 8,279,901 | B2 | 10/2012 | Karavitis |
| 8,465,699 | B2 | 6/2013 | Fehr et al. |
| 8,501,406 | B1 | 8/2013 | Gray et al. |
| 8,865,077 | B2 | 10/2014 | Chiou et al. |
| 9,318,867 | B2 | 4/2016 | Pronin et al. |
| 9,617,594 | B2 | 4/2017 | Rothberg et al. |
| 10,246,742 | B2 | 4/2019 | Rothberg et al. |
| 2003/0058904 | A1 | 3/2003 | Krainer et al. |
| 2003/0169784 | A1 | 9/2003 | Sutter et al. |
| 2003/0179786 | A1 | 9/2003 | Kopf |
| 2004/0047387 | A1 | 3/2004 | Bunting et al. |
| 2004/0169842 | A1 | 9/2004 | Dosluoglu et al. |
| 2004/0257140 | A1* | 12/2004 | Bergmann ............ G05F 3/265 327/304 |
| 2006/0029110 | A1* | 2/2006 | Cho ............ H01S 3/067 372/6 |
| 2006/0269190 | A1* | 11/2006 | Kim ............ G02B 6/12004 385/43 |
| 2008/0130099 | A1 | 6/2008 | Harter |
| 2009/0180500 | A1* | 7/2009 | Babushkin ............ H01S 5/042 372/30 |
| 2010/0021180 | A1* | 1/2010 | Uemura ............ H04B 10/801 398/183 |
| 2010/0173394 | A1 | 7/2010 | Colston et al. |
| 2010/0245354 | A1 | 9/2010 | Rousso et al. |
| 2010/0255487 | A1 | 10/2010 | Beechem et al. |
| 2011/0136201 | A1 | 6/2011 | Mao et al. |
| 2011/0165652 | A1 | 7/2011 | Hardin et al. |
| 2011/0206072 | A1 | 8/2011 | Karavitis |
| 2011/0236983 | A1 | 9/2011 | Beechem et al. |
| 2012/0081040 | A1 | 4/2012 | Ku |
| 2013/0071849 | A1 | 3/2013 | Kong et al. |
| 2014/0286364 | A1 | 9/2014 | Pronin et al. |
| 2015/0293021 | A1 | 10/2015 | Finkelstein et al. |
| 2016/0084761 | A1 | 3/2016 | Rothberg et al. |
| 2016/0336709 | A1 | 11/2016 | Manni |
| 2016/0344156 | A1 | 11/2016 | Rothberg et al. |
| 2016/0369332 | A1 | 12/2016 | Rothberg et al. |
| 2018/0115136 | A1 | 4/2018 | Delfyett et al. |
| 2018/0175582 | A1 | 6/2018 | Rothberg et al. |

FOREIGN PATENT DOCUMENTS

| | | |
|---|---|---|
| EP | 0601714 A1 | 6/1994 |
| EP | 1681356 A1 | 7/2006 |
| EP | 2182523 A1 | 5/2010 |
| JP | S63-17581 A | 1/1988 |
| WO | WO 02/11252 A2 | 2/2002 |
| WO | WO 2005/073407 A1 | 8/2005 |

OTHER PUBLICATIONS

Binh, P.H. et al., "A simple sub-nanosecond ultraviolet light pulse generator with high repetition rate and peak power," Rev. Sci. Instr. vol. 84, 083102 (2013), pp. 083102-1-083102-5.

Huang, R.K. et al., "Slab-coupled Optical Waveguide Lasers Emerge from a Multimode Sea," www.photonics.com, Oct. 2006, 15 pages.

Semiconductor Components Industries, LLC, "MC10EP05, MC100EP05. 3.3V / 5V ECL 2-Input Differential AND/NAND," Aug. 2008—Rev. 9, 11 pages.

International Search Report and Written Opinion for International Application No. PCT/US2017/066878 dated Mar. 15, 2018.

Champak et al., Ultrafast pulse generation in a mode-locked Erbium chip waveguide laser. Opt. Express 24. 2016. 8 pages.

Kwon et al., Ultrashort stretched-pulse L-band laser using carbon-nanotube saturable absorber. Opt. Express 23, 7779-7785. 2015.

International Search Report and Written Opinion for International Application No. PCT/US2016/033576 dated Nov. 4, 2016.

Invitation to Pay Additional Fees for International Application No. PCT/US2016/033585 dated Sep. 21, 2016.

International Search Report and Written Opinion for International Application No. PCT/US2016/033585 dated Nov. 11, 2016.

Huang et al., Gene expression analysis with an integrated CMOS microarray by time-resolved fluorescence detection. Biosensors and Bioelectronics. 2012;26(5):2660-5.

Lu et al., Terahertz Microchip for Illicit Drug Detection. IEEE Photonics Technology Letters. 2006;18(21):2254-6.

Sauer et al., Time-Resolved Identification of Individual Mononucleotide Molecules in Aqueous Solution with Pulsed Semiconductor Lasers. Bioimaging, Institute of Physics. 1998;6(1):14-24.

Uhring et al., A low-cost high-repetition-rate picosecond laser diode pulse generator. Optical Sensing II. 2004;5452:583-90.

Invitation to Pay Additional Fees for International Application No. PCT/US2016/033576 dated Aug. 24, 2016.

Pfeufer et al., A ddT ddA ddG ddC Length-sorted strands fow through a capillary Detector Final output Focused laser beam

(56) References Cited

OTHER PUBLICATIONS

Fluorescence Fluorescently teminated oligonucleotides Original DNA strand Genetics/DNA Sequencing. 2015;24-7.

* cited by examiner

OPTICAL SOURCES FOR FLUORESCENT LIFETIME ANALYSIS

CROSS-REFERENCE TO RELATED APPLICATIONS

This application claims priority to U.S. provisional application No. 62/164,485 titled, "Pulsed Laser" filed on May 20, 2015, U.S. provisional application No. 62/164,506 titled, "Integrated Device For Temporal Binning of Received Photons" filed on May 20, 2015, U.S. provisional application No. 62/164,464 titled, "Integrated Device With External Light Source for Probing Detecting and Analyzing Molecules", filed on May 20, 2015, to U.S. provisional application No. 62/296,546, filed Feb. 17, 2016, titled "Sensor and Device for Lifetime Imaging and Detection Applications," and to U.S. provisional application No. 62/310,398 titled, "Pulsed Laser and System" filed on Mar. 18, 2016. This application is a continuation-in-part of U.S. application Ser. No. 14/821,656, filed Aug. 7, 2015, titled "Integrated Device for Temporal Binning of Received Photons." Each of the foregoing applications is hereby incorporated by reference in its entirety. This application also claims priority to U.S. provisional application No. 62/164,506 titled, "Integrated Device For Temporal Binning of Received Photons" filed on May 20, 2015 and to U.S. provisional application No. 62/164,464 titled, "Integrated Device With External Light Source for Probing Detecting and Analyzing Molecules, filed on May 20, 2015.

FIELD

The present application is directed to devices and methods for producing short and ultrashort optical pulses for time-domain applications that include fluorescent lifetime and time-of-flight applications.

BACKGROUND

Ultrashort optical pulses (i.e., optical pulses less than about 100 picoseconds) are useful in various areas of research and development as well as commercial applications involving time-domain analyses. For example, ultrashort optical pulses may be useful for time-domain spectroscopy, optical ranging, time-domain imaging (TDI), and optical coherence tomography (OCT). Ultrashort-pulses may also be useful for commercial applications including optical communication systems, medical applications, and testing of optoelectronic devices and materials.

Conventional mode-locked lasers have been developed to produce ultrashort optical pulses, and a variety of such lasers are currently available commercially. For example, some solid-state lasers and fiber lasers have been developed to deliver pulses with durations well below 200 femtoseconds. However, for some applications, these pulse durations may be shorter than is needed to obtain useful results, and the cost of these lasing systems may be prohibitively high. Additionally, these lasing systems may be stand-alone systems that have a sizeable footprint (e.g., on the order of 1 ft$^2$ or larger) and appreciable weight, and may not be readily portable. Such lasing systems and their driving electronics may be difficult to incorporate into an instrument as a replaceable module, or even be incapable of being incorporated into a hand-held device. As a result, ultra-short pulsed lasers are often manufactured as a separate stand-alone instrument from which an output beam may be coupled to another instrument for a particular application.

SUMMARY

The technology described herein relates to apparatus and methods for producing short and ultrashort optical pulses with laser diodes (LDs) or light-emitting diodes (LEDs). Short pulses are pulses having full-width-half-maximum (FWHM) temporal profiles between about 100 picoseconds and about 10 nanoseconds. Ultrashort pulses are pulses having FWHM temporal profiles less than about 100 picoseconds. Gain-switching techniques and related circuitry are described that may be implemented in compact, low-cost laser systems to produce pulses having durations less than about 2 nanoseconds in some embodiments, and less that about 100-picosecond in some cases. The inventors have recognized and appreciated that a compact, low-cost, pulsed-laser system may be incorporated into instrumentation (e.g., fluorescent lifetime imaging devices, bioanalytical instruments that utilize lifetime-resolved fluorescent detection, time-of-flight instruments, optical coherence tomography instruments) that may allow such instrumentation to become easily portable and produced at appreciably lower cost than is possible for such systems that use conventional ultrashort-pulsed laser systems. High portability may make such instruments more useful for research, development, clinical, commercial, and in-home applications.

Some embodiments relate to a pulsed optical source comprising a semiconductor diode configured to emit light, and a driving circuit that includes a transistor coupled to a terminal of the semiconductor diode, wherein the driving circuit is configured to receive a unipolar pulse and apply a bipolar electrical pulse to the semiconductor diode responsive to receiving the unipolar pulse.

Some embodiments relate to methods of producing an optical pulse. A method may comprise acts of receiving at least one clock signal, producing an electrical pulse from the at least one clock signal, driving a gate terminal of a transistor with the electrical pulse, wherein a current carrying terminal of the transistor is connected to a semiconductor diode that is configured to emit light, and applying a bipolar current pulse to the semiconductor diode to produce an optical pulse responsive to activation of the transistor by the electrical pulse.

Some embodiments relate to a fluorescent lifetime analysis system comprising a semiconductor diode configured to emit light, a driving circuit configured to apply a bipolar current pulse to the semiconductor diode to produce an optical pulse, an optical system arranged to deliver the optical pulse to a sample, and a photodetector configured to discriminate photon arrival times into at least two time bins during a single charge-accumulation interval of the photodetector.

Some embodiments relate to a pulsed optical source comprising, a semiconductor diode configured to emit light, a first logic gate configured to form a first pulse at an output of the first logic gate, and a driving circuit coupled to the first logic gate, wherein the driving circuit is configured to receive the first pulse and apply a bipolar electrical pulse to the semiconductor diode to produce an optical pulse responsive to receiving the first pulse.

Some embodiments relate to a pulsed optical source comprising a semiconductor diode configured to emit light, and a driving circuit that includes a transistor coupled to a terminal of the semiconductor diode, wherein the driving circuit is configured to receive a unipolar pulse and apply a bipolar electrical pulse to the semiconductor diode responsive to receiving the unipolar pulse, wherein the transistor is connected in parallel with the semiconductor diode between a current source and a reference potential.

Some embodiments relate to a pulsed optical source comprising a semiconductor diode configured to emit light, and plural first circuit branches connected to a first terminal of the semiconductor diode, each circuit branch comprising a transistor having its current-carrying terminals connected between a reference potential and the first terminal of the semiconductor diode.

Some embodiments relate to a pulsed optical source comprising a radio-frequency amplifier providing a signal and an inverted signal, a logic gate configured to receive the signal and a phase-shifted inverted signal and output a pulse and an inverted pulse, a combiner configured to combine the pulse and inverted pulse onto a common output, and a semiconductor diode coupled to the common output and configured to produce an optical pulse responsive to receiving the pulse and inverted pulse.

Some embodiments relate to a pulsed optical source comprising a radio-frequency logic gate configured to receive a first signal and an inverted version of the first signal and output a pulse and an inverted version of the pulse, and a semiconductor diode connect to the radio-frequency logic gate and arranged to receive the pulse at a first terminal of the semiconductor diode and the inverted version of the pulse at a second terminal of the semiconductor diode and emit an optical pulse.

The foregoing and other aspects, implementations, acts, functionalities, features and, embodiments of the present teachings can be more fully understood from the following description in conjunction with the accompanying drawings.

BRIEF DESCRIPTION OF THE DRAWINGS

The skilled artisan will understand that the figures, described herein, are for illustration purposes only. It is to be understood that in some instances various aspects of the invention may be shown exaggerated or enlarged to facilitate an understanding of the invention. In the drawings, like reference characters generally refer to like features, functionally similar and/or structurally similar elements throughout the various figures. The drawings are not necessarily to scale, emphasis instead being placed upon illustrating the principles of the teachings. The drawings are not intended to limit the scope of the present teachings in any way.

FIG. 1-2 depicts a train of ultrashort optical pulses, according to some embodiments.

FIG. 2-1A illustrates optical pump and output pulses for gain switching, according to some embodiments.

FIG. 2-1B illustrates relaxation oscillations, according to some embodiments.

FIG. 2-1C depicts an optical output pulse showing a tail, according to some embodiments.

FIG. 2-2A depicts a pulsed semiconductor laser diode, according to some embodiments.

FIG. 2-2B depicts a pulser circuit schematic for pulsing a laser diode or light-emitting diode, according to one embodiment.

FIG. 2-2C illustrates improvements in current delivered to a laser diode, according to some embodiments.

FIG. 2-3 depicts a current drive waveform for gain-switching a laser diode, according to some embodiments.

FIG. 2-4A depicts a pulser circuit for driving a laser diode or light-emitting diode, in some embodiments.

FIG. 2-4B depicts a pulser circuit schematic for driving a laser diode or light-emitting diode, according to some embodiments.

FIG. 2-4C depicts a pulser circuit schematic for driving a laser diode or light-emitting diode, according to some embodiments.

FIG. 2-4D depicts an RF driver for pulsing a laser diode or light-emitting diode, according to some embodiments.

FIG. 2-4E illustrates a drive waveform produced by the circuit of FIG. 2-4D, according to some embodiments.

FIG. 2-4F depicts an RF driver for pulsing a laser diode or light-emitting diode, according to some embodiments.

FIG. 2-4G illustrates drive waveforms produced by the circuit of FIG. 2-4F, according to some embodiments.

FIG. 2-4H depicts a pulser circuit schematic for driving a laser diode or light-emitting diode, according to some embodiments.

FIG. 2-4I illustrates efficiency of power coupling to a laser diode, according to some embodiments.

FIG. 2-4J depicts a pulser and driver circuit for pulsing optical emission from a laser diode or light-emitting diode, according to some embodiments.

FIG. 2-4K depicts a pulser circuit for producing a train of pulses, according to some embodiments.

FIG. 2-4L illustrates data inputs to a logic gate in a pulser circuit, according to some embodiments.

FIG. 2-4M depicts a driver circuit for driving a laser diode or light-emitting diode with electrical pulses, according to some embodiments.

FIG. 2-5A depicts a pulser circuit for gain-switching a laser diode, according to some embodiments.

FIG. 2-5B illustrates a drive voltage from a pulser circuit, according to some embodiments.

FIG. 2-5C and FIG. 2-5D illustrate example measurements of ultrafast optical pulses produced from a gain-switched laser diode, according to some embodiments.

FIG. 2-6A depicts a slab-coupled optical waveguide semiconductor laser that may be gain-switched or Q-switched, according to some embodiments.

FIG. 2-6B illustrates an optical mode profile in a slab-coupled optical waveguide laser, according to some embodiments.

FIG. 2-6C depicts an integrated, gain-switched semiconductor laser and coupled saturable absorber, according to some embodiments.

FIG. 3-1 depicts a system for synchronizing timing of optical pulses to instrument electronics, according to some embodiments.

FIG. 3-2 depicts a system for synchronizing timing of optical pulses to instrument electronics, according to some embodiments.

FIG. 3-3 depicts a system for synchronizing timing of optical pulses from two pulse sources to instrument electronics, according to some embodiments.

FIG. 3-4A depicts a system for synchronizing interleaved timing of optical pulses from two pulse sources to instrument electronics, according to some embodiments.

FIG. 3-4B depicts interleaved and synchronized pulse trains from two pulsed optical sources, according to some embodiments.

FIG. 4-1 depicts an instrument for analyzing fluorescent lifetimes of a sample, according to some embodiments.

FIG. 4-2 depicts emission probabilities for fluorescent molecules having different emission lifetimes.

FIG. 4-3 depicts time-binned detection of fluorescent emission from fluorescent molecules.

FIG. 4-4 depicts a time-binning photodetector, according to some embodiments.

FIG. 4-5A depicts multiple excitation pulses followed by fluorescent emission and corresponding binned signals, according to some embodiments.

FIG. 4-5B depicts a histogram produced from binned signals for a particular fluorophore, according to some embodiments.

The features and advantages of the present invention will become more apparent from the detailed description set forth below when taken in conjunction with the drawings. When describing embodiments in reference to the drawings, directional references ("above," "below," "top," "bottom," "left," "right," "horizontal," "vertical," etc.) may be used. Such references are intended merely as an aid to the reader viewing the drawings in a normal orientation. These directional references are not intended to describe a preferred or only orientation of an embodied device. A device may be embodied in other orientations.

DETAILED DESCRIPTION

I. Introduction

The inventors have recognized and appreciated that conventional ultrashort-pulsed optical sources with pulse repetition rates below 1 GHz are typically large, expensive, and unsuitable for many mobile applications. For example, conventional ultrashort-pulsed lasers may not be incorporated into compact and portable instrumentation. The inventors have recognized and appreciated that a small, short or ultrashort-pulsed optical source can enable new and useful devices for a wide range of time-domain applications. Such applications include, but are not limited to time-of-flight imaging, ranging, fluorescent and fluorescent lifetime analyses, biological or chemical analyses, optical coherence tomography (OCT), and medical point-of-care (POC) instrumentation. In some cases, POC instrumentation may comprise apparatus for detecting fluorescence from a biological sample, and analyzing the fluorescence to determine a property of the biological sample. A pulsed optical source may be used to excite fluorescence in such instrumentation. The inventors have conceived of compact, short and ultrashort-pulsed optical sources and systems that can produce optical pulses at various wavelengths having pulse durations below about 2 nanoseconds, and even less than 100 picoseconds, according to some embodiments.

Figure 1:
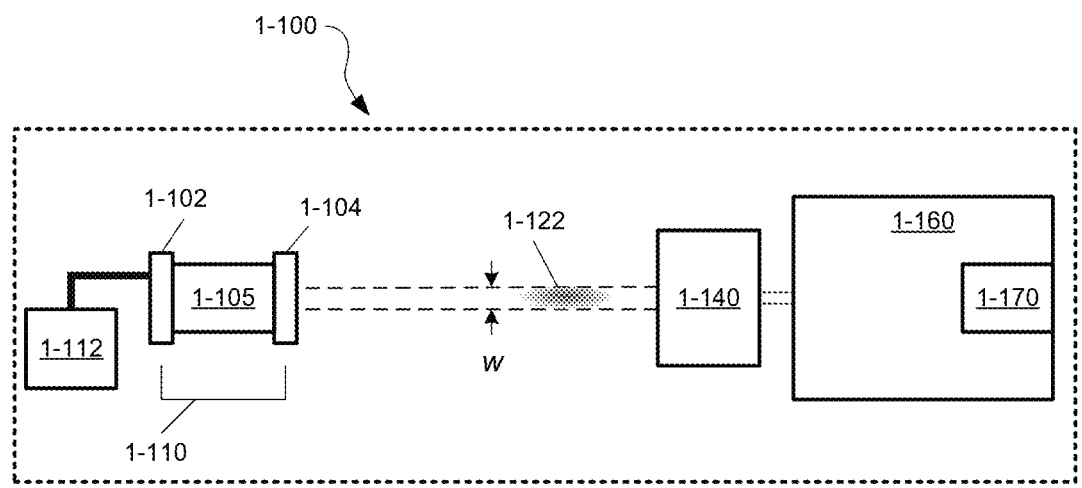
FIG. 1-1 depicts a pulsed lasing system incorporated with an analytical instrument, according to some embodiments.

In overview, FIG. 1-1 depicts a pulsed optical source 1-110 that may be incorporated into an analytical instrument 1-100, such as a POC or OCT instrument that excites and detects fluorescence or a time-of-flight imaging instrument. The instrument may include an optical system 1-140 and an analytic system 1-160. The optical system 1-140 may include one or more optical components (e.g., lens, mirror, optical filter, attenuator) and be configured to operate on and/or deliver optical pulses from the optical source 1-110 to the analytic system 1-160. The analytic system may include one or more components (e.g., lens, mirror, optical filter, attenuator, photodetector) arranged to receive an optical signal (e.g., fluorescence, backscattered radiation) from a sample 1-170 to be analyzed and produce an electrical signal representative of the received optical signal. In some embodiments, the analytic system 1-160 may further include electronics configured to process the electrical signal.

According to some embodiments, the pulsed optical source 1-110 may comprise at least one laser diode (LD) that is gain switched. In some embodiments, the pulsed optical source 1-110 may comprise at least one light-emitting diode (LED) that is driven with short current pulses. A pulser circuit 1-112 that generates nanosecond-scale, or shorter, current pulses may be included with an analytical instrument 1-100 to drive the optical source 1-110.

When configured as a laser diode, a pulsed optical source 1-110 may comprise a gain medium 1-105 (e.g., any suitable semiconductor junction which may or may not include multiple quantum wells), and at least two cavity mirrors 1-102, 1-104 (or reflective facets of a laser diode) that define ends of an optical laser cavity. In some embodiments, there may be one or more additional optical elements in the laser cavity for purposes of beam shaping, polarization control, wavelength selection, and/or pulse forming. Light-collecting optics may be included with a laser diode, and configured to concentrate emission from the laser diode into a beam. The beam from a laser diode may or may not be collimated by the light-collecting optics. When the laser operates in gain-switched mode, an optical pulse may build up within the laser cavity between the cavity's end mirrors 1-102, 1-104 responsive to the application of a current pulse through the laser's diode junction. One of the cavity mirrors 1-104 (often referred to as an output coupler) may partially transmit a portion of the pulse, so that an optical pulse 1-122 is emitted from the pulsed laser 1-110. When current driving pulses are repeatedly applied to the laser diode, a train of pulses 1-122 (only one shown) may be emitted from the laser cavity in rapid succession. This train of pulses may be referred to as a laser beam that can be characterized by a beam waist w. The laser beam may be collimated (indicated by the parallel dashed lines), partially-collimated, or may not be collimated. The beam waist represents a transverse dimension of the emitted laser beam (e.g., $\pm 1/e^2$ values of the transverse intensity profile for a Gaussian beam or a full-width-half-maximum (FWHM) value for other transverse intensity beam profiles), and may change in value with distance from the output coupler. The beam collimation and waist may depend upon the laser's cavity geometry and optical properties and whether any optical elements (e.g., collimating lenses) are included with the laser cavity.

When configured as a light-emitting diode, a pulsed optical source 1-110 may comprise any suitable semiconductor junction that is configured to emit incoherent or partially coherent light. Light-collecting optics may be included and arranged to concentrate emission from the LED into an output beam. The beam from an LED may or may not be collimated by the light-collecting optics. When operating, an LED generates an optical pulse of mainly spontaneously emitted photons responsive to the application of a current pulse across the LED junction, though some stimulated emission may be present in the output as amplified spontaneous emission. Typically, a spectral bandwidth emitted from an LED is on the order of 10's of nanometers, whereas a spectral bandwidth emitted from an LD may be less than two nanometers.

A characteristic wavelength emitted from an LD or LED may be selected by a choice of semiconductor materials and/or impurities added to the semiconductor materials. Indium-phosphide-based semiconductors and alloys thereof may be used for longer wavelengths in the red and infrared regions of the spectrum. Gallium-arsenide-phosphide-based semiconductors and alloys thereof may be used for shorter wavelengths into the yellow region of the spectrum. Aluminum-gallium-phosphide or gallium-nitride and their alloys may be used for the green and blue regions of the spectrum.

According to some embodiments, a particular semiconductor material may be selected for a pulsed optical source 1-110 of an instrument that excites and detects fluorescence (e.g., a POC fluorescent lifetime imaging instrument) to produce pulses having one or more of the following characteristic wavelengths: 270 nm, 280 nm, 325 nm, 340 nm, 370 nm, 380 nm, 400 nm, 405 nm, 410 nm, 450 nm, 465 nm, 470 nm, 490 nm, 515 nm, 640 nm, 665 nm, 808 nm, and 980 nm. In some implementations, a semiconductor may be selected for a pulsed optical source 1-110 of an instrument to produce pulses having a range or spectral distribution of wavelengths falling within one of the following ranges of wavelengths: approximately 270 nm to approximately 370 nm, approximately 340 nm to approximately 400 nm, approximately 380 nm to approximately 490 nm, and approximately 410 nm to approximately 470 nm.

For reference, the phrase "characteristic wavelength" or "wavelength" may refer to a central or predominant wavelength within a limited bandwidth of radiation. In some cases, it may refer to a peak wavelength within a bandwidth of radiation. The phrase "characteristic energy" or "energy" may refer to an energy associated with a characteristic wavelength. The term "optical" may refer to ultraviolet, visible, near infrared, and short-wavelength infrared spectral bands.

In some embodiments, an optical system 1-140 may operate on a beam of pulses 1-122 emitted from the pulsed optical source 1-110. For example, the optical system may include one or more lenses to reshape the beam and/or change the divergence of the beam. Reshaping of the beam may include increasing or decreasing the value of the beam waist and/or changing a cross-sectional shape of the beam (e.g., elliptical to circular, circular to elliptical, etc.). Changing the divergence of the beam may comprise increasing or decreasing the beam's divergence. In some implementations, the optical system 1-140 may include an attenuator or optical amplifier to change the amount of beam energy. In some cases, the optical system may include wavelength filtering elements. In some implementations, the optical system may include pulse shaping elements, e.g., a pulse stretcher and/or pulse compressor. In some embodiments, the optical system may include one or more nonlinear optical elements, such as a saturable absorber for reducing a pulse length or a nonlinear crystal for converting the pulse wavelength to a shorter wavelength via frequency doubling or a longer wavelength via parametric amplification. According to some embodiments, the optical system 1-140 may include one or more elements that alter, select, and/or control the polarization of the pulses from the optical source 1-110.

Although the pulsed optical source 1-110 and optical system 1-140 are shown as separate elements from the analytic system 1-160 in FIG. 1-1, the pulsed optical source and optical system may be manufactured as a compact and replaceable module that can be housed within the analytic system 1-160, according to some embodiments. In some embodiments, the pulser circuit 1-112 and pulsed optical source 1-110 may be integrated onto a same board (e.g., a same printed circuit board) or a same substrate (e.g., a same semiconductor substrate).

Figures 1, 2:
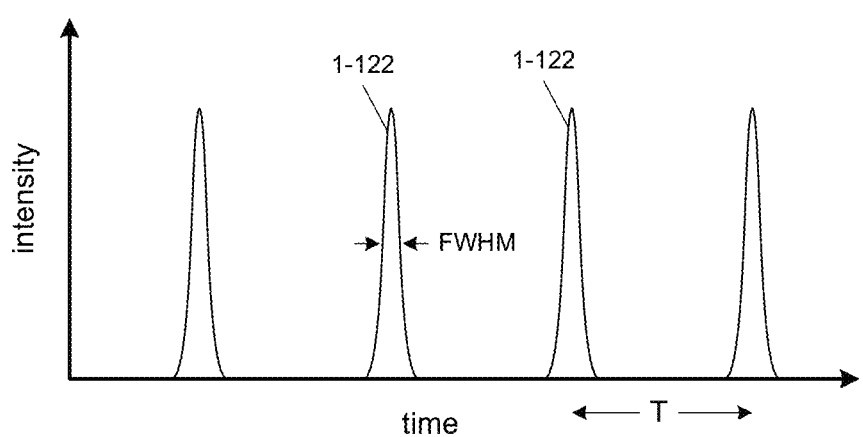

In various embodiments, pulses 1-122 emitted from a pulsed optical source may have temporal intensity profiles as depicted in FIG. 1-2. In some embodiments, the peak intensity values of the emitted pulses may be approximately equal, and the profiles may have a Gaussian temporal profile, though other profiles such as a $sech^2$ profile may be possible. In some cases, the pulses may not have symmetric temporal profiles and may have other temporal shapes. In some embodiments, gain and/or loss dynamics within the optical source 1-110 may yield pulses having asymmetric profiles, as described below in connection with FIG. 2-1C. The duration of each pulse may be characterized by a full-width-half-maximum (FWHM) value, as indicated in FIG. 1-2. Ultrashort optical pulses may have FWHM values less than 100 picoseconds. Short optical pulses may have FWHM values less than approximately 10 nanoseconds.

The pulses emitted from an optical source 1-110 may be spaced in time by regular intervals T, sometimes referred to as the pulse-separation interval. In some embodiments, T may be determined by active gain and/or loss modulation rates in a laser. For example, the repetition rate at which a laser diode is gain-switched or current applied to the junction of a light-emitting diode may determine the pulse-separation interval T. According to some embodiments, the pulse-separation interval T may be between about 1 ns and about 100 ns. In some implementations, the pulse-separation interval T may be long, for example, to repeat at a frame rate of an imaging device. In some cases, the pulse-separation interval T may be between about 100 ns and about 50 ms.

The transverse spatial profile of pulses 1-122 may be single-mode Gaussian in some embodiments, however the invention is not limited to such profiles. In some implementations, the transverse spatial profile of pulses 1-122 may be multi-modal, e.g., having multiple distinct intensity peaks. For a multi-mode source, the optical system 1-140 may include diffusion optics that homogenize the pulses' transverse intensity profile. By allowing use of a multi-mode source, higher pulse energies may be obtained from a laser diode. For example, the laser diode's active region can be enlarged in a direction transverse to the laser's optical axis to increase its optical output.

When used to excite fluorescence, pulses 1-122 from a pulsed optical source may be referred to as "excitation pulses."

The term "fluorescent molecules" may be used to refer fluorescent tags, fluorescent markers that may be attached to molecular probes, fluorophores, and autofluorescent molecules. The term "fluorescence" may be used to refer to light emitted from fluorescent tags, fluorescent markers that may be attached to molecular probes, fluorophores, and autofluorescent molecules.

II. Pulsed Optical Sources

The inventors have conceived of pulser circuits and techniques for producing short and ultrashort optical pulses from laser diodes and light-emitting diodes. The pulsing circuits and techniques have been employed, in some implementations, to gain-switch semiconductor lasers and produce a train of ~85 picosecond (ps) pulses (FWHM) having peak powers of approximately 1 W at repetition rates of up to 100 MHz (T as short as 10 nanoseconds). In some embodiments, a unipolar or bipolar current waveform may be produced by a pulser circuit and used to drive a laser diode's gain medium in a manner to excite optical pulses and suppress emission at the tails of the pulses. In some embodiments, a unipolar or bipolar current waveform may be produced by a pulser circuit and may be used to drive one or more light-emitting diodes to output short or ultrashort optical pulses.

Figures 1A, 2:
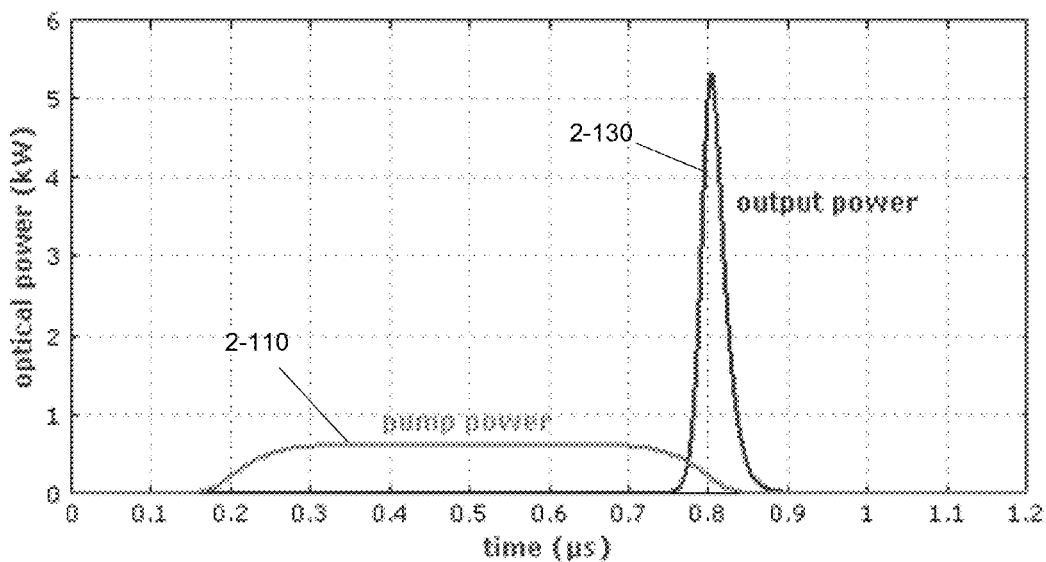
Figures 1B, 2:
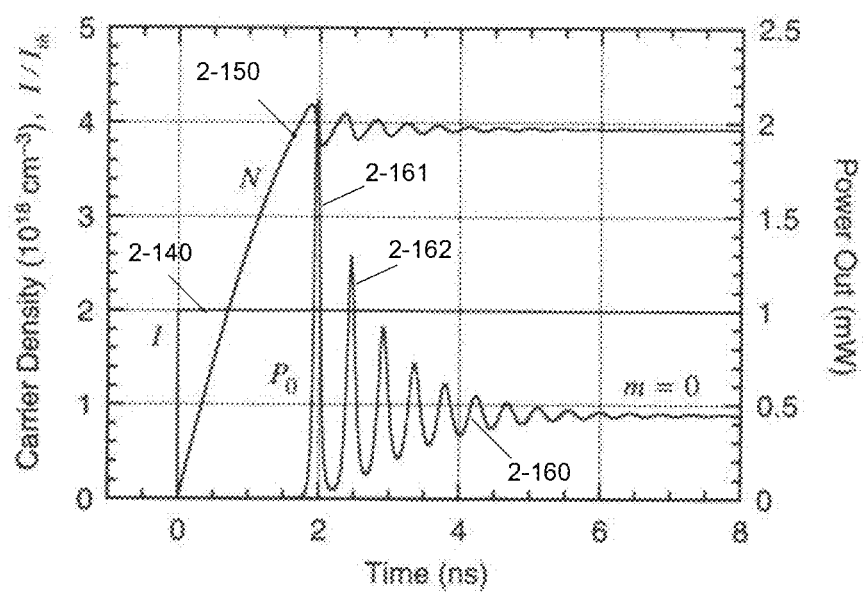
Figures 1C, 2:
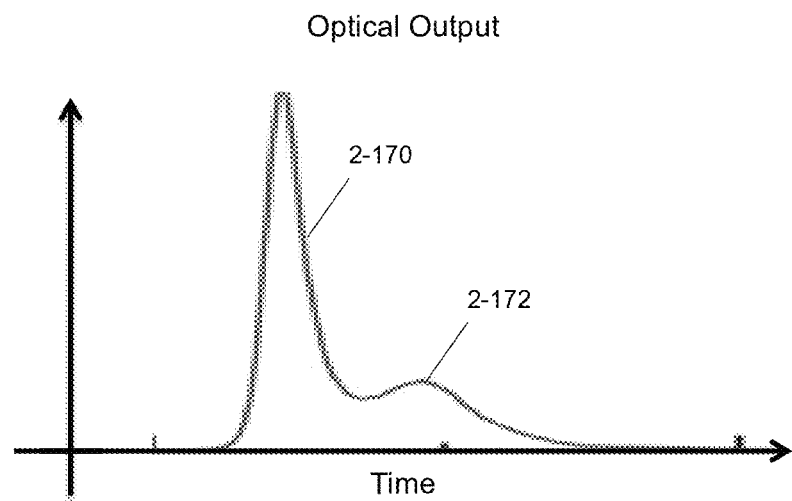

For purposes of describing gain switching in laser diodes, FIGS. 2-1A through 2-1C are included to illustrate laser dynamics associated with gain switching. FIG. 2-1A illustrates a pump-power curve 2-110 that is representative of pump power applied to a gain medium of a gain-switched laser, according to some embodiments. As depicted, the pump power may be applied for a brief duration (depicted as approximately 0.6 microseconds) to the gain medium in a laser cavity. For a semiconductor laser diode, application of pump power may comprise applying a bias current across a p-n junction or multiple quantum wells (MQWs) of the laser diode. The pump power pulse may be applied repetitively at regularly-spaced time intervals, for example, at a pulse-separation interval or pulse repetition time T.

During application of the pump power pulse, optical gain in the laser cavity increases until the gain begins to exceed optical losses in the cavity. After this point, the laser may begin to lase (i.e., amplify photons passing through the gain medium by the process of stimulated emission). The amplification process results in a rapid increase in laser light and depletion of excited states in the gain medium to produce at least one output pulse 2-130 as depicted. In some embodiments, the pump power pulse 2-110 is timed to turn off at approximately the same time that the peak of the output pulse occurs. Turning off the pump power pulse terminates further lasing, so that the output pulse 2-130 quenches. In some embodiments, the output pulse 2-130 may have a shorter duration than the pump pulse 2-110, as depicted in the drawing. For example, an output pulse 2-130 produced by gain switching may be less than ⅕ the duration of the pump pulse 2-110.

If the pump power pulse is not turned off, then the dynamics depicted in FIG. 2-1B may occur. In this case, the pump power curve (shown as pump current density) 2-140, depicted as a step function, represents current density applied to a semiconductor laser. The graph shows that the gain medium is excited by a pumping current density, which produces a carrier density N in the gain region of the laser diode. The pump current density I of about twice a lasing threshold current density $I_{th}$, is applied at time t=0, and is then left on. The graph shows the increase in carrier density N for the semiconductor gain region until the optical gain of the laser exceeds loss in the cavity. After this point, a first pulse 2-161 builds up, depleting the carrier density and optical gain to a value less than the cavity loss, and is emitted. Subsequently, a second pulse 2-162 builds up, depletes carrier density N, and is emitted. The build-up and depletion of carrier density repeats for several cycles until the laser stabilizes into continuous wave operation (e.g., after about 7 nanoseconds in this example). The cycle of pulses (pulse 2-161, pulse 2-162, and subsequent pulses) are referred to as relaxation oscillations of the laser.

The inventors have recognized and appreciated that a challenge when gain-switching a laser to produce ultrashort-pulses is to avoid deleterious effects of continued relaxation oscillations. For example, if a pump power pulse 2-110 is not terminated quickly enough, at least a second optical pulse 2-162 (due to relaxation oscillation) may begin to build up in the laser cavity and add a tail 2-172 to a gain-switched output pulse 2-170, as depicted in FIG. 2-1C. The inventors have recognized and appreciated that such a tail can be undesirable in some applications, such as applications aimed at distinguishing fluorescent molecules based on fluorescent lifetimes. If the tail of an excitation pulse is not reduced sufficiently quickly, excitation radiation may overwhelm a detector unless wavelength filtering is employed. Alternatively or additionally, a tail on an excitation pulse may continue to excite a fluorescent molecule and may complicate detection of fluorescent lifetime.

If the tail of an excitation pulse is reduced sufficiently quickly, there may be negligible excitation radiation present during fluorescent emission. In such implementations, filtering of the excitation radiation during detection of fluorescent emission may not be needed to detect the fluorescent emission and distinguish fluorescent molecule lifetimes. In some cases, the elimination of excitation filtering can significantly simplify and reduce the cost of an analytic system 1-160 as well as allow a more compact configuration for the system. For example, when a filter is not needed to suppress the excitation wavelength during fluorescent emission, the excitation source and fluorescent detector can be located in close proximity (e.g., on a same circuit board or integrated device, and even within microns of each other).

The inventors have also recognized and appreciated that in some cases, a tail on an excitation pulse may be tolerated. For example, an analytic system 1-160 may have an optical configuration that easily allows for incorporation of a wavelength filter into a detection optical path. The wavelength filter may be selected to reject excitation wavelengths, so that a detector receives quantifiable fluorescence from a biological sample. As a result, excitation radiation from the pulsed optical source does not overwhelm the detected fluorescence.

In some embodiments, a fluorescent molecule's emission lifetime τ may be characterized by a 1/e intensity value, according to some embodiments, though other metrics may be used in some embodiments (e.g., $1/e^2$, emission half-life, etc.). The accuracy of determining a fluorescent molecule's lifetime is improved when an excitation pulse, used to excite the fluorescent molecule, has a duration that is less than the fluorescent molecule's lifetime. Preferably, the excitation pulse has a FWHM duration that is less than the fluorescent molecule's emission lifetime by at least a factor of three. An excitation pulse that has a longer duration or a tail 2-172 with appreciable energy may continue to excite the fluorescent molecule during a time when decaying emission is being evaluated, and complicate the analysis of fluorescent molecule lifetime. To improve fluorescent lifetime determination in such cases, deconvolution techniques may be used to deconvolve the excitation pulse profile from the detected fluorescence.

In some cases, it may be preferable to use ultrashort-pulses to excite fluorescent molecules in order to reduce quenching of the fluorescent molecule or sample. It has been found that extended pumping of a fluorescent molecule may bleach and/or damage the fluorescent molecule over time, whereas higher intensities for shorter durations (even though for a same total amount of energy on the molecule) may not be as damaging to the fluorescent molecule as the prolonged exposure at lower intensity. Reducing exposure time may avoid or reduce photo-induced damage to fluorescent molecules, and increase the amount of time or number of measurements for which the fluorescent molecules may be used in an analytic system 1-160.

In some applications, the inventors have found it desirable for the excitation pulse to terminate quickly (e.g., within about 250 ps from the peak of the pulse) to a power level that is at least about 40 dB below the peak power level of the pulse. Some embodiments may tolerate smaller amounts of power reduction, e.g., between about 20 dB and about 40 dB reduction within about 250 ps. Some embodiments may require similar or higher amounts of power reduction within about 250 ps, e.g., between about 40 dB and about 80 dB in some embodiments, or between about 80 dB and about 120 dB in some embodiments. In some embodiments, these levels of power reduction may be required within about 100 ps from the peak of the pumping pulse.

According to some embodiments, the pulse-separation interval T (see FIG. 1-2) may also be an important aspect of a pulsed laser system. For example, when using a pulsed laser to evaluate and/or distinguish emission lifetimes of fluorescent molecules, the time between excitation pulses is preferably longer than any emission lifetime of the examined fluorescent species in order to allow for sufficiently accurate determination of an emission lifetime. For example, a subsequent pulse should not arrive before an excited fluorescent molecule or ensemble of fluorescent molecules excited from a previous pulse has (or have) had a reasonable amount of time to fluoresce. In some embodiments, the interval T needs to be long enough to determine a time between an excitation pulse that excites a fluorescent molecule and a subsequent photon emitted by the fluorescent molecule after termination of excitation pulse and before the next excitation pulse.

Although the interval between excitation pulses T should be long enough to determine decay properties of the fluorescent species, it is also desirable that the pulse-separation interval T is short enough to allow many measurements to be made in a short period of time. By way of example and not limitation, emission lifetimes (1/e values) of fluorescent molecules used in some applications may be in the range of about 100 picoseconds to about 10 nanoseconds. Therefore, depending on the fluorescent molecules used, a pulse-separation interval as short as about 200 ps may be used, whereas for longer lifetime fluorescent molecules a pulse-separation interval T greater than about 20 nanoseconds may be used. Accordingly, excitation pulses used to excite fluorescence for fluorescent lifetime analysis may have FWHM durations between about 25 picoseconds and about 2 nanoseconds, according to some embodiments.

In some applications, such as fluorescent lifetime imaging, where an integrated time-domain imaging array is used to detect fluorescence and provide data for lifetime analysis and a visual display, the pulse-separation interval T may not need to be shorter than a frame rate of the imaging system. For example, if there is adequate fluorescent signal following a single excitation pulse, signal accumulation over multiple excitation pulses for an imaging frame may not be needed. In some embodiments, a pulse repetition rate $R_p$ of the pulsed optical source 1-110 may be synchronized to a frame rate $R_f$ of the imaging system, so that a pulse repetition rate may be as slow as about 30 Hz. In other embodiments, the pulse repetition rate may be appreciably higher than the frame rate, and fluorescent decay signals for each pixel in an image may be integrated values following multiple excitation pulses.

Figures 2, 2A:
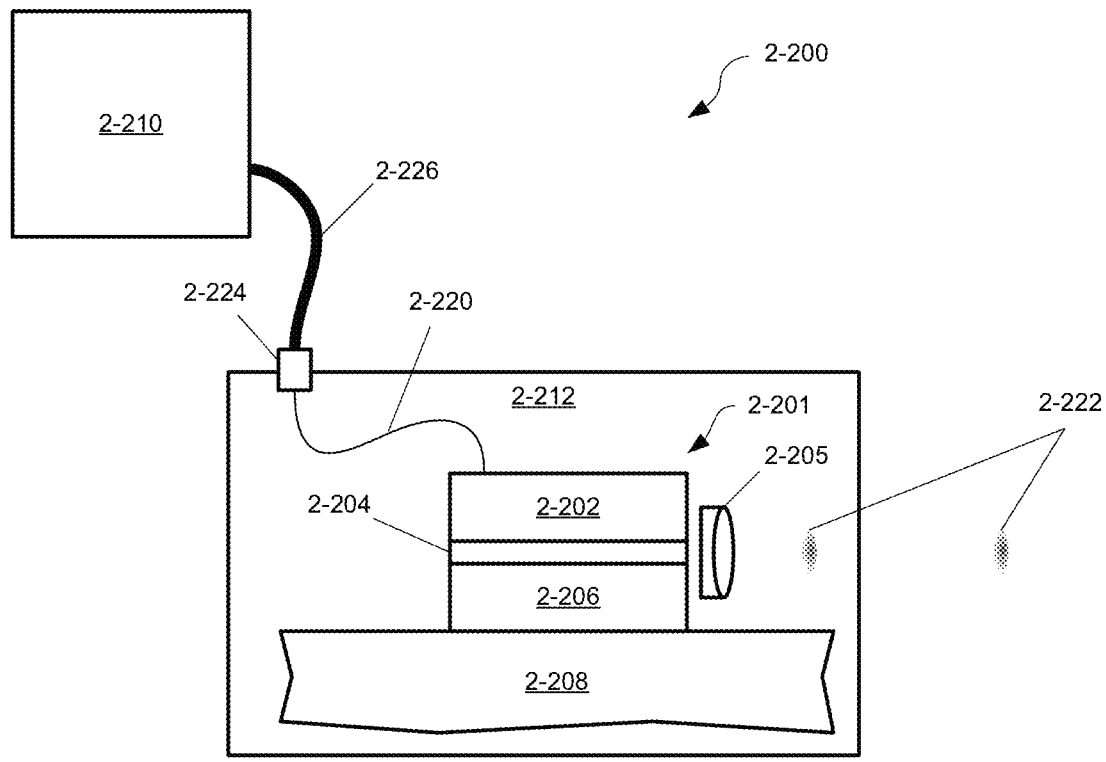

An example of a pulsed optical source 2-200 is depicted in FIG. 2-2A. According to some embodiments, a pulsed optical source 2-200 may comprise a commercial or custom semiconductor laser diode 2-201 (or one or more LEDs) formed on a substrate 2-208. A laser diode or LED may be packaged in a housing 2-212 that includes an electrical connector 2-224. There may be one or more optical elements 2-205 (e.g., one or more lenses) included with the package to reshape and/or change the divergence of an output beam from the laser or LED. The laser diode 2-201 (or one or more LEDs) may be driven by a pulser circuit 2-210 which may provide a sequence of current pulses over a connecting cable 2-226 and at least one wire 2-220 to the diode 2-201. The drive current from the pulser circuit 2-210 may produce a train of optical pulses 2-222 emitted from the laser diode or LED.

One advantage of using LEDs is their lower cost compared to laser diodes. Additionally, LEDs provide a broader, typically incoherent, spectral output that can be better suited for imaging applications (e.g., an LED may produce less optical interference artifacts). For a laser diode, the coherent radiation can introduce speckle unless measures are taken to avoid speckle in the collected images. Also, LEDs can extend excitation wavelengths into the ultraviolet (e.g., down to about 240 nm), and can be used for exciting autofluorescence in biological samples.

According to some embodiments, a laser diode 2-201 may comprise a semiconductor junction comprising a first layer 2-202 having a first conductivity type (e.g., p-type) and a second layer 2-206 having an opposite conductivity type. There may be one or more intermediate layers 2-204 formed between the first and second layers. For example, the intermediate layers may comprise multiple-quantum-well (MQW) layers in which carriers injected from the first and second layers recombine to produce photons. In some embodiments, the intermediate layers may include electron and/or hole blocking layers. The laser diode may comprise inorganic materials and/or organic semiconductor materials in some implementations. The materials may be selected to obtain a desired emission wavelength. For example and for inorganic semiconductors, III-nitride compositions may be used for lasers emitting at wavelengths less than about 500 nm, and III-arsenide or III-phosphide compositions may be used for lasers emitting at wavelengths greater than about 500 nm. Any suitable type of laser diode 2-201 may be used including, but not limited to, a vertical cavity surface emitting laser (VCSEL), an edge-emitting laser diode, or a slab-coupled optical waveguide laser (SCOWL).

According to some embodiments, one or more LEDs may be used instead of a laser diode. An LED may have a lower intensity than a LD, so multiple LEDs may be used. Because an LED does not undergo relaxation oscillations or dynamics associated with lasing action, its output pulses may be of longer duration and have a wider spectral bandwidth than would occur for a laser. For example, the output pulses may be between about 50 ps and about 2 ns, and the spectral bandwidth may be about 20 nm or larger. In some implementations, output pulses from an LED may be between about 100 ps and about 500 ps. Longer excitation pulses may be acceptable for fluorescent molecules having longer decay times. Additionally, an LED may produce an unpolarized or partially polarized output beam. The embodiments of pulser circuits described below may be used to drive one or more LEDs in some implementations of pulsed optical sources.

Figures 2, 2B:
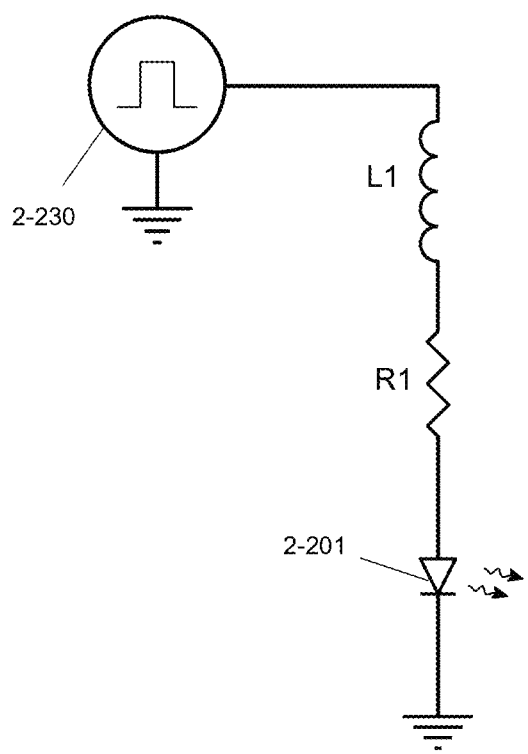

The inventors have recognized that some conventional laser diode systems comprise current driver circuitry that can be modeled as depicted in FIG. 2-2B. For example, the current driver 2-210 may comprise a pulsed voltage source 2-230 configured to deliver current pulses to a laser diode. Connection to the laser diode is typically made through a cable 2-226, adaptor or connector 2-224, and a single wire 2-220 that is bonded to a contact pad on the laser diode 2-210. The connection between the adaptor 2-224 and laser diode may include a series inductance L1 and series resistance R1. The connection may also include small junction capacitances (not shown) associated with contacts and/or the diode junction.

The inventors have recognized and appreciated that increasing the number of wire bonds (e.g., between the connector 2-224 and laser diode 2-201) may reduce the inductance and/or resistance of the connection to a laser diode 2-201. Such a reduction in inductance and/or resistance may enable higher speed current modulation of the laser diode and shorter output pulses. According to some embodiments, a single wire bond 2-220 may be replaced with multiple parallel wire bonds to improve the speed of a laser diode. For example, the number of wire bonds may be increased to three or more. In some implementations, there may be up to 50 wire bonds to a laser diode.

Figures 2, 2C:
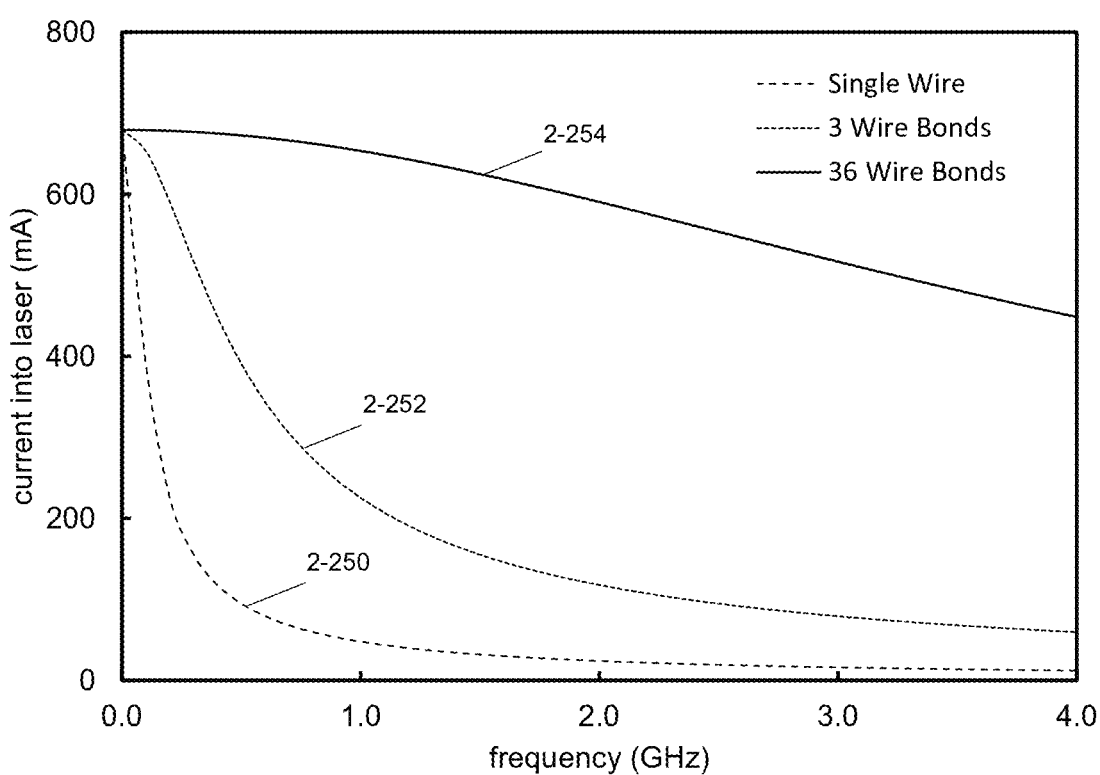

The inventors have investigated the effects of increasing the number of wire bonds 2-220 on a commercial laser diode. An example commercial laser considered was an Oclaro laser diode, model HL63133DG, now available from Ushio, of Cypress, Calif. Results from numerical simulations of increasing a number of wire bonds are illustrated in FIG. 2-2C. The simulation increased the number of wire bonds from a single bond for the commercial device (curve 2-250) to three wire bonds (curve 2-252) and to 36 wire bonds (curve 2-254). The average drive current delivered to the laser diode for a fixed 18V pulse was determined over a range of frequencies for the three different cases. The results indicate that a higher number of wire bonds allows more current to be delivered to the laser diode at higher frequencies. For example, at 1 GHz, the use of just three wire bonds (curve 2-252) allows more than four times as much current to be delivered to the laser diode than for a single wire bond. Since short and ultrashort pulses require higher bandwidth (higher frequency components to form the short pulse), adding multiple wire bonds allows the higher frequency components to drive the laser diode in a shorter pulse than a single wire bond. In some implementations, the multiple wire bonds may extend between a single contact pad or multiple contact pads on a laser diode and an adaptor or connector 2-224 on a laser diode package. The connector may be configured for connection to an external, standardized cable (e.g., to a 50-ohm BNC or SMA cable).

In some embodiments, the number of wire bonds and the wire bond configuration may be selected to match an impedance of the adaptor and/or cable connected to the laser diode. For example, the impedance of the wire bonds may be matched to the impedance of a connector 2-224 to reduce power reflections from the laser diode to the current driver, according to some embodiments. In other embodiments, the impedance of the wire bonds may be selectively mismatched to generate a negative pulse between positive current-driving pulses. Selecting a packaging method for a laser diode (e.g., selecting a number of wire bonds to a laser diode from an adaptor) may improve the current modulation supplied to the laser diode at higher frequencies. This can make the laser diode more responsive to high-speed gain-switching signals, and may enable shorter optical pulses, faster reduction of optical power after the pulse peak, and/or increased pulse repetition rates.

Figures 2, 3:
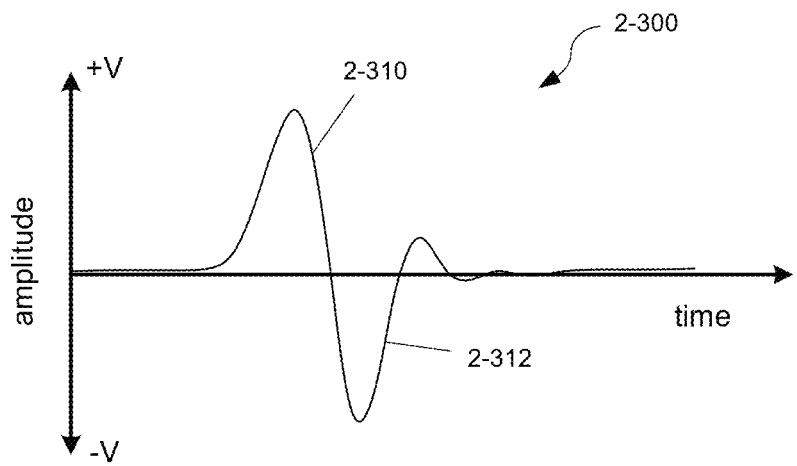

Referring now to FIG. 2-3, the inventors have further recognized and appreciated that applying a bipolar pulse waveform 2-300 to a laser diode may suppress an undesired emission tail 2-172 (see FIG. 2-1C) on produced optical pulses. A bipolar pulse may also be used to shorten an optical pulse from an LED. A bipolar pulse may comprise a first pulse 2-310 of a first polarity followed by a second pulse 2-312 of an opposite polarity. The magnitude of the second pulse 2-312 may be different from the magnitude of the first pulse. In some embodiments, the second pulse may have a magnitude that is approximately equal to or less than the first pulse 2-310. In other embodiments, the second pulse 2-312 may have a magnitude that is greater than the first pulse 2-310.

In some embodiments, the magnitude of the second pulse may be between about 10% of the magnitude of the first pulse and about 90% of the magnitude of the first pulse. In some implementations, the magnitude of the second pulse may be between about 25% of the magnitude of the first pulse and about 90% of the magnitude of the first pulse. In some cases, the magnitude of the second pulse may be between about 50% of the magnitude of the first pulse and about 90% of the magnitude of the first pulse. In some embodiments, an amount of energy in the second pulse may be between about 25% of an amount of energy in the first pulse and about 90% of the energy in the first pulse. In some implementations, an amount of energy in the second pulse may be between about 50% of an amount of energy in the first pulse and about 90% of the energy in the first pulse.

The first drive pulse may forward bias a laser diode junction and thereby generate carriers in the diodes active region that may recombine to produce an optical pulse. The second drive pulse 2-312, opposite in polarity, may reverse bias the diode junction and accelerate removal of carriers from the active region to terminate photon generation. When the second electrical pulse 2-312 is timed to occur at approximately the same time as, or just before (e.g., within about 200 ps), the second relaxation oscillation pulse (see pulse 2-162 of FIG. 2-1B), the carrier concentration that would otherwise produce the second optical pulse is diminished so that the emission tail 2-172 is suppressed.

Various circuit configurations may be used to produce bipolar pulse waveforms. FIG. 2-4A depicts just one example of a circuit that may be used to drive a laser diode or one or more LEDs with a bipolar pulse waveform. In some embodiments, a transmission line 2-410 (e.g., a strip line or co-axial conductor assembly) may be configured in a pulser circuit 2-400 to deliver bipolar pulses to a semiconductor laser diode 2-420 or at least one LED. The transmission line 2-410 may be formed in a U-shaped configuration and biased on a first conductor by a DC voltage source $V_{DD}$ through a charging resistor $R_{ch}$. The transmission line may have an impedance that approximately matches the impedance of a laser diode, according to some embodiments. In some embodiments, the transmission line's impedance may be approximately 50 ohms. In some implementations, the transmission line's impedance may be between approximately 20 ohms and approximately 100 ohms. In some implementations, the transmission line's impedance may be between approximately 1 ohm and approximately 20 ohms.

The pulser 2-400 may further include a terminating resistor $Z_{term}$ connected between the second conductor of the transmission line at one end of the transmission line and a reference potential (e.g., ground in the depicted example). The other end of the second conductor of the transmission line may be connected to the laser diode 2-420. The ends of the transmission line's first conductor may connect to a switch M1 (e.g., a field effect transistor or bipolar junction transistor) that can be activated to periodically shunt the ends of the first conductor to a reference potential (e.g., ground).

In some instances, the terminating impedance $Z_{term}$ may be approximately equal to the impedance of the transmission line 2-410 in order to reduce reflections back into the line. Alternatively, the terminating impedance $Z_{term}$ may be less than the impedance of the line in order to reflect a negative pulse into the line (after shunting by switch M1) and to the laser diode 2-420. In some implementations, the terminating impedance $Z_{term}$ may include a capacitive and/or inductive component selected to control the shape of the reflected negative pulse. A transmission line pulser, as depicted in FIG. 2-4A, may be used to produce electrical bipolar pulses having a repetition rate within a range between about 30 Hz to about 200 MHz. According to some embodiments, a transmission line 2-410 for a transmission line pulser may be formed on a printed circuit board (PCB), as depicted in FIG. 2-5A.

FIG. 2-4B depicts an embodiment of a driver circuit 2-401 connected to an optical semiconductor diode 2-423 (e.g., a laser diode or one or more LEDs) that may be formed using discrete components, and that may be integrated onto a substrate (such as a chip or PCB). In some embodiments, the circuit may be integrated onto a same substrate as a laser diode or LED 2-423. The laser driver circuit 2-401 may comprise a control input 2-405 connected to the gate or base of a transistor M1. The transistor may be a CMOS FET, a bipolar junction transistor, or a high-electron mobility transistor (such as a GaN pHEMT), though other high-speed, high current handling transistors may be used. The transistor may be connected between a current source 2-430 and a reference potential (e.g., a ground potential, though other reference potential values may be used). The transistor M1 may be connected in parallel between the current source 2-430 and reference potential with the laser diode 2-423 (or one or more LEDs) and a resistor $R_1$ that is connected in series with the laser diode. According to some embodiments, the driver circuit 2-401 may further include a capacitor $C_1$ connected in parallel with the resistor $R_1$ between the laser diode and reference potential. Though a transistor M1 is described, any suitable controllable switch having a high conductive and low conductive state may be used.

In operation, the driver circuit 2-401 may provide a current that bypasses the laser diode 2-423 when the transistor M1 is on, or in a conducting state. Therefore, there is no optical output from the laser diode. When the transistor M1 switches off, current may flow through the laser diode due to the increased resistive path at the transistor. The current turns the laser diode on, until the transistor is switched on again. Light pulses may be generated by modulating the control gate of the transistor between on and off states to provide current pulses to the laser diode. This approach can reduce the amount of voltage on the supply and the voltage on the transistor needed to drive the laser compared to some pulsing techniques, which is an important aspect for implementation of such high-speed circuits.

Due to the presence of the resistor $R_1$ and parallel capacitor $C_1$, charge will build up on the capacitor when the diode is forward conducting. This can occur when the transistor M1 is in an "off" state, e.g., a low- or non-conducting state. When the transistor is turned on, the voltage stored across the capacitor will reverse bias the laser diode. The reverse bias effectively produces a negative pulse across the laser diode, which may reduce or eliminate the emission tail 2-172 that would otherwise occur without the negative pulse. The value of the resistor $R_1$ may be selected such that substantially all of the charge on the capacitor will discharge before the switch is subsequently opened and/or a subsequent light pulse is generated by the laser diode. For example, the time constant $t_1 = R_1 C_1$ may be engineered to be less than about one-half or one-third of the pulse repetition interval T. In some implementations, the time constant $t_1 = R_1 C_1$ may be between approximately 0.2 ns and approximately 10 ns.

In some implementations, the transistor M1 may be configured to switch to a conducting state after a first peak of an output light pulse from the laser diode. For example, and referring to FIG. 2-1B, an optical detection and logic circuit may sense the decaying intensity of the first pulse 2-161 and trigger the transistor M1 to switch to a conducting state. In some embodiments, the transistor M1 may be triggered to switch to a conducting state based on a stable clock signal (e.g., triggered with reference to a synchronizing clock edge). In some implementations, the transistor M1 may be triggered to switch to a conducting state according to a predetermined delay time measured from the time at which the transistor M1 switches to a non-conducting state. Switching the transistor M1 to a conducting state at a selected time may reduce the laser power shortly after the peak light pulse, shorten the laser pulse, and/or reduce tail emission of the pulse.

Although the drive circuit shown in FIG. 2-4B shows the current source 2-430 located on the anode side of the laser, in some embodiments a current source may be located alternatively, or additionally, on the cathode side of the laser (e.g., connected between the transistor M1, resistor $R_1$, and a reference potential such as ground).

Other embodiments of drive circuitry for producing ultrashort-pulses are possible. For example, a current pulse drive circuit 2-402 for a laser diode or LED may comprise a plurality of current drive branches connected to a node of a laser diode, as depicted in FIG. 2-4C. The driver circuit 2-402 may be formed using discrete or integrated components and integrated onto a substrate (e.g., an ASIC chip or PCB). In some embodiments, the driver circuit may be integrated onto a same substrate as one or more optical semiconductor diodes 2-425 (e.g., a laser diode or one or more light-emitting diodes). Although the drawing depicts the driver circuit as connected to the anode of the laser diode 2-425, in some embodiments similar drive circuitry may alternatively, or additionally, be connected to the cathode of the laser diode. Drive circuitry connected to the cathode side of the laser diode may employ transistors of an opposite type and voltage sources of opposite polarity than those used on the anode side of the laser diode.

According to some implementations, there may be N circuit branches (e.g., circuit branches 2-432, 2-434, 2-436) configured to apply N forward-bias current pulses to a laser diode 2-425 or LED and M circuit branches (e.g., circuit branch 2-438) configured to apply M reverse-bias current pulses to the laser diode. In FIG. 2-4C, N=3 and M=1, though other values may be used. Each forward-bias current branch may comprise a voltage source $V_i$ configured to deliver a forward-bias current to the laser diode. Each reverse-bias current branch may comprise a voltage source $V_j$ configured to deliver a reverse-bias current to the laser diode. Each circuit branch may further include a resistor $R_i$ connected in series with a switch or transistor Mi. Each circuit branch may include a capacitor $C_i$ connected on one side to a node between the transistor Mi and resistor $R_i$ and connected on the other side to a fixed reference potential. In some embodiments, the capacitance $C_i$ may be junction capacitance associated with the transistor Mi (e.g, source-to-body capacitance), and a separate discrete capacitor may not be provided. In some implementations, at least one additional resistor may be included in series with the diode 2-425 to limit the amount of total current delivered from the circuit branches.

In operation, timed and pulsed control signals may be applied to the control inputs $S_i$ of the switches or transistors Mi, so as to generate a sequence of current pulses from each of the circuit branches that are summed and applied across the laser diode junction. The values of components in each branch ($V_i$, $V_j$, $R_i$, $C_1$) and the timing and pulse duration of control pulses applied to the control inputs $S_i$ can be independently selected to produce a desired bipolar current pulse waveform that is applied to the laser diode 2-425. As just one example, the values of $V_1$, $V_2$, and $V_3$ may be selected to have different values. The values of $R_1$, $R_2$, and $R_3$ may be the same, and the values of $C_1$, $C_2$, and $C_3$ may be the same. In this example, the staggering of pulsed signals to the control inputs $S_i$ may produce a staggered sequence of overlapping current pulses from the forward-bias circuit branches that have similar pulse durations but different pulse amplitudes. A timed pulse from the reverse-bias circuit branch may produce a current pulse of opposite polarity that can quench or rapidly turn off the forward-biasing pulse, and may further produce a reverse-biasing pulse that can suppress tail emission from the laser diode. The reverse-biasing pulse may be timed carefully, so that it at least partially overlaps temporally with one or more of the forward-biasing pulses. Accordingly, the circuit depicted in FIG. 2-4C may be used to synthesize bipolar current pulses as depicted in FIG. 2-3.

FIG. 2-4D depicts another embodiment of a pulse driver 2-403, which may be manufactured using radio-frequency (RF) components. The RF components may be designed to handle signals at frequencies between about 50 MHz and about 1 GHz, according to some embodiments. In some implementations, a pulse driver 2-403 may comprise an input DC block 2-435, which AC couples an input waveform (e.g., a square wave or sinusoidal wave) to the driver. The DC block may be followed by an amplifier 2-440, which produces non-inverted and inverted output waveforms that proceed along separate circuit paths 2-440a, 2-440b, respectively. The first circuit path 2-440a may include one or more adaptors 2-442. A variable phase shifter 2-445 may be included in the second circuit path 2-440b to selectively phase shift the signal in the second path with respect to the signal in the first path.

The first and second circuit paths may connect to non-inverting inputs of an RF logic gate 2-450 (e.g., an AND gate or other logic gate). Inverting inputs of the logic gate 2-450 may be terminated with suitable impedance-matched terminators 2-446 to avoid spurious power reflections at the gate. The non-inverting and inverting outputs of the logic gate 2-450 may connect to a combiner 2-460 along two circuit paths 2-450a, 2-450b. The inverted circuit path 2-450b may include a delay element 2-454 and attenuator 2-456, either or both of which may be adjustable. The delay element may be used to delay the inverted signal with respect to the non-inverted signal, and the attenuator may be used to adjust the amplitude of the inverted signal.

The resulting inverted signal and non-inverted signal from the logic gate may then be summed at the combiner 2-460. The output from the combiner 2-460 may be connected to an RF amplifier 2-470 that provides output bipolar pulses to drive a laser diode or one or more LEDs. The output bipolar pulses may have a waveform as depicted in FIG. 2-4E.

In operation, an input square wave or sinusoidal wave may be AC coupled into the driver and split into the two circuit paths 2-440a, 2-440b as non-inverted and inverted versions. The first amplifier 2-440 may be a limiting amplifier that squares up a sinusoidal waveform, according to some embodiments. In the second circuit path 2-440b the inverted waveform may be phase shifted with an adjustable phase shifter 2-445 to temporally delay the inverted waveform with respect to the non-inverted waveform. The resulting waveforms from the first amplifier 2-440 may then be processed by the RF logic gate 2-450 (e.g., an AND gate) to produce short RF pulses at the non-inverting and inverting outputs of the logic gate. The duration of the short RF pulses may be adjusted using the phase shifter 2-445, according to some embodiments. For example, the phase shifter may adjust a time period during which both the non-inverted waveform and inverted waveform at the input to a logic AND gate 2-450 are simultaneously in an "on" state, which will determine the length of the output pulses.

Referring to FIG. 2-4E, the short inverted pulses 2-417 from the logic gate 2-450 may be delayed an amount δ by the delay element 2-454 with respect to the non-inverted pulses 2-415 and attenuated by attenuator 2-456 to a desired amplitude before being combined with the non-inverted pulse. In some embodiments, the negative-pulse magnitude $|V_{p-}|$ may be less than the positive-pulse amplitude $V_{p+}$. The pulse-separation interval T may be determined by the frequency of the sinusoidal or square wave input into the pulse driver 2-403. The output pulse waveform may, or may not, include a DC offset. Although the output waveform is depicted as having a square-shaped waveform, capacitances and inductances in the RF components and/or cabling may produce output pulses having more rounded waveforms, more like the waveform depicted in FIG. 2-3.

As mentioned earlier in connection with FIG. 2-4C and FIG. 2-4B, the application of current or voltage to a laser diode or LED can be to both the anode and cathode of a diode in some embodiments. A radio-frequency pulse driver circuit 2-404 that can apply a split or differential voltage or current pulse to both the cathode and anode of a diode is depicted in FIG. 2-4F. The front end of the circuit may be similar to the front end of the pulse driver circuit 2-403 depicted in FIG. 2-4D, according to some embodiments. However, in the pulse driver circuit 2-404 the non-inverted and inverted outputs from the logic gate 2-450 may not be combined and instead applied as a differential drive to the anode and cathode of the laser diode. For simplification, the circuitry associated with producing a subsequent negative or reverse biasing pulse is not shown in FIG. 2-4F.

An example of a split or differential drive produced by the differential pulse driver circuit 2-404 is depicted in FIG. 2-4G. A first output from the logic gate 2-450 may produce a positive pulse 2-416 of amplitude $+V_p$, and a second inverted output from the logic gate 2-450 may produce a negative pulse 2-418 of opposite amplitude $-V_p$. The pulse trains may, or may not, have a small DC offset in some embodiments. The presence of the positive pulse 2-416 and negative pulse 2-418 produce a forward biasing pulse across the laser diode having an effective amplitude $2V_p$. By splitting the bias across the laser diode and applying a partial bias to the anode and to the cathode, the amplitude of voltage pulses handled by the pulse driver 2-404 may be effectively reduced by a factor of 2. Accordingly, the pulse driver 2-404 may operate at a higher frequency and produce shorter pulses than it might otherwise be able to achieve for higher amplitude pulses. Alternatively, a pulse driver circuit 2-404 may effectively double the amplitude of the driving pulse applied across a laser diode compared to a driving circuit that only provides a biasing pulse $+V_p$ to the anode of the laser diode. In such embodiments, the power output from the laser diode may be increased.

Another way in which power applied to the laser diode and/or driving speed may be increased is depicted in FIG. 2-4H. According to some embodiments, a plurality of pulse-driver outputs 2-470 may be connected to an anode of a laser diode 2-425 or LED. In this example, four pulse drivers are connected to the anode of the laser diode. In some embodiments, in which differential pulse driver circuitry is used, there may be multiple drivers connected to the cathode of the laser diode as well. Each driver and its associated cabling may have an impedance $Z_O$, and a laser diode 2-425 may have been impedance $Z_L$. Because of their parallel connection, the output impedances of the drivers are divided by the number of drivers connected to the laser diode. The power delivered into the diode may be increased when the combined impedances of the pulse drivers is approximately matched to the impedance of the laser diode 2-425, or vice versa.

The graph in FIG. 2-4I illustrates the increase in efficiency of power coupled into the laser diode 2-425 for four driving sources as a function of the impedance of the laser diode and the laser diode circuit. In the example, the four pulse drivers each have a line impedance of about 50 ohms and are configured to deliver an output pulse of 5 V amplitude with a maximum current of approximately 100 mA. The plot shows that the power coupled into the laser diode reaches a maximum when the laser diode's impedance is at approximately 10 ohms. This value is approximately equal to the parallel output impedance of the four pulse driver outputs 2-470. Accordingly, the impedance of the laser diode 2-425 and its associated circuitry may be designed to approximately match the combined impedance of one or more pulse drivers used to drive the laser diode, according to some embodiments.

Other circuit driver configurations may be used to pulse laser diodes or light-emitting diodes. According to some embodiments, a current injection into a light-emitting diode may be pulsed to produce sub-nanosecond pulses using a pulser circuit described in "A simple sub-nanosecond ultraviolet light pulse generator with high repetition rate and peak power," authored by P. H. Binh et al., *Rev. Sci. Instr. Vol.* 84, 083102 (2013), or in "An ultraviolet nanosecond light pulse generator using a light emitting diode for test of photodetectors" authored by T. Araki et al., *Rev. Sci. Instr. Vol.* 68, 1365 (1997).

Another example of a pulser circuit is depicted in FIG. 2-4J. According to some embodiments, a pulser circuit may comprise a pulse generator 2-480, which may receive one or more clock signals from a system clock, for example, and output a train of electrical pulses to a driver circuit 2-490 that injects current pulses into a laser diode or light-emitting diode responsive to the received electrical pulses from the pulse generator. Accordingly, the output optical pulses may be synchronized to the system clock. The system clock may also be used to operate detection electronics (e.g., an imaging array).

According to some embodiments, the pulse generator 2-480 may be formed from a combination of passive and digital electronic components, and may be formed on a first circuit board. In some cases, a pulse generator may include analog circuit components. In other embodiments, a portion of the pulse generator may be formed on a same board as the driver circuit 2-490, and a portion of the pulse generator may be formed on a separate board remote from the driver circuit. The driver circuit 2-490 may be formed from passive, analog, and digital electronic components, and may be formed on a same or different circuit board as the pulse generator or portion of the pulse generator. An optical source (laser diode or light-emitting diode) may be included on a circuit board with the driver circuit, or may be located in a system and connected to the driver circuit 2-490 by high-speed cabling (e.g., SMA cables). In some implementations, the pulse generator 2-480 and driver circuit 2-490 may include emitter-coupled logic elements. According to some embodiments, the pulse generator 2-480, driver circuit 2-490, and optical semiconductor diode 2-423 may be integrated onto a same printed circuit board, laminate, or integrated circuit.

An example of a pulse generator 2-480 is depicted in FIG. 2-4K. In some implementations, a pulse generator may include a first stage that produces two differential clock outputs, one delayed with respect to the other. The first stage may receive a clock input and include a fan-out 2-481 and delay 2-483. The fan-out may comprise logic drivers and logic inverters arranged to produce two copies of the clock signal and two inverted copies of the clock signal. According to some embodiments, the clock may have a symmetric duty cycle, though asymmetric duty cycles may be used in other embodiments. One copy and one inverted copy may form a differential clock output (CK1, $\overline{CK1}$) and may be delayed by a delay element 2-483 with respect to a second copy and second inverted copy (CK2, $\overline{CK2}$). The delay element may comprise any suitable variable or fixed delay element. Examples of delay elements include RF delay lines and logic gate delays. In some implementations, the first pair of clock signals (CK1, $\overline{CK1}$) is delayed at least a fraction of a clock cycle with respect to the second pair of clock signals (CK2, $\overline{CK2}$). A delay may include one or more full cycles in addition to a fractional cycle. Within each pair of clock signals, the inverted signal may be synchronized to its counterpart so that rising and falling edges of the clocks occur at essentially the same time.

The inventors have found that ultrashort pulsing of a laser diode or LED can be controlled more reliably by adjusting a length of a current-driving pulse from the pulse generator 2-480 and maintaining a fixed amplitude rather than adjusting an amplitude of an ultrashort current-driving pulse. Adjusting the length of the current-driving pulse adjusts an amount of energy delivered to the laser diode per pulse. In some embodiments, high-speed circuits allow for high-resolution control of signal phase (e.g., by adjusting a delay or phase with an analog or digital delay element 2-483), which can be used to obtain high-resolution control of pulse length, according to some implementations.

In some cases, the first stage of the pulse generator 2-480 may comprise a dual-output clock instead of the fan-out 2-481 and delay 2-483. A dual-output clock may generate two differential clock signals, and provide adjustable phase delay between the two differential clock signals. In some implementations, the adjustable phase delay may have a corresponding time resolution as little as 3 ps.

Regardless of how the delayed clock signals CK1, CK2 and their inverses are produced, the signals may be transmitted over high-speed transmission lines to a high-speed logic gate 2-485. For signal transmission over cables between boards, the clock pulses may deteriorate due to cabling. For example, limited bandwidth of transmission lines may distort the clock pulses differently and result in unequal timing. In some implementations, a same type of cabling or transmission line may be used for all the clock signals, so that transmission distortions affect the four clock signals equally. For example, when signal distortions and timing offsets are essentially the same for the four clock signals, a resulting driving pulse produced by the receiving logic gate 2-485 will be essentially the same as it would be if there were no signal distortions from transmission of the clock signals. Accordingly, transmission of clock signals over distances of several feet may be tolerated without affecting the driving-pulse duration. This can be useful for producing ultrashort driving pulses that are synchronized to a system clock and have finely adjustable pulse duration (e.g., adjustable in increments of about 3 ps). If the clock signals are produced locally (e.g., on a same board as the driver circuit 2-490), signal distortions associated with transmission of the clock signals may not be significant and the transmission lines may differ to some extent.

According to some embodiments, the clock signals may be AC coupled with capacitors $C_1$ and provided to data inputs of a high-speed logic gate 2-485. Capacitors $C_1$ may have a capacitance between about 10 nF and about 1 μF. According to some embodiments, the logic gate may comprise an emitter-coupled logic (ECL), two-input, differential AND/NAND gate. An example of logic gate 2-485 includes model MC100EP05 available from ON Semiconductor of East Greenwich, R.I. The AC-coupled signals at the data inputs to the logic gate may appear similar to the signals depicted in FIG. 2-4L, where the horizontal dashed line indicates a zero voltage level. The depictions in FIG. 2-4L do not include distortions introduced by transmission lines. The distortions may round and alter the shapes of the signal profiles, but may not affect the relative phases of the clock signals when a same type and length of cabling is used for each clock signal. Delay element 2-483 may provide a delay Δt indicated by the vertical dashed lines, which may be adjustable in increments as small as 3 ps. In some implementations, a delay element 2-483 may provide an adjustable delay in increments having a value between 1 ps and 10 ps. Logic gate 2-485 may process the received clock signals and produce an output signal at an output port Q corresponding to the delay introduced by delay element 2-483. With a small delay, the output comprises a sequence of short or ultrashort pulses. With a high-speed logic gate 2-485, the pulse durations may be between about 50 ps and about 2 ns (FWHM) in some embodiments, between about 50 ps and about 0.5 ns in some embodiments, between about 50 ps and about 200 ps in some embodiments, and yet between about 50 ps and about 100 ps in some embodiments. The driving pulses from port Q may have a substantially square profile due to high-speed slew rates of the ECL logic gate 2-485. A biasing circuit 2-487 may be connected to the output port Q, and a voltage $V_1$ applied for positive emitter-coupled logic. Output pulses provided from an output terminal $P_{out}$ of the pulse generator 2-480 may include a DC offset, according to some embodiments.

In some implementations, two or more high-speed logic gates 2-485 may be connected in parallel between capacitors $C_1$ and the bias circuit 2-487. The logic gates may be the same, and operate in parallel to provide greater current driving capability at an output of the pulse generator. The inventors have recognized and appreciated that the logic gate 2-485, or gates, need to provide high speed switching (i.e., fast rise and fall times to produce ultrashort driving pulses), and need to provide enough output current to drive a high current transistor M1 in the driver circuit 2-490. In some implementations, connecting logic gates 2-485 in parallel provides improved performance of the pulser circuit, and allows production of sub-100-ps optical pulses.

FIG. 2-4M depicts an embodiment of a driver circuit 2-490, which may be connected to a laser diode or LED 2-423. A driver circuit may include an AC-coupled input, having a capacitor $C_2$ in series with a resistor $R_3$, connected to a gate of a high-speed transistor M1. Capacitance of $C_2$ may be between approximately 0.1 μF and approximately 10 μF, according to some embodiments, and $R_3$ may have a value between approximately 10 ohms and approximately 100 ohms. Transistor M1 may comprise a high-electron-mobility field-effect transistor (HEMT FET) capable of switching high currents (e.g., at least one ampere and, in some cases, up to four amps or more), according to some embodiments. Transistor M1 may be a high-speed transistor capable of switching such large currents at multi-gigahertz speeds. According to some embodiments, transistor M1 may switch more than 1 amp for an electrical pulse duration between about 50 ps and about 2 ns at a repetition rate between 30 Hz and approximately 200 MHz. An example of transistor M1 includes model ATF-50189-BLK available from Avago Technologies of San Jose, Calif. Biasing and filtering circuit elements (e.g., resistors $R_4$, $R_7$, and $C_3$) may be connected between capacitor $C_2$ and the gate of transistor M1. The drain of transistor M1 may be directly connected to a cathode of a laser diode or light-emitting diode 2-423, and a source of transistor M1 may connect to a reference potential (e.g., ground). The anode of diode 2-423 may connect to a diode voltage source $V_{LD}$. A resistor $R_6$ and capacitor $C_4$ may be connected in parallel across diode 2-423. According to some embodiments, resistor $R_6$ may have a value between approximately 50 ohms and approximately 200 ohms, and $C_4$ may have a capacitance between approximately 5 pF and approximately 50 pF. A capacitor $C_5$ (having a value between approximately 1 μF and approximately 5 μF) may also be connected between the diode voltage source $V_{LD}$ and a reference potential (e.g., ground) in parallel with the diode 2-423 and transistor M1.

In some embodiments, a protection diode (not shown) may be connected in a reverse direction across the cathode and anode of the laser diode 2-423. The protection diode may protect the laser diode from excessive reverse bias potential that could break down the laser diode junction.

In operation, a pulse from the pulse generator 2-480 momentarily turns on transistor M1, allowing current to be injected into the active region of laser diode or light-emitting diode 2-423. In some implementations, a large amount of forward current (e.g., up to four amps) flows through transistor M1 briefly. The forward current injects carriers into the laser diode junction and produces a short or ultrashort pulse of optical radiation. When transistor M1 turns off, parasitic inductances continue the flow of current across the light-emitting diode or laser diode, building up charge on the cathode side of the diode, until it can be dissipated by the RC network connected in parallel with the laser diode. This temporary build-up of charge at the cathode provides a reverse bias pulse to the laser diode, and accelerates removal of carriers from the active region. This accelerates termination of the optical pulse.

The inventors have found that the optical pulsing technique described for the embodiment of FIG. 2-4M is superior to pulsing techniques based on differentiating square-wave pulses, because it can provide a higher and shorter current pulse that may be required to turn on a laser diode.

The inventors have assembled various pulse driving circuits and have used them to drive laser diodes. FIG. 2-5A depicts another embodiment of an assembled pulser circuit 2-500. This embodiment implements a pulser 2-400 as depicted in FIG. 2-4A. In the assembled circuit, the transmission line 2-410 is formed as a parallel-plate strip line patterned in a U-shaped configuration on a printed circuit board, as depicted in the figure. A GaN pHEMT transistor was used as a shunting switch M1 to short two ends of the U-shaped transmission line. The pulser circuit 2-500 can be operated at repetition rates of up to 100 MHz and used to drive a 50 ohm load. In some embodiments, a pulser circuit may be operated at repetition rates between approximately 10 MHz and approximately 1 GHz.

A measured waveform from the pulser 2-500 is depicted in FIG. 2-5B. The waveform shows a positive pulse having an amplitude of approximately 19.5 V followed by a negative pulse that reaches an amplitude of approximately −5 V following the positive pulse. The duration of the positive pulse is approximately 1.5 nanoseconds. Referring again to FIG. 2-4A, the pulser 2-500 was constructed to a have a terminating resistor $Z_{term}$ of approximately 50 ohms and a pull-up or charging resistor $R_{ch}$ of approximately 200 ohms.

The value of $Z_{term}$ was chosen to reduce power reflections from the terminating resistance back into the transmission line. The bias applied to the transmission line 2-410 was 100 V, and the switch M1 was driven at a repetition rate of 100 MHz. Approximately −1.3 V of DC bias was coupled to the diode via a bias tee, to tune the relative offset from 0 V bias. The driving pulse for the switch M1 was a square-wave signal oscillating between approximately 0 V and approximately 2 V.

A commercial test-bed driver was used to drive a commercial laser diode (Ushio model HL63133DG) to produce sub-100-ps optical pulses. Optical pulse measurements are shown in FIG. 2-5C and FIG. 2-5D. As shown in FIG. 2-5C, pulses with reduced tail emission were produced at a repetition rate of 100 MHz. The average power from the laser diode was measured to be about 8.3 milliwatts. The pulse duration, shown in FIG. 2-5D, was measured to be approximately 84 picoseconds. The intensity of the optical emission from the laser diode was found to be reduced by approximately 24.3 dB approximately 250 ps after the peak of the pulse. Even though the laser diode had a single bond wire to the diode, sub-100-ps pulses were produced. Shorter pulses (e.g., between about 25 ps and about 75 ps) may be produced with multiple bond wires or with further improvements to the pulser circuit.

FIG. 2-6A depicts one example of a semiconductor laser 2-600 that may be used to produce optical pulses by gain switching, according to any of the above-described gain-switching apparatus and techniques. The laser and pulse driving circuitry may be mass produced and manufactured at low-cost. For example, the laser may be microfabricated as an edge-emitting device using planar integrated circuit technology. Such a laser may be referred to as a slab-coupled optical waveguide laser (SCOWL). The drawing depicts an end-on, elevation view of the laser. The laser may be formed from a GaAs/AlGaAs material system (e.g., to emit radiation in the green, red, or infrared regions of the optical spectrum), but other material systems (such as GaN/AlGaN) may be used in some implementations (e.g., to emit radiation in the green, blue, or ultraviolet regions of the spectrum). Laser diodes may be manufactured from other semiconductor material systems that include, but are not limited to: InP, AlInGaP, InGaP, and InGaN.

According to some embodiments, a SCOWL may be formed on an n-type substrate or buffer layer 2-627 (e.g., a GaAs substrate or GaAs layer that comprises Al). For example, a buffer layer may comprise $Al_xGa_{1-x}As$ where x is between approximately 0.25 and approximately 0.30. The refractive index of the substrate or base layer may have a first value $n_1$ that is between about 3.4 and 3.5, according to some embodiments. An electron-transport layer 2-617 of low-doped n-type semiconductor material may be formed on the substrate 2-627. In some embodiments, the electron-transport layer 2-617 may be formed by epitaxial growth to comprise $Al_xGa_{1-x}As$ where x is between approximately 0.20 and approximately 0.25 and have an n-type dopant concentration of approximately $5\times10^{16}$ cm$^{-3}$. The thickness h of the electron-transport layer may be between about 1 micron and about 2 microns. The transport layer 2-617 may have a second value of refractive index $n_2$ that is greater than $n_1$. A multiple quantum well region 2-620 may then be formed on the electron-transport layer 2-617. The multiple quantum well region may comprise alternating layers of materials (e.g., alternating layers of AlGaAs/GaAs) having different doping concentrations that modulate energy band-gaps in the MQW region. The layers in the quantum well region 2-620 (which may have thicknesses between approximately 20 nm and approximately 200 nm) may be deposited by epitaxy, atomic layer deposition, or a suitable vapor deposition process. The multiple quantum well region may have an effective third value of refractive index $n_3$ that is greater than $n_2$. A hole-transport layer 2-615 of p-type doped material may be formed adjacent the quantum well region, and have a value of refractive index $n_4$ that is less than $n_2$. In some embodiments, the values of refractive index for the different regions of a SCOWL may be as illustrated in FIG. 2-6B, according to some embodiments. In some embodiments, a SCOWL may comprise GaN semiconductor and its alloys or InP semiconductor and its alloys.

The term "adjacent" may refer to two elements arranged within close proximity to one another (e.g., within a distance that is less than about one-fifth of a transverse or vertical dimension of a larger of the two elements). In some cases there may be intervening structures or layers between adjacent elements. In some cases adjacent elements may be immediately adjacent to one another with no intervening structures or elements.

After the layers of the laser device have been deposited, trenches 2-607 may be etched into the layers to form an active region of the laser having a width w that is between about 0.25 micron and about 1.5 microns. An n-contact 2-630 may be formed on a first surface of the device, and a p-contact 2-610 may be formed on the p-type transport layer 2-615, adjacent the active region. Exposed surfaces of the semiconductor layers may be passivated with an oxide or other electrically insulating layer, according to some embodiments.

The trenches 2-607 adjacent the active region, and the values of refractive indices $n_1$, $n_2$, $n_3$, and $n_4$ confine the optical mode of the laser to a lasing region 2-625 that is adjacent to the quantum wells and under the devices central rib, as depicted in the drawing. A SCOWL may be designed to couple higher-order transverse modes, that might otherwise form and lase in the lasing region 2-625, to lossy higher-order slab modes in adjacent regions. When designed properly, all higher-order transverse modes from the lasing region 2-625 have high relative loss compared to the fundamental mode in the lasing region and will not lase. In some implementations, the transverse optical mode of the SCOWL 2-600 may be a single transverse mode. The width of the optical mode may be between approximately 0.5 micron and approximately 6 microns. A mode profile 2-622, taken in the x direction, may be shaped as depicted in FIG. 2-6B, according to some embodiments. In other implementations, a SCOWL may produce multiple optical transverse modes to illuminate a region of interest. The length of the active region (along a dimension into the page) may be between 20 microns and 10 mm, in some embodiments. The output power of the SCOWL may be increased by selecting a longer length of the active region. In some embodiments, a SCOWL may deliver an average output power of more than 300 mW.

Although a semiconductor laser (e.g., a SCOWL) and pulser circuitry may be combined to make a low-cost, ultrafast, pulsed laser suitable for many applications, the turn-off rate shown in FIG. 2-5D may not be suitable for some fluorescent lifetime analyses. In some cases, a more rapid turn-off may be needed. For example, the inventors have found that some measurements based on fluorescent lifetime may require the tail of the pulse to extinguish to a level between approximately 25 dB and approximately 40 dB below the pulse peak within 250 ps after the pulse peak. In some cases, the pulse power may need to drop to this range of values within 100 ps after the pulse peak. In some implementations, the pulse tail may need to drop to a level between approximately 40 dB and approximately 80 dB below the pulse peak within 250 ps after the pulse peak. In some implementations, the pulse tail may need to drop to a level between approximately 80 dB and approximately 120 dB below the pulse peak within 250 ps after the pulse peak.

One approach for further suppressing the emission tail of a pulse is to include a saturable absorber with a pulsed laser or high-brightness LED system. According to some embodiments, a semiconductor saturable absorber 2-665 may be incorporated onto a same substrate as a semiconductor laser 2-600 or high-brightness LED, as depicted in FIG. 2-6C. The semiconductor laser may comprise a SCOWL structure that includes a quantum well region 2-620, according to some embodiments. The SCOWL may be driven with a pulsed source 2-670, such as a pulser circuit 2-400 or other pulsing circuit described above.

Adjacent to one end of the SCOWL, a saturable absorber 2-665 may be formed. The saturable absorber 2-665 may comprise a region having a band-gap that is tailored to absorb photons from the semiconductor laser. For example, the saturable absorber may comprise a single quantum well or multiple quantum wells that have at least one energy band gap that is approximately equal to a characteristic energy of the laser's optical emission. In some embodiments, a saturable absorber may be formed by ion implanting a region of the diode laser, so as to electrically isolate the region within the diode laser cavity. A negative bias may be applied to the region to encourage absorption rather than gain for the same laser diode structure. At high fluence from the laser 2-600, the valence band of the saturable absorber may become depleted of carriers and the conduction band may fill, impeding further absorption by the saturable absorber. As a result, the saturable absorber bleaches, and the amount of radiation absorbed from the laser is reduced. In this manner, the peak of a laser pulse may "punch through" the saturable absorber with a smaller attenuation in intensity than the tail or wings of the pulse. The tail of the pulse may then be suppressed further with respect to the peak of the pulse.

According to some embodiments, a high reflector (not shown) may be formed or located at one end of the device. For example, the high reflector may be located at one end of the laser, farthest from the saturable absorber, so as to redirect laser emission through the saturable absorber and increase output power. According to some embodiments, an anti-reflection coating may be applied to an end of the saturable absorber and/or SCOWL to increase extraction from the device.

According to some embodiments, a saturable absorber may include a biasing supply 2-660. The biasing supply may be used to sweep carriers out of the active region after each pulse and improve the response of the saturable absorber. In some embodiments, the bias may be modulated (e.g., at the pulse repetition rate) to make the saturable recovery time be time-dependent. This modulation may further improve pulse characteristics. For example, a saturable absorber can suppress a pulse tail by differentially higher absorption at low intensity, if the recovery time of the saturable absorber is sufficient. Such differential absorption can also reduce the pulse length. The recovery time of a saturable absorber may be adjusted by applying or increasing a reverse bias to the saturable absorber.

III. System Timing and Synchronization

Referring again to FIG. 1-1, regardless of the method and apparatus that is used to produce short or ultrashort-pulses, a system 1-100 may include circuitry configured to synchronize at least some electronic operations (e.g., data acquisition and signal processing) of an analytic system 1-160 with the repetition rate of optical pulses from the optical source. There are at least two ways to synchronize the pulse repetition rate to electronics on the analytic system 1-160. According to a first technique, a master clock may be used as a timing source to trigger both generation of pulses at the pulsed optical source and instrument electronics. In a second technique, a timing signal may be derived from the pulsed optical source and used to trigger instrument electronics.

FIG. 3-1 depicts a system in which a clock 3-110 provides a timing signal at a synchronizing frequency $f_{sync}$ to both a pulsed optical source 1-110 (e.g., a gain-switched pulsed laser or pulsed LED) and to an analytic system 1-160 that may be configured to detect and process signals that result from interactions between each excitation pulse 1-120 and biological, chemical, or other physical matter. As just one example, each excitation pulse may excite one or more fluorescent molecules of a biological sample that are used to analyze a property of the biological sample (e.g., cancerous or non-cancerous, viral or bacterial infection, blood glucose level). For example, non-cancerous cells may exhibit a characteristic fluorescent lifetime of a first value $\tau_1$, whereas cancerous cells may exhibit a lifetime of a second value $\tau_2$ that is different from and can be distinguished from the first lifetime value. As another example, a fluorescent lifetime detected from a sample of blood may have a lifetime value and/or intensity value (relative to another stable marker) that is dependent on blood glucose level. After each pulse or a sequence of several pulses, the analytic system 1-160 may detect and process fluorescent signals to determine a property of the sample. In some embodiments, the analytic system may produce an image of an area probed by the excitation pulses that comprises a two or three-dimensional map of the area indicating one or more properties of regions within the imaged area.

Regardless of the type of analysis being done, detection and processing electronics on the analytic system 1-160 may need to be carefully synchronized with the arrival of each optical excitation pulse. For example, when evaluating fluorescent lifetime, it is beneficial to know the time of excitation of a sample accurately, so that timing of emission events can be correctly recorded.

A synchronizing arrangement depicted in FIG. 3-1 may be suitable for systems in which the optical pulses are produced by active methods (e.g., external control). Active pulsed systems may include, but are not limited to gain-switched lasers and pulsed LEDs. In such systems, a clock 3-110 may provide a digital clock signal that is used to trigger pulse production (e.g., gain switching or current injection into an LED junction) in the pulsed optical source 1-110. The same clock may also provide the same or synchronized digital signal to an analytic system 1-160, so that electronic operations on the instrument can be synchronized to the pulse-arrival times at the instrument.

The clock 3-110 may be any suitable clocking device. In some embodiments, the clock may comprise a crystal oscillator or a MEMS-based oscillator. In some implementations, the clock may comprise a transistor ring oscillator.

The frequency $f_{sync}$ of a clock signal provided by the clock 3-110 need not be a same frequency as the pulse repetition rate R. The pulse repetition rate may be given by R=1/T, where T is the pulse-separation interval. In FIG. 3-1, the optical pulses 1-120 are depicted as being spatially separated by a distance D. This separation distance corresponds to the time T between arrival of pulses at the analytic system 1-160 according to the relation T=D/c where c is the speed of light. In practice, the time T between pulses can be determined with a photodiode and oscilloscope. According to some embodiments, $T=f_{sync}/N$ where N is an integer greater than or equal to 1. In some implementations, $T=Nf_{sync}$ where N is an integer greater than or equal to 1.

FIG. 3-2 depicts a system in which a timer 3-220 provides a synchronizing signal to the analytic system 1-160. In some embodiments, the timer 3-220 may derive a synchronizing signal from the pulsed optical source 1-110, and the derived signal is used to provide a synchronizing signal to the analytic system 1-160.

According to some embodiments, the timer 3-220 may receive an analog or digitized signal from a photodiode that detects optical pulses from the pulse source 1-110. The timer 3-220 may use any suitable method to form or trigger a synchronizing signal from the received analog or digitized signal. For example, the timer may use a Schmitt trigger or comparator to form a train of digital pulses from detected optical pulses. In some implementations, the timer 3-220 may further use a delay-locked loop or phase-locked loop to synchronize a stable clock signal to a train of digital pulses produced from the detected optical pulses. The train of digital pulses or the locked stable clock signal may be provided to the analytic system 1-160 to synchronize electronics on the instrument with the optical pulses.

In some embodiments, two or more pulsed optical sources 1-110a, 1-110b may be needed to supply optical pulses at two or more different wavelengths to an analytic system 1-160, as depicted in FIG. 3-3. In such embodiments, it may be necessary to synchronize pulse repetition rates of the optical sources and electronic operations on the analytic system 1-160. In some implementations, if two pulsed optical sources use active methods to produce pulses, the techniques described above in connection with FIG. 3-1 may be used. For example, a clock 3-110 may supply a clock or synchronizing signal at a synchronizing frequency $f_{sync}$ to both pulsed optical sources 1-110a, 1-110b, and to the analytic system 1-160.

In some implementations, it may be beneficial to interleave pulses in time from two pulsed optical sources, as depicted in FIG. 3-4A and FIG. 3-4B. When pulses are interleaved, a pulse 3-120a from a first source 1-110a may excite one or more samples at the analytic system 1-160 with a first characteristic wavelength $\lambda_1$ at a first time $t_1$. Data representative of the first pulse's interaction with the one or more samples may then be collected by the instrument. At a later time $t_2$, a pulse 3-120b from a second source 1-110b may excite one or more samples at the analytic system 1-160 with a second characteristic wavelength $\lambda_2$. Data representative of the second pulse's interaction with the one or more samples may then be collected by the instrument. By interleaving the pulses, effects of pulse-sample interactions at one wavelength may not intermix with effects of pulse-sample interactions at a second wavelength. Further, characteristics associated with two or more fluorescent markers may be detected.

Figures 2, 3, 4, 4A:
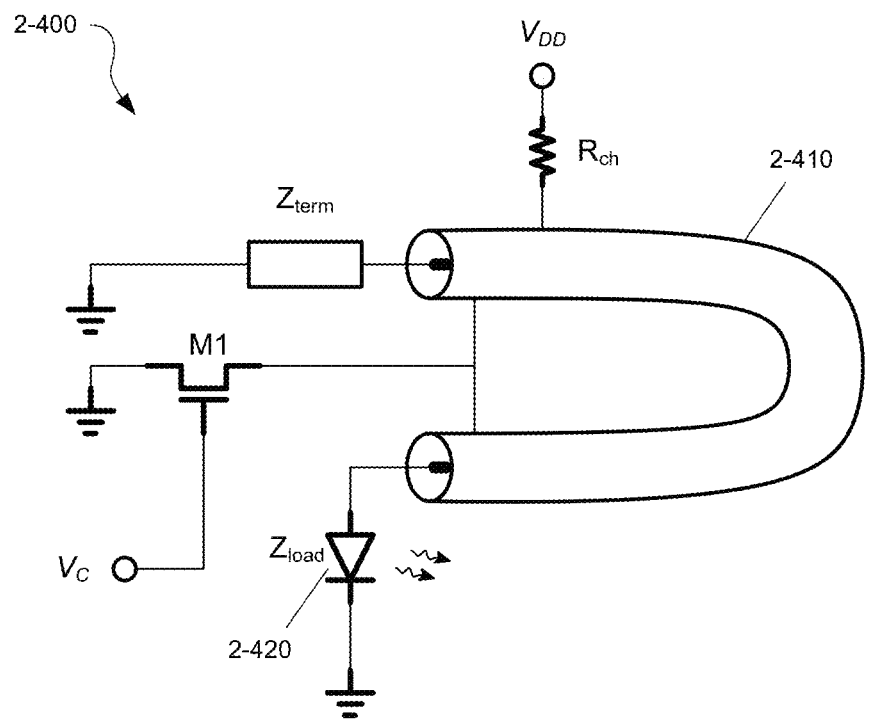
Figures 2, 3, 4, 4B:
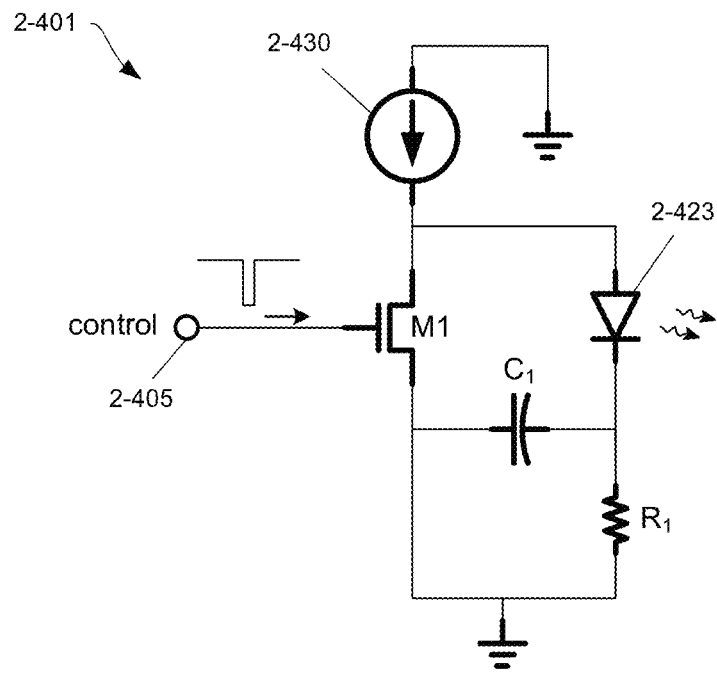
Figures 2, 3, 4, 4C:
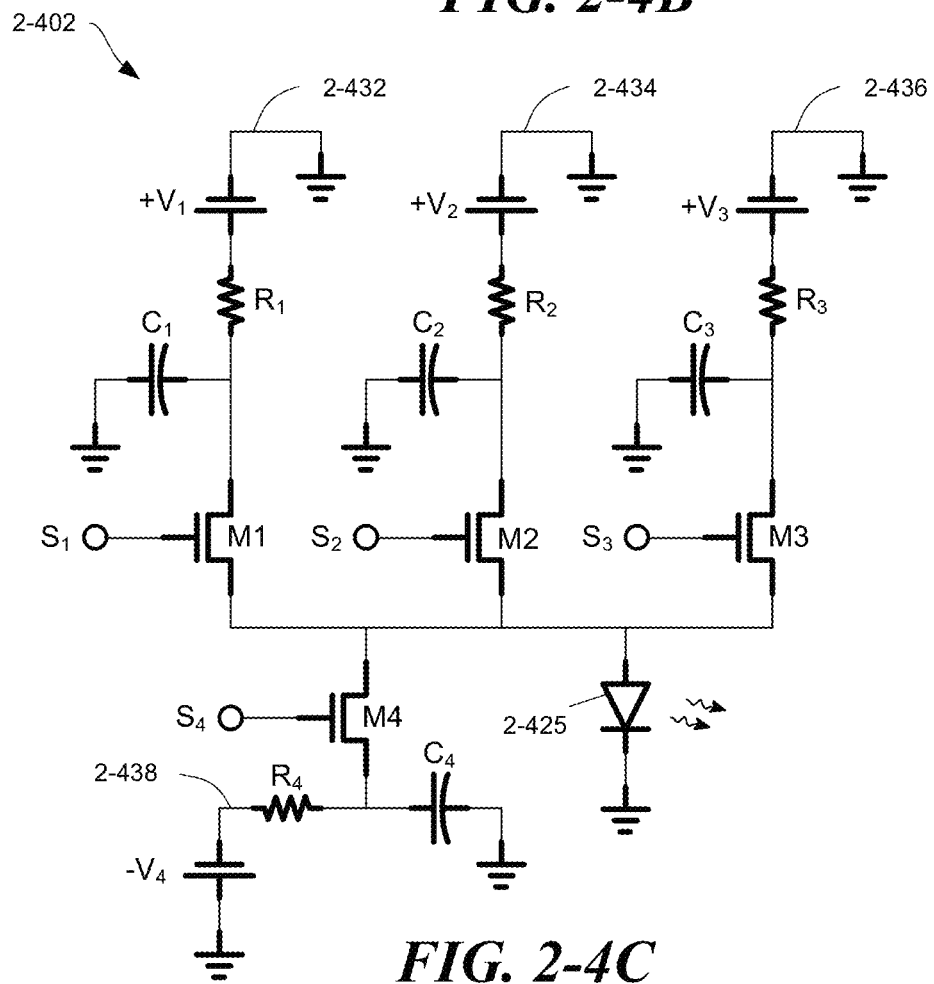
Figures 2, 3, 4, 4D:
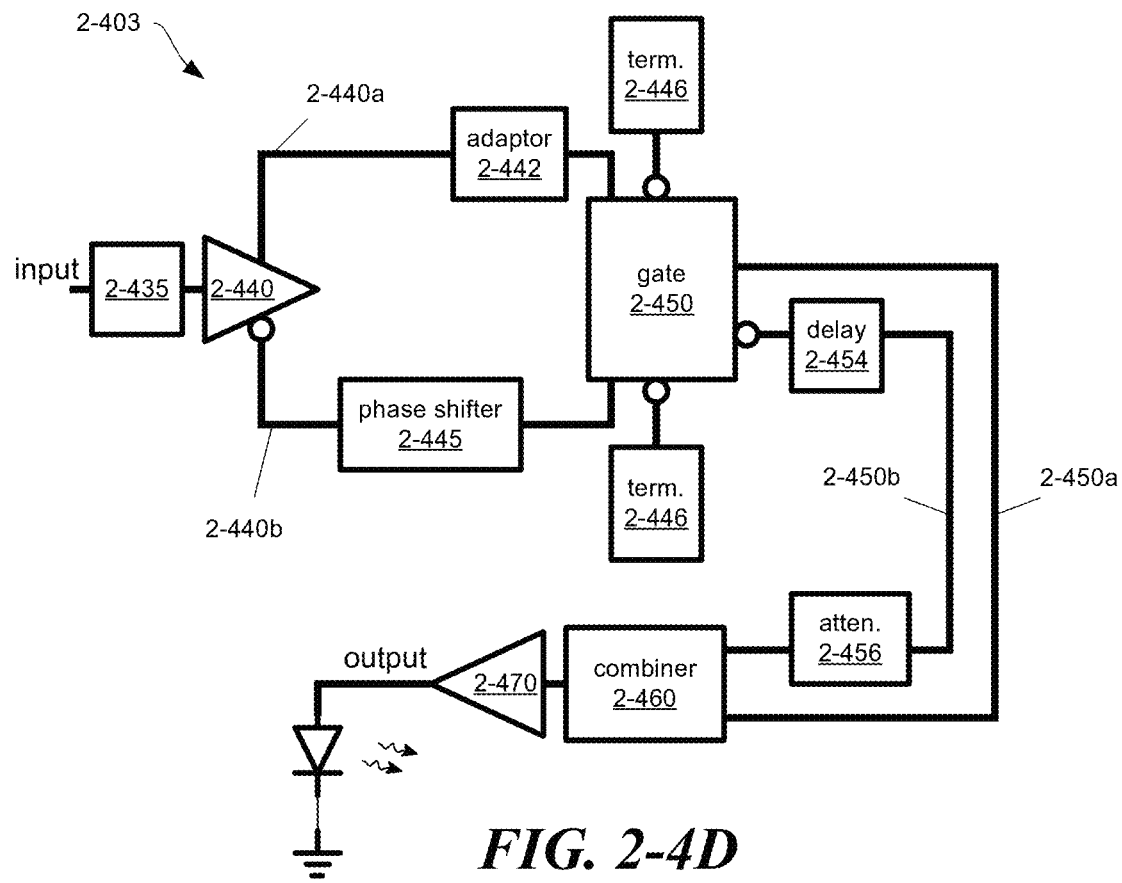
Figures 2, 3, 4, 4E:
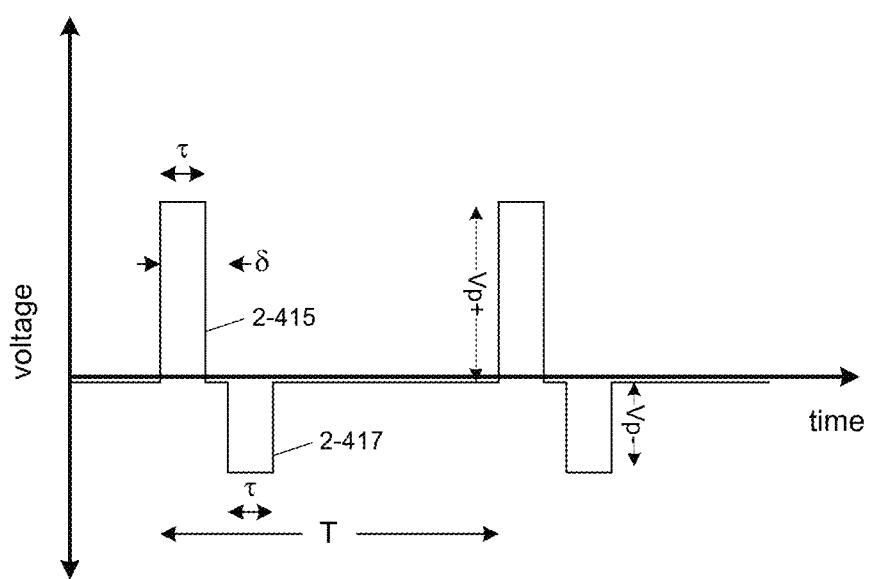
Figures 2, 3, 4, 4F:
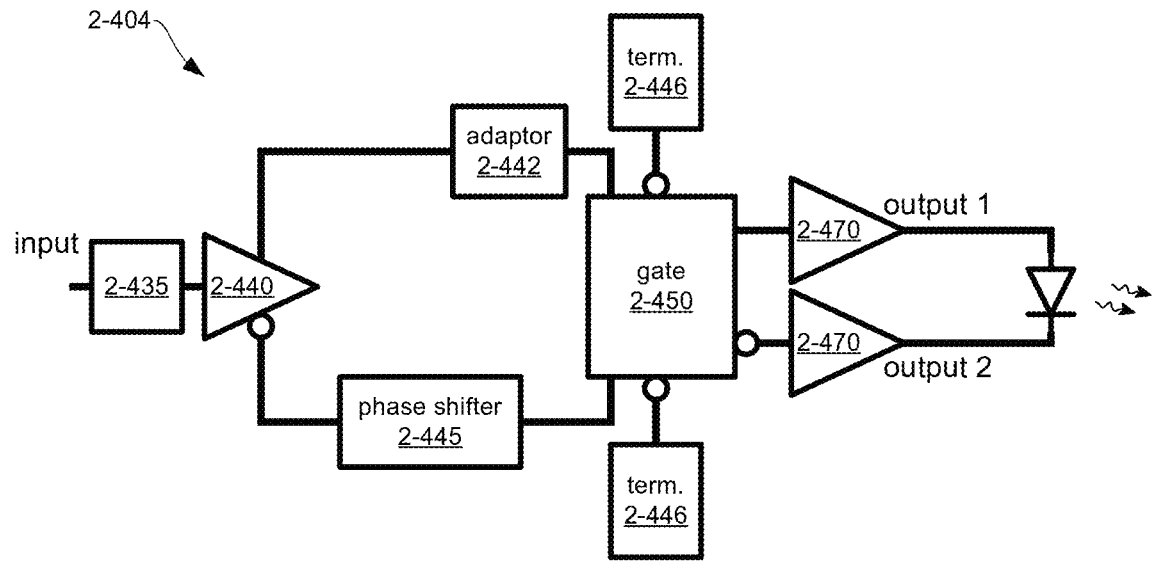
Figures 2, 3, 4, 4G:
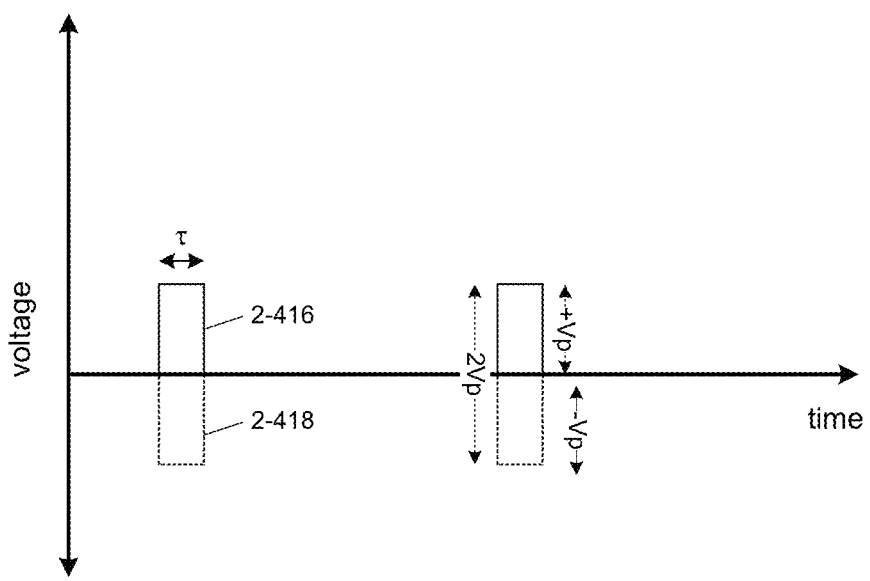
Figures 2, 3, 4, 4H:
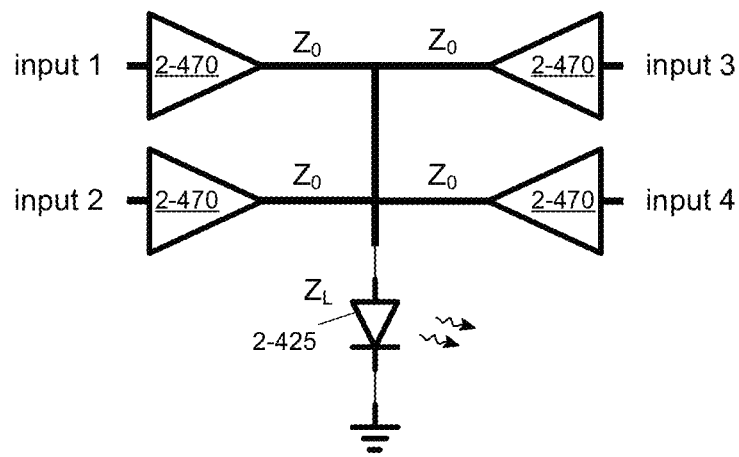
Figures 2, 3, 4, 4I:
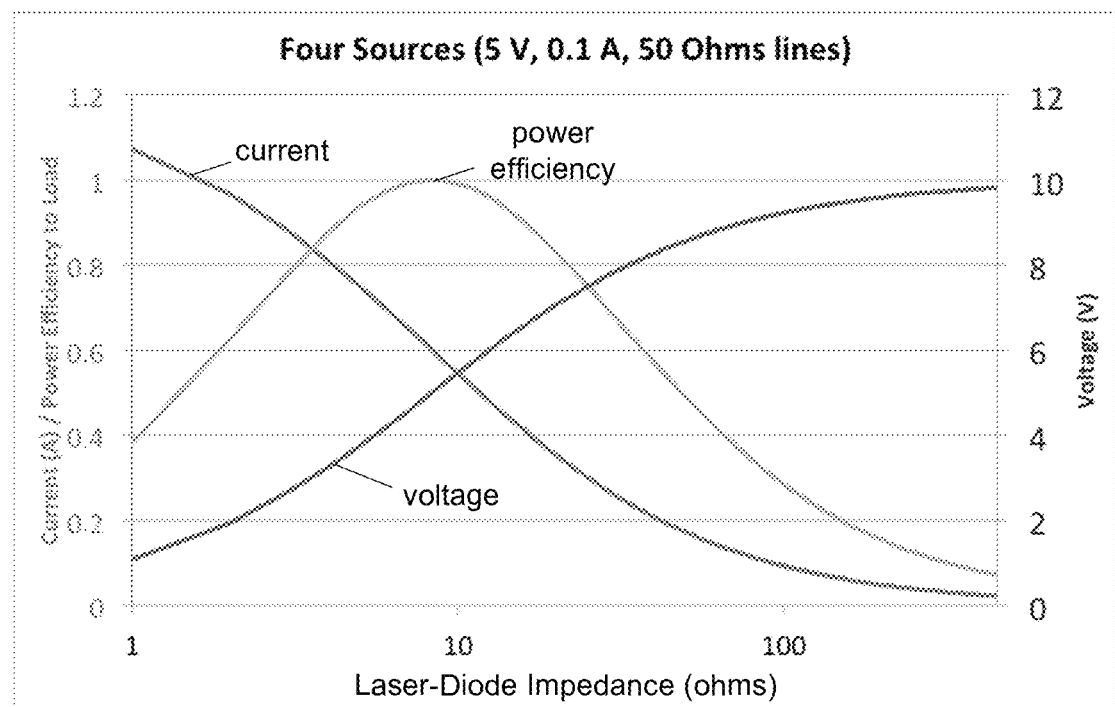
Figures 2, 3, 4, 4J:
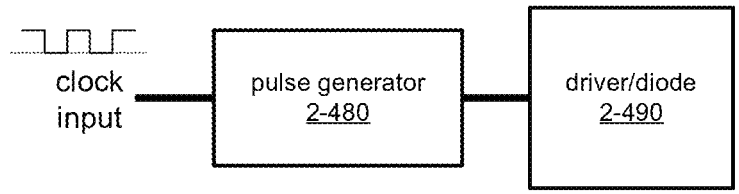
Figures 2, 3, 4, 4K:
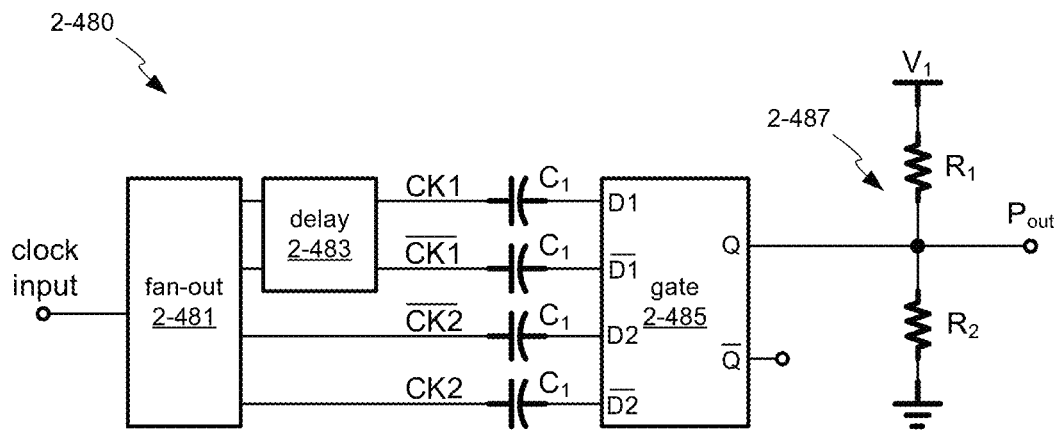
Figures 2, 3, 4, 4L:
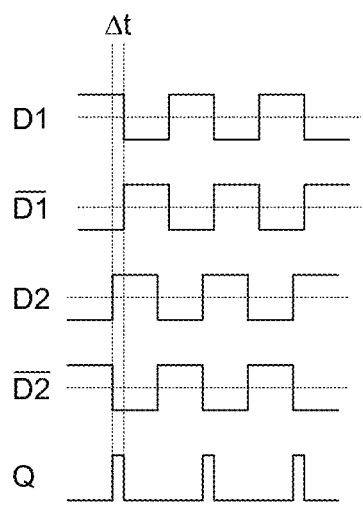
Figures 2, 3, 4, 4M:
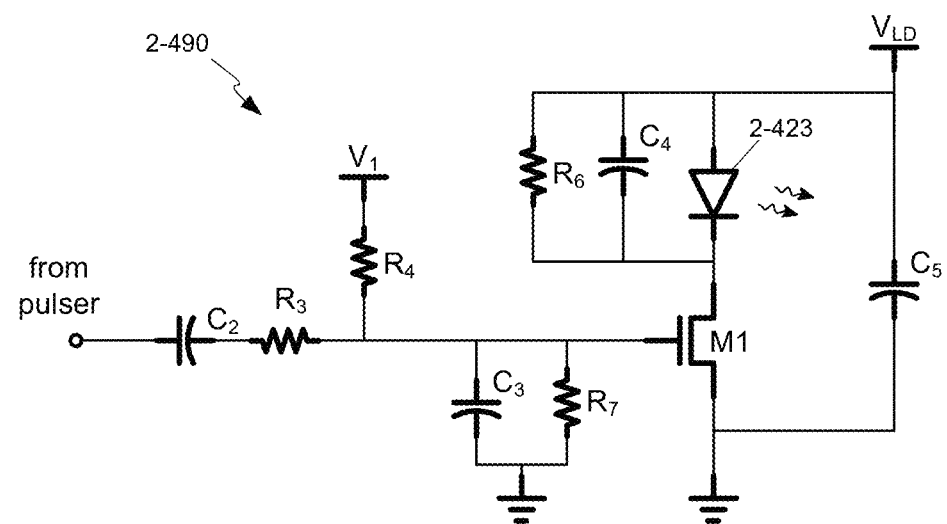

Pulses may be interleaved with timing and synchronization circuitry, as depicted in FIG. 3-4A. Methods described in connection with FIG. 3-3 may be used to synchronize pulse trains from the two pulsed optical sources 1-110a, 1-110b, and to synchronize electronics and operations on the analytic system 1-160 with the arrival of pulses. To interleave the pulses, pulses of one pulsed optical source may be phase-locked or triggered out of phase with pulses from the other pulsed optical source. For example, pulses of a first pulsed optical source 1-110a may be phase-locked (using a phase-locked loop or delay-locked loop) or triggered to be 180 degrees out of phase with pulses from the second pulsed optical source 1-110b, though other phase or angle relationships may be used in some embodiments. In some implementations, a timing delay may be added to a trigger signal provided to one of the pulsed optical sources. The timing delay may delay a trigger edge by approximately one-half the pulse-separation interval T. According to some embodiments, a frequency-doubled synchronization signal may be generated by a timer 3-220, and provided to the instrument 3-160 for synchronizing instrument electronics and operations with the arrival of interleaved pulses from the pulsed optical sources.

IV. Time-Domain Applications for Pulsed Optical Sources

Pulsed optical sources described above are useful for various time-domain applications. In some embodiments, pulsed optical sources may be used in systems configured to detect and/or characterize a condition or property of a biological sample based on fluorescent lifetimes, fluorescent wavelengths, fluorescent intensities, or a combination thereof. Pulsed optical sources may also be used in time-of-flight systems. Time-of-flight systems may include imaging systems and ranging systems that illuminate a target with a short or ultrashort optical pulse, and then detect backscattered radiation from the target to form a three-dimensional image of the target or determine a distance to the target.

In a time-domain application that utilizes fluorescence, a pulsed optical source operating at a first characteristic wavelength may excite one or more fluorescent molecules in a sample, and the analytic system may detect and analyze fluorescent emission from the sample at one or more wavelengths that are different from the pulsed optical source's wavelength. According to some embodiments, one or more properties of a biological sample may be determined based upon an analysis of fluorescent lifetimes from one or more fluorescent molecules present in the sample. In some implementations, additional characteristics of fluorescent emission (e.g., wavelength, intensity) may be analyzed to further aid in determination of one or more properties of a biological sample. Systems that determine properties of biological samples based on fluorescent lifetimes may be imaging or non-imaging systems. When configured as an imaging system, a pixel array may be used for fluorescent detection, and imaging optics may be placed between the sample and pixel array to form an image of at least a portion of the sample on the pixel array. In some implementations, a non-imaging system may use a pixel array to detect fluorescence from a plurality of samples in parallel.

An instrument 4-100 for determining properties of biological samples based at least in part on fluorescent lifetime analysis and using pulsed optical sources is depicted in FIG. 4-1, according to some embodiments. Such an instrument may comprise one or more pulsed optical sources 4-120, a time-binning photodetector 4-150, an optical system 4-130 (which may be one or more lenses, and may include one or more optical filters), and a transparent window 4-140 that may be pressed against a subject or on which a biological sample may be placed. The pulsed optical source or sources and optical system may be arranged so that optical pulses from the source or sources illuminate an area through the window 4-140. Fluorescent emission that is excited by the optical excitation pulses may be collected by the optical system 4-130 and directed to the time-binning photodetector 4-150 which may discern lifetimes of one or more fluorescent molecules, as described further below. In some implementations, photodetector 4-150 may be non-imaging. In some implementations, photodetector 4-150 may comprise an array of pixels, each having time-binning capability, to form images of a sample. The image data may include spatially-resolved fluorescent lifetime information as well as conventional imaging information. Components of the instrument may be mounted in a casing 4-105, which may be small in size so that the instrument can be operated as a hand-held device. The optical source(s) 4-120 and photodetector 4-150 may or may not be mounted on a same circuit board 4-110. In some embodiments, the instrument 4-100 may include a microprocessor or microcontroller, and/or may include data-communication hardware so that data can be transmitted to an external device (e.g., a smart phone, laptop, PC) for processing and/or data storage.

Systems configured to analyze samples based on fluorescent lifetimes may detect differences in fluorescent lifetimes between different fluorescent molecules, and/or differences between lifetimes of the same fluorescent molecules in different environments that affect fluorescent lifetimes. By way of explanation, FIG. 4-2 plots two different fluorescent emission probability curves (A and B), which may be representative of fluorescent emission from two different fluorescent molecules, for example, or a same fluorescent molecule in different environments. With reference to curve A, after being excited by a short or ultrashort optical pulse, a probability $p_A(t)$ of a fluorescent emission from a first molecule may decay with time, as depicted. In some cases, the decrease in the probability of a photon being emitted over time may be represented by an exponential decay function $p_A(t) = P_{Ao} e^{-t/\tau_A}$, where $P_{Ao}$ is an initial emission probability and $\tau_A$ is a temporal parameter associated with the first fluorescent molecule that characterizes the emission decay probability. $\tau_A$ may be referred to as the "fluorescence lifetime," "emission lifetime," or "lifetime" of the first fluorescent molecule. In some cases, the value of $\tau_A$ may be altered by a local environment of the fluorescent molecule. Other fluorescent molecules may have different emission characteristics than that shown in curve A. For example, another fluorescent molecule may have a decay profile that differs from a single exponential decay, and its lifetime may be characterized by a half-life value or some other metric.

A second fluorescent molecule may have a decay profile that is exponential, but has a measurably different lifetime $\tau_B$, as depicted for curve B in FIG. 4-2. Different fluorescent molecules may have lifetimes or half-life values ranging from about 0.1 ns to about 20 ns, in some embodiments. In the example shown, the lifetime for the second fluorescent molecule of curve B is shorter than the lifetime for curve A, and the probability of emission is higher sooner after excitation of the second molecule than for curve A.

The inventors have recognized and appreciated that differences in fluorescent emission lifetimes can be used to discern between the presence or absence of different fluorescent molecules and/or to discern between different environments or conditions in a sample that affect lifetime of a fluorescent molecule or molecules. In some cases, discerning fluorescent molecules based on lifetime (rather than emission wavelength, for example) can simplify some aspects of an analytic system 1-160. As an example, wavelength-discriminating optics (such as wavelength filters, dedicated detectors for each wavelength, dedicated pulsed optical sources at different wavelengths, and/or diffractive optics) may be reduced in number or eliminated when discerning fluorescent molecules based on lifetime. In some cases, a single pulsed optical source may be used to excite different fluorescent molecules that emit within a same wavelength region of the optical spectrum but have measurably different lifetimes. An analytic system that uses a single pulsed optical source, rather than multiple sources at different wavelengths, to excite and discern different fluorescent molecules emitting in a same wavelength region can be less complex to operate and maintain, more compact, and may be manufactured at lower cost.

Although analytic systems based on fluorescent lifetime analysis may have certain benefits, the amount of information obtained by an analytic system may be increased by allowing for additional detection techniques. For example, some analytic systems 1-160 may additionally be configured to discern one or more properties of a sample based on fluorescent wavelength and/or fluorescent intensity.

Referring again to FIG. 4-2, according to some embodiments, different fluorescent lifetimes may be distinguished with a photodetector that is configured to time-bin fluorescent emission events following excitation of a fluorescent molecule. The time binning may occur during a single charge-accumulation cycle for the photodetector. The concept of determining fluorescent lifetime by time-binning of emission events is depicted graphically in FIG. 4-3. At time $t_1$ or just prior to $t_1$, a fluorescent molecule or ensemble of fluorescent molecules of a same type (e.g., the type corresponding to curve B of FIG. 4-2) is (are) excited by a short or ultrashort optical pulse. For an ensemble of molecules, the intensity of emission may have a time profile as depicted in FIG. 4-3.

For a single molecule or a small number of molecules, however, the emission of fluorescent photons occurs according to the statistics of curve B in FIG. 4-2. A time-binning photodetector 4-150 may accumulate emission events into discrete time bins (three indicated in FIG. 4-3) that are measured with respect to the excitation time of the fluorescent molecule(s). When a large number of emission events are summed, the resulting time bins may approximate the decaying intensity curve shown in FIG. 4-3, and the binned signals can be used to distinguish between different fluorescent molecules or different environments in which a fluorescent molecule is located.

Examples of a time-binning photodetector are described in international application No. PCT/US2015/044360, which is incorporated herein by reference, and an embodiment of such a photodetector for explanation purposes is depicted in FIG. 4-4. A single time-binning photodetector 4-400 may comprise a photon-absorption/carrier-generation region 4-402, a carrier-travel region 4-406, and a plurality of carrier-storage bins 4-408a, 4-408b, 4-408c all formed on a semiconductor substrate. The carrier-travel region may be connected to the plurality of carrier-storage bins by carrier-transport channels 4-407. Only three carrier-storage bins are shown, but there may be more. There may be a read-out channel 4-410 connected to the carrier-storage bins. The photon-absorption/carrier-generation region 4-402, carrier-travel region 4-406, carrier-storage bins 4-408a, 4-408b, 4-408c, and read-out channel 4-410 may be formed by doping the semiconductor locally and/or forming adjacent insulating regions to provide photodetection capability and confine carriers. A time-binning photodetector 4-400 may also include a plurality of electrodes 4-420, 4-422, 4-432, 4-434, 4-436, 4-440 formed on the substrate that are configured to generate electric fields in the device for transporting carriers through the device.

In operation, fluorescent photons may be received at the photon-absorption/carrier-generation region 4-402 at different times and generate carriers. For example, at approximately time $t_1$ three fluorescent photons may generate three carrier electrons in a depletion region of the photon-absorption/carrier-generation region 4-402. An electric field in the device (due to doping and/or an externally applied bias to electrodes 4-420 and 4-422, and optionally or alternatively to 4-432, 4-434, 4-436) may move the carriers to the carrier-travel region 4-406. In the carrier-travel region, distance of travel translates to a time after excitation of the fluorescent molecules. At a later time $t_5$, another fluorescent photon may be received in the photon-absorption/carrier-generation region 4-402 and generate an additional carrier. At this time, the first three carriers have traveled to a position in the carrier-travel region 4-406 adjacent to the second storage bin 4-408b. At a later time $t_7$, an electrical bias may be applied between electrodes 4-432, 4-434, 4-436 and electrode 4-440 to laterally transport carriers from the carrier-travel region 4-406 to the storage bins. The first three carriers may then be transported to and retained in the first bin 4-408a and the later-generated carrier may be transported to and retained in the third bin 4-408c. In some implementations, the time intervals corresponding to each storage bin are at the sub-nanosecond time scale, though longer time scales may be used in some embodiments (e.g., in embodiments where fluorophores have longer decay times).

The process of generating and time-binning carriers after an excitation event (e.g., excitation pulse from a pulsed optical source) may occur once after a single excitation pulse or be repeated multiple times after multiple excitation pulses during a single charge-accumulation cycle for the photodetector 4-400. After charge accumulation is complete, carriers may be read out of the storage bins via the read-out channel 4-410. For example, an appropriate biasing sequence may be applied to at least electrode 4-440 and a downstream electrode (not shown) to remove carriers from the storage bins 4-408a, 4-408b, 4-408c.

Figures 2, 3, 4, 5, 5A:
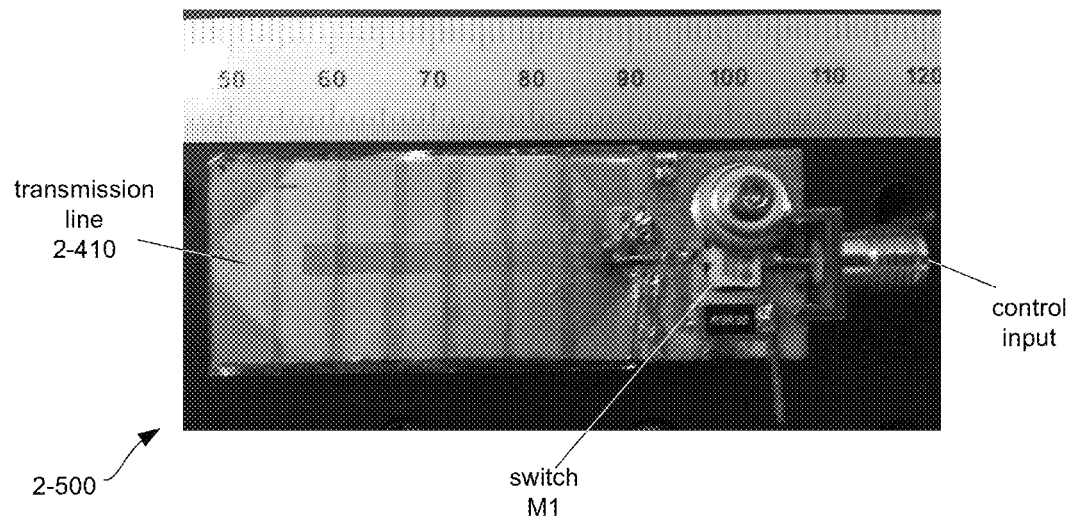

Aspects of signal acquisition are depicted in further detail for multiple excitation pulses in FIG. 4-5A and FIG. 4-5B. In FIG. 4-5A, multiple excitation pulses are applied to a sample at times $t_{e1}$, $t_{e2}$, $t_{e3}$, . . . . Following each excitation pulse, one or more fluorescent emission events may occur at times $t_{fn}$, which lead to the accumulation of carriers into the different carrier-storage bins depending on when the emission event occurs. After a number of excitation events, the accumulated signal in each carrier-storage bin may be read out to provide a signal sequence, which may be represented as a histogram 4-510 (depicted in FIG. 4-5B). The signal sequence may indicate a number of photons detected during each binned time interval after excitation of the fluorophore (s) in a sample, and is representative of a fluorescent emission decay rate. The signal sequence, or histogram, may be used to distinguish between different fluorescent molecules or different environments in which a fluorescent molecule exists.

Figures 2, 3, 4, 5, 5B:
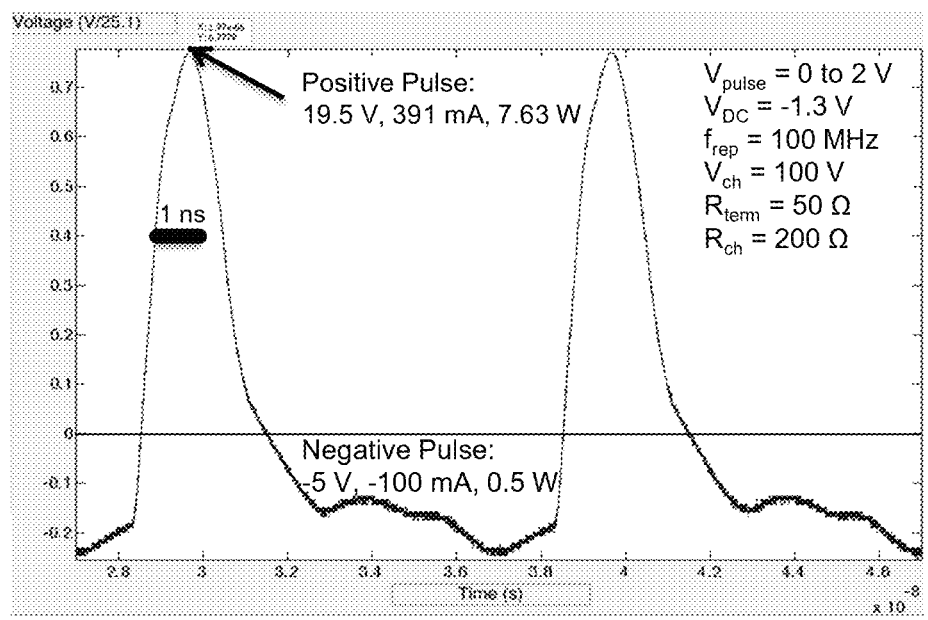
Figures 2, 3, 4, 5, 5C:
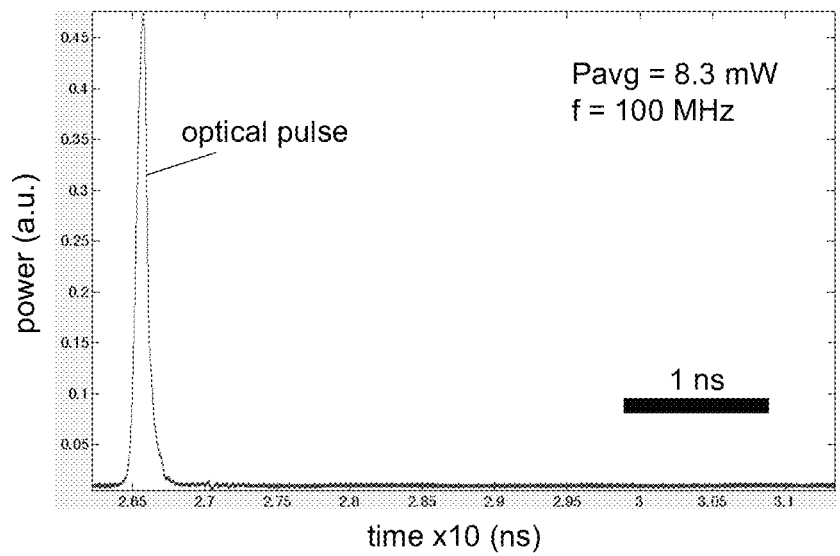
Figures 2, 3, 4, 5, 5D:
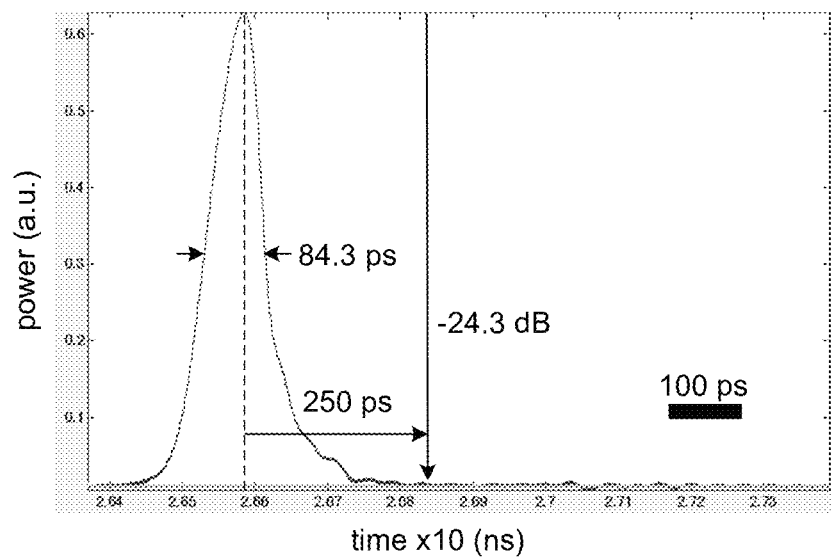
Figures 2, 3, 4, 5, 6, 6A:
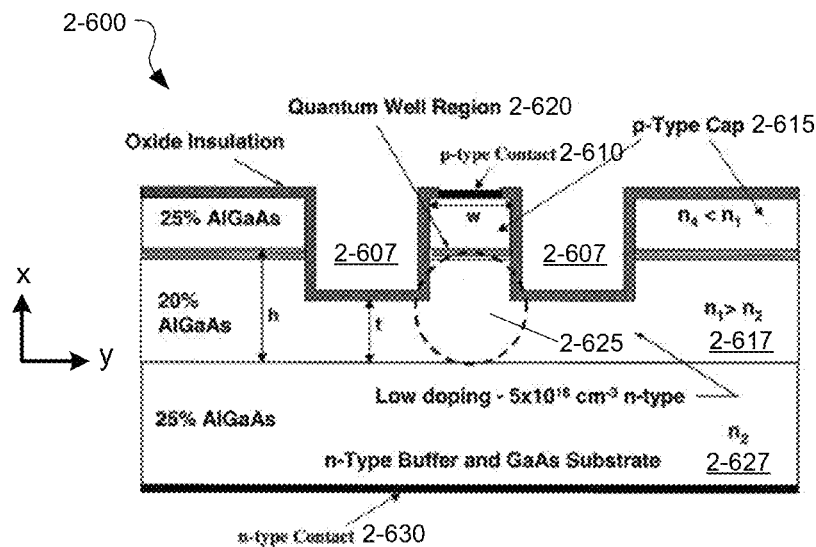
Figures 2, 3, 4, 5, 6, 6B:
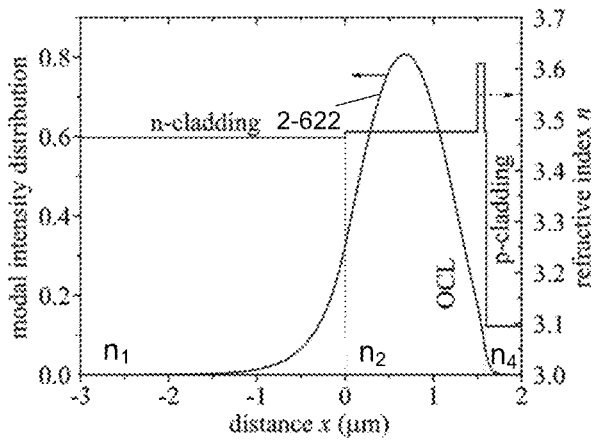
Figures 2, 3, 4, 5, 6, 6C:
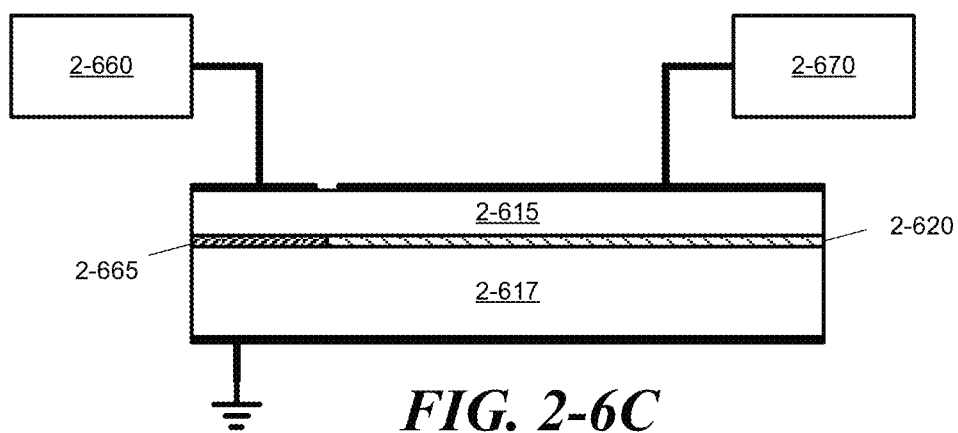
Figures 1, 3:
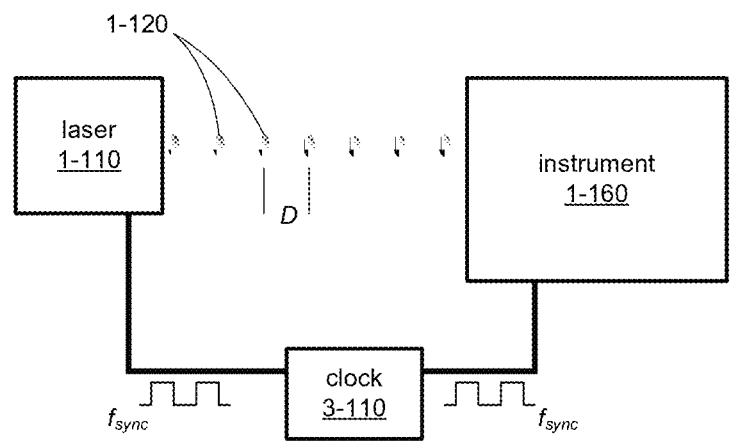
Figures 2, 3:
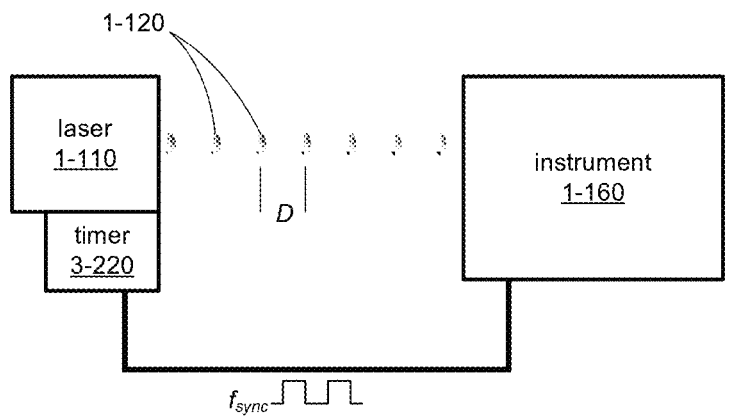
Figure 3:
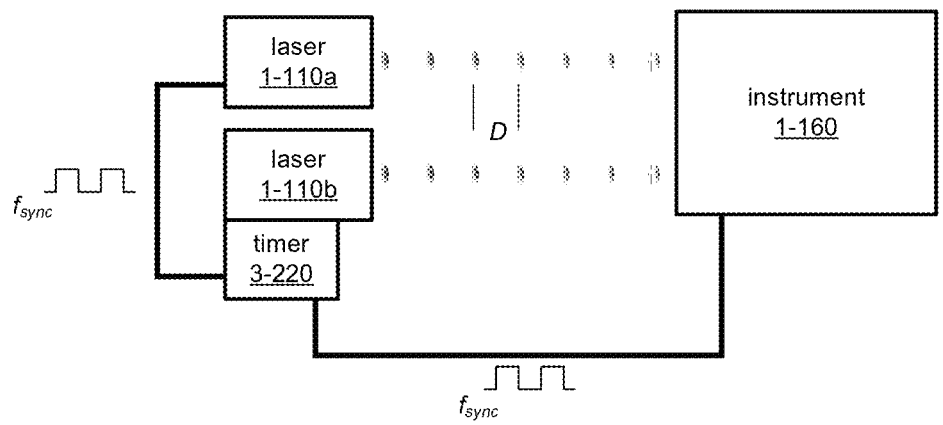
Figures 3, 4, 4A:
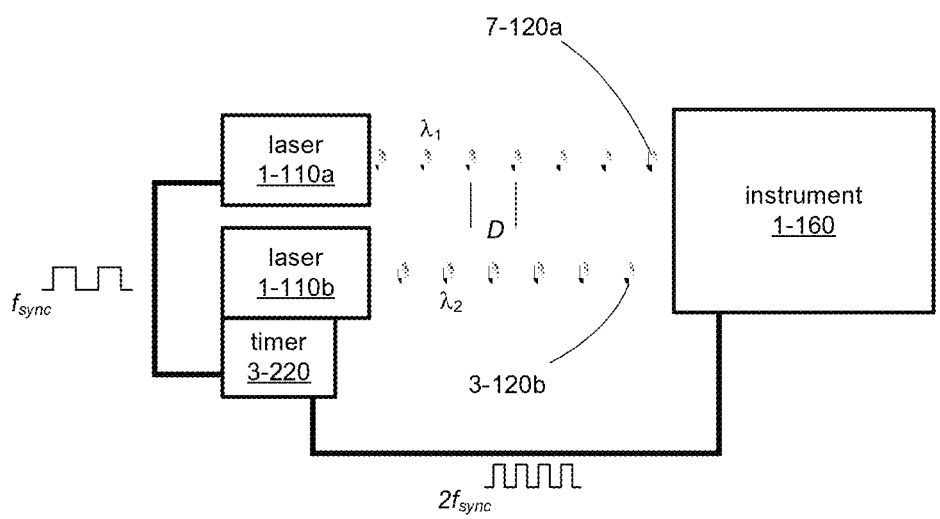
Figures 3, 4, 4B:
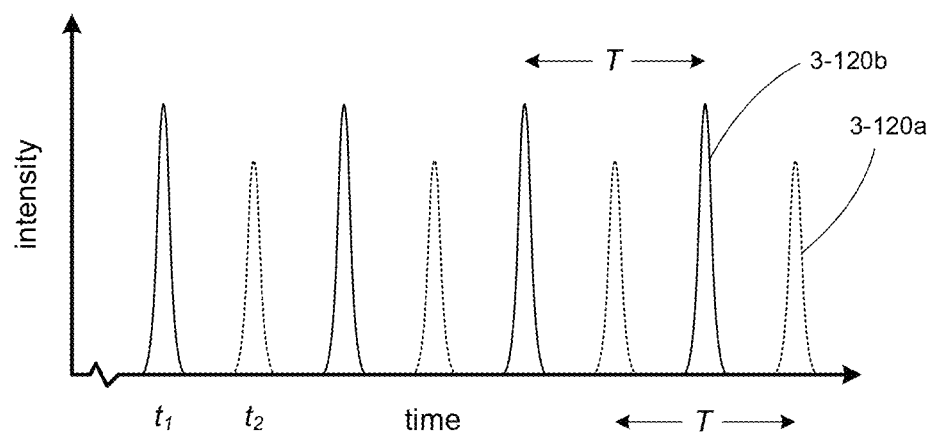
Figures 1, 4:
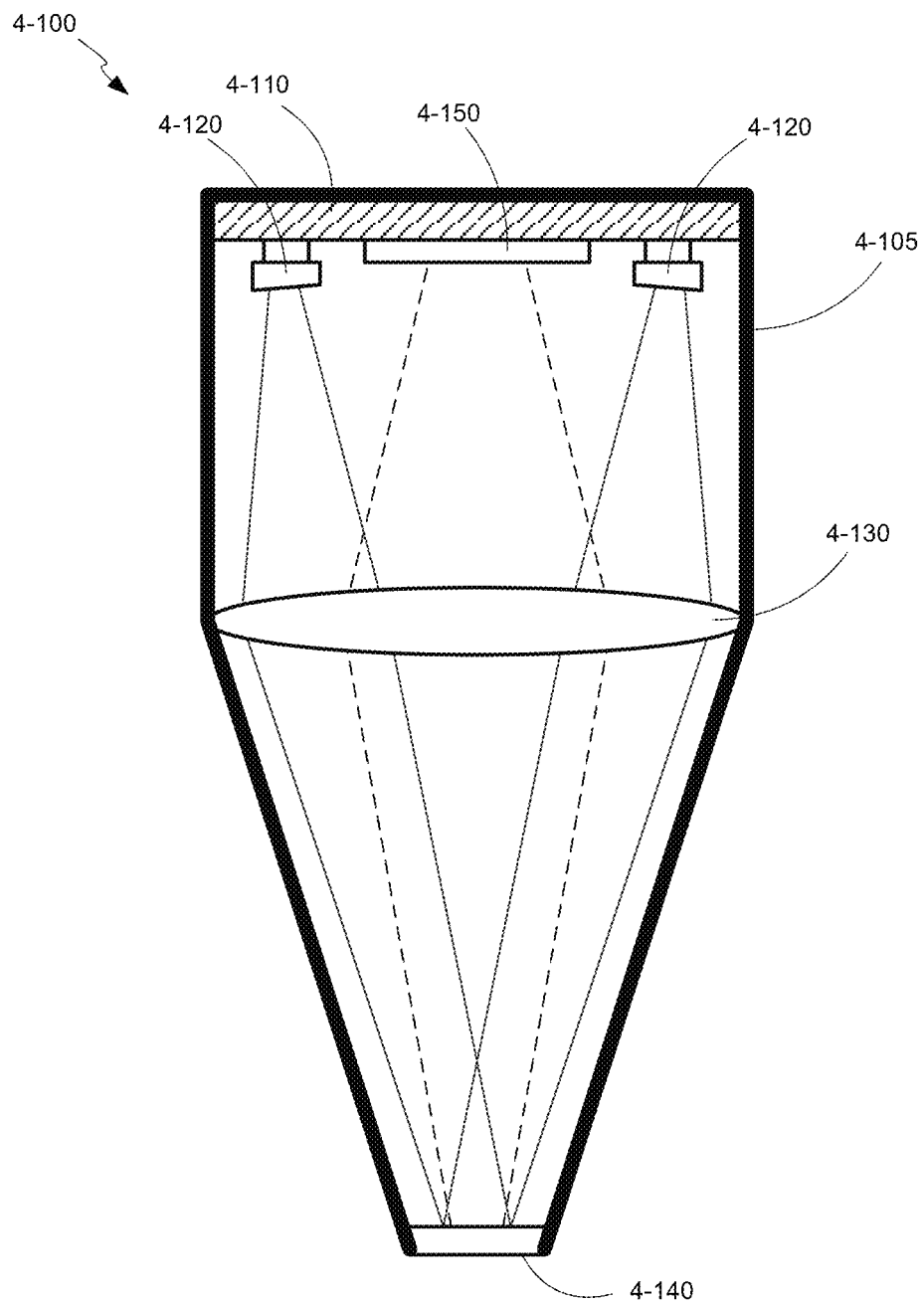
Figures 2, 4:
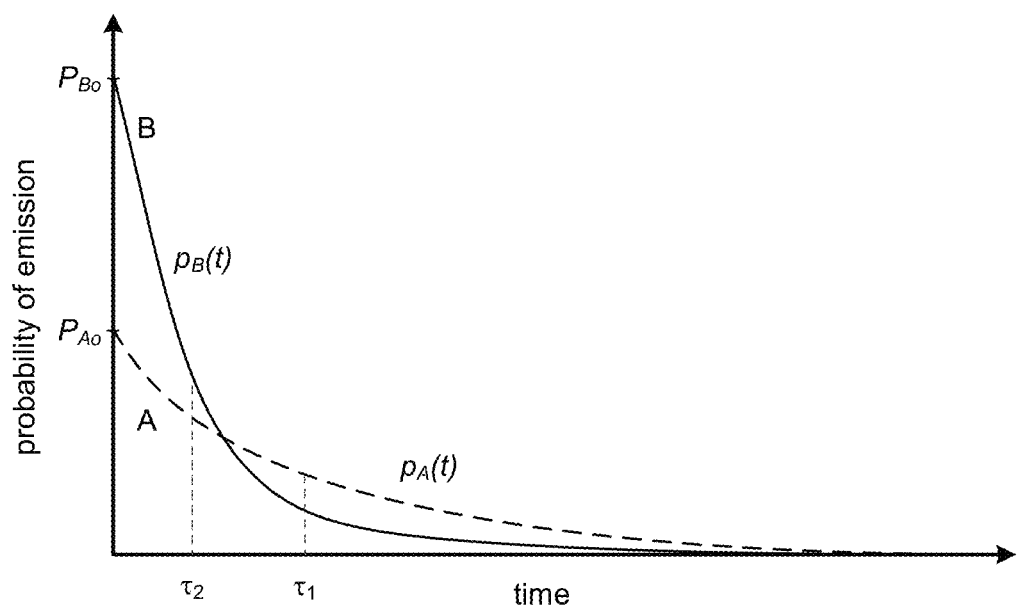
Figures 3, 4:
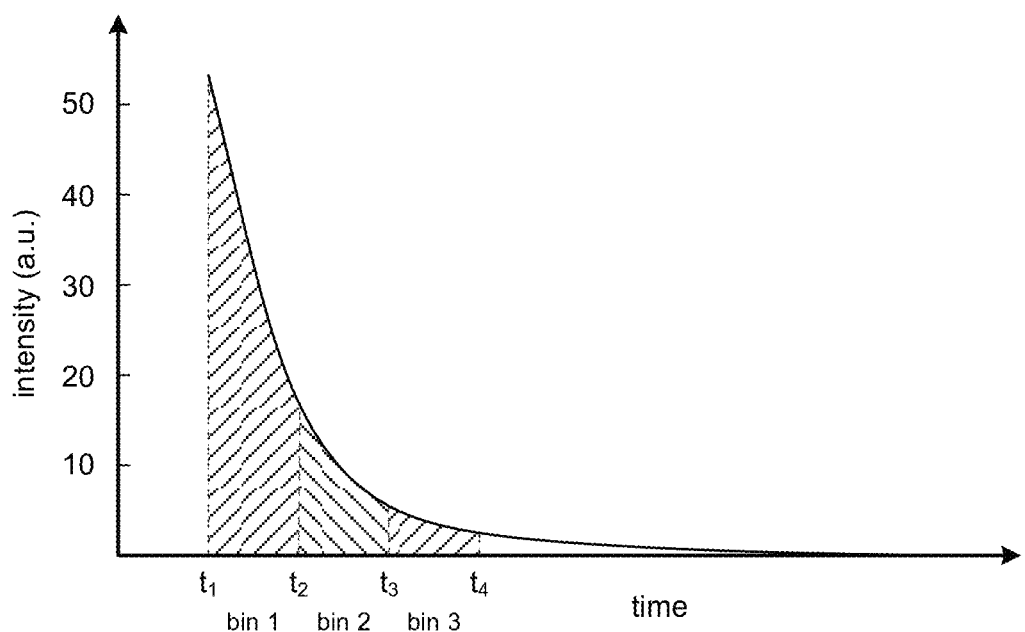
Figure 4:
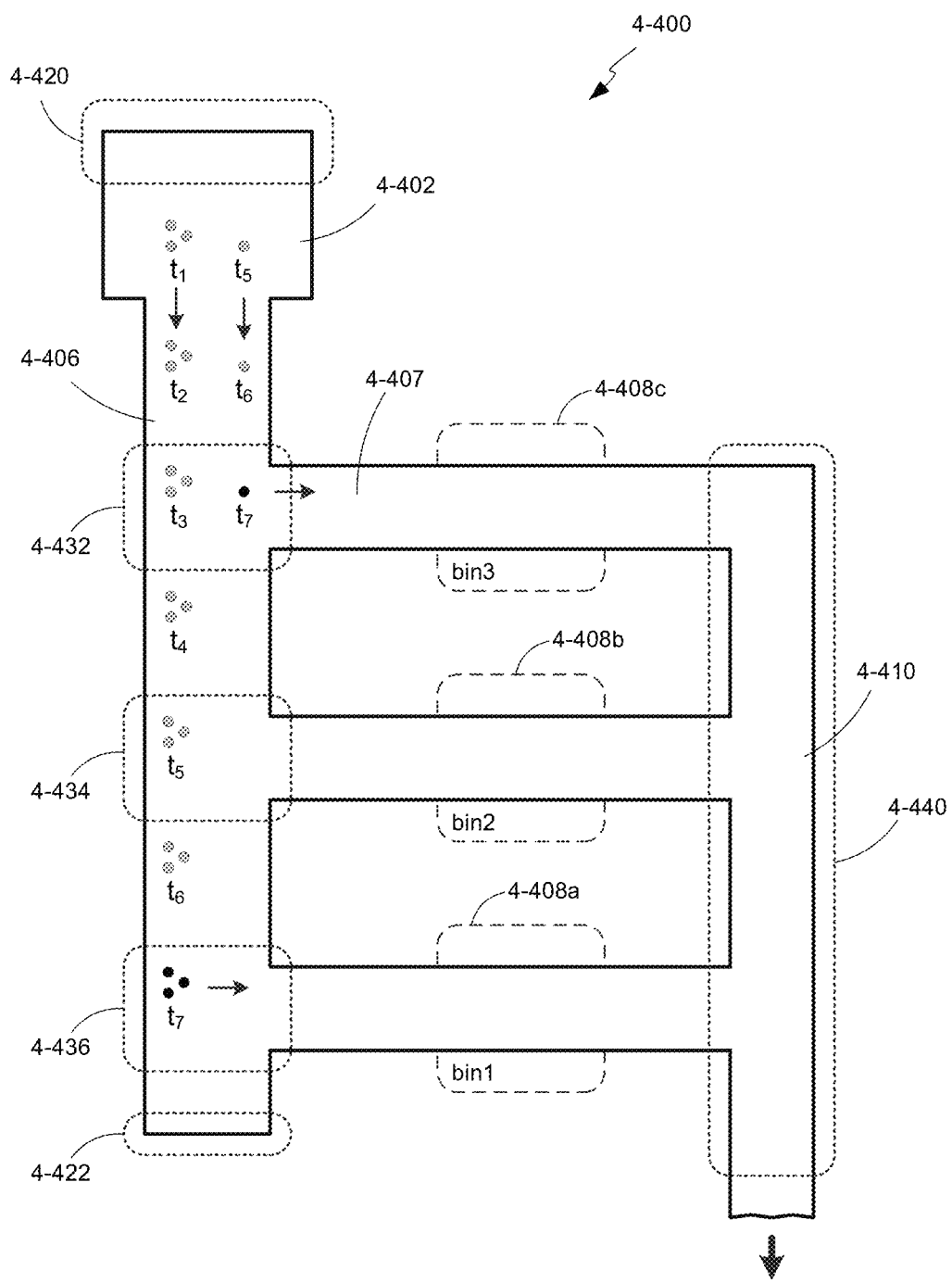
Figures 4, 5, 5A:
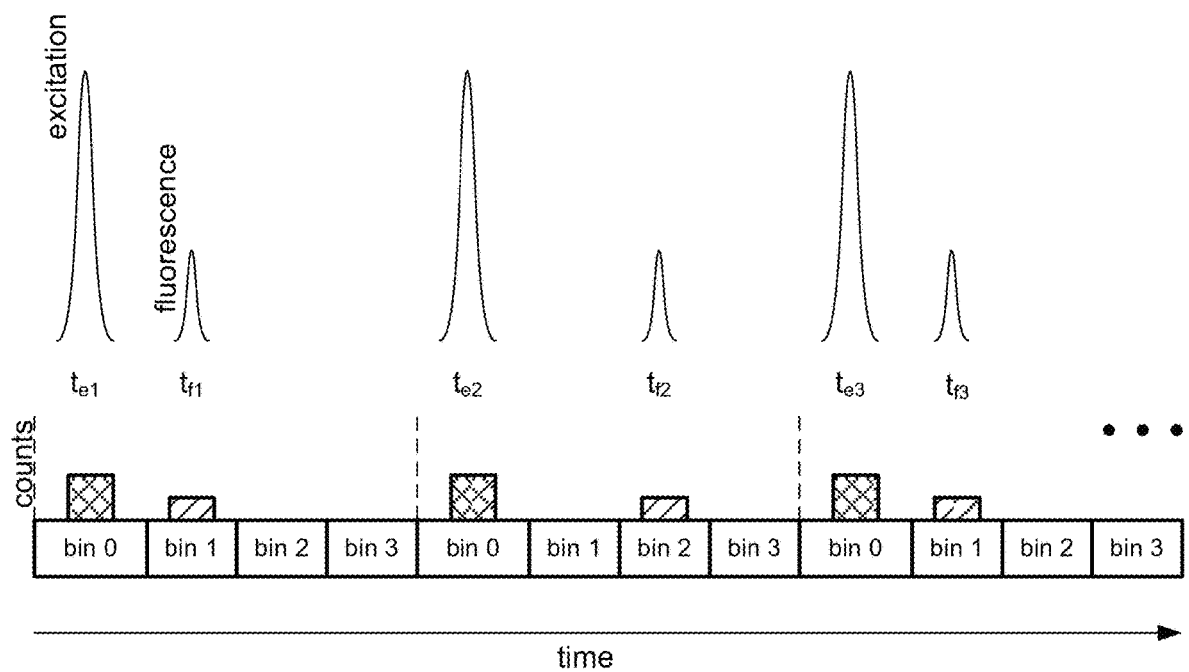
Figures 4, 5, 5B:
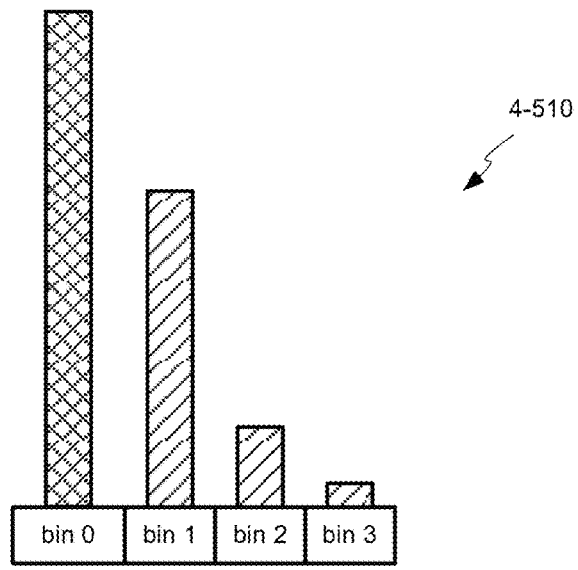

As an example of distinguishing different fluorescent molecules, a photodetector having three time bins, as depicted in FIG. 4-3B and FIG. 4-4, may produce three signal values (35, 9, 3.5), which are represented by the histogram for bin1-bin3 of FIG. 4-5B and correspond to curve B in FIG. 4-2. These binned signal values may have different relative and/or absolute values than binned signal values recorded from a different fluorescent molecule, such as one corresponding to curve A in FIG. 4-2, which might produce the binned values (18, 12, 8). By comparing the signal sequence of binned values against a calibration standard, it is possible to distinguish between two or more fluorescent molecules or environments that affect fluorescent lifetime. It can be beneficial that multiple different fluorescent molecules and/or environments may be distinguished based on lifetime information using a pulsed optical source operating at only a single characteristic wavelength.

According to some embodiments, an excitation bin (e.g., bin 0) may be included in at least one time-binning photodetector to record a signal level for the excitation pulse (e.g., accumulate carriers directly generated by the excitation pulse). The recorded signal level may be used to normalize fluorescent signal levels, which can be useful for distinguishing fluorescent molecules based on intensity.

In some embodiments, the signal values from the storage bins 4-408 may be used to fit an emission decay curve (e.g., a single exponential decay) and determine a detected lifetime. In some embodiments, the binned signal values may be fit to multiple exponential decays, such as double or triple exponentials. A Laguerre decomposition process may be used to analyze multiple exponential decays. In some implementations, the signal values may be treated as a vector or location and mapped to M-dimensional space, and cluster analysis may be used to determine a detected lifetime. Once a lifetime has been determined, the type of fluorescent molecule or a property of the environment in which a fluorescent molecule is located may be identified.

Although the example described in connection with FIG. 4-3 and FIG. 4-4 depicts three time bins, a time-binning photodetector may have fewer or more time bins. For example, the number of time bins may be 2, 3, 4, 5, 6, 7, 8, or more. In some cases, there may be 16, 32, 64, or more time bins. According to some embodiments, a number of time bins in a photodetector may be reconfigurable. For example, one or more adjacent bins may be combined when read-out.

Although the discussion for FIG. 4-3 relates to detecting emission from a single type of fluorescent molecule at a time, in some cases a sample may contain two or more different fluorescent molecules having different lifetimes. Where multiple different fluorescent molecules contribute to a temporal emission profile, an average fluorescence lifetime may be used to represent the ensemble. In some embodiments, an analytic system 1-160 may be configured to discern between combinations of fluorescent molecules. For example, a first combination of fluorescent molecules may exhibit a different average lifetime than a second combination of fluorescent molecules.

According to some embodiments, time-binning photodetectors may be used in an imaging array, and imaging optics may be included between the time-binning photodetector array and a sample. For example, each imaging pixel of an imaging array may comprise a time-binning photodetector 4-400. The imaging optics may form an image of a region of the sample on the photodetector array. Each pixel in the photodetector array may record time-binned signal values that are analyzed to determine a fluorescent lifetime for the portion of the imaged region corresponding to the pixel. Accordingly, such an imaging array can provide spatially resolved fluorescent lifetime imaging information to discern different regions in an image having different fluorescent lifetime characteristics. In some implementations, the same time-binning photodetectors may be used to obtain a conventional image of the same region, e.g., by summing all bins at each pixel or by constructing an image from the excitation pulse bin (bin0). Fluorescent lifetime variations may be displayed as an overlapping color-coded map on a conventional gray-scale or color image. In some cases, the lifetime mapping may enable a physician performing a procedure to identify an abnormal or diseased region of tissue (e.g., cancerous or pre-cancerous).

The inventors have recognized and appreciated that compact, pulsed optical sources and time-binning photodetectors for detecting fluorescent lifetimes may be combined in low-cost, portable, point-of-care (POC) instruments that can have applications in clinical settings or at-home settings. Such instruments may be imaging or non-imaging, and may utilize fluorescent lifetime analysis to determine one or more properties of a biological sample (e.g., human tissue). In some cases, an instrument 4-100 for determining properties of biological samples may be used in the field for analyzing biological substances (e.g., for analyzing potentially hazardous material). Some aspects of POC instruments and sample analysis using fluorescent lifetimes are described below.

The inventors have recognized and appreciated that some endogenous biological molecules fluoresce with signature lifetimes that may be analyzed to determine a patient's condition or a condition of a patient's tissue or organ. Accordingly, some native biological molecules may serve as endogenous fluorescent molecules for a region of a patient, and provide label-free reporters for that region of the patient. Examples of endogenous fluorescent molecules may include hemoglobin, collagen, nicotinamide adenine dinucleotide phosphate (NAD(P)H), retinol, riboflavin, cholecalciferol, folic acid, pyridoxine, tyrosine, dityrosine, glycation adduct, idolamine, lipofuscin, polyphenol, tryptophan, flavin, and melanin, by way of example and not limitation.

Endogenous fluorescent molecules may vary in the wavelength of light they emit and their response to excitation energy. Wavelengths of excitation and fluorescence for some exemplary endogenous fluorescent molecules are provided in Table 1. Additional endogenous fluorescent molecules and their characteristic fluorescent wavelengths include: retinol—500 nm, riboflavin—550 nm, cholecalciferol—380-460 nm, and pyridoxine—400 nm.

TABLE 1

Endogenous Fluorescent Molecules

| Molecule | Excitation (nm) | Fluorescence (nm) |
|---|---|---|
| NAD(P)H | 340 | 450 |
| Collagen | 270-370 | 305-450 |
| Tyrosine | 270 | 305 |
| Dityrosine | 325 | 400 |
| Excimer-like aggregate | 270 | 360 |
| Glycation adduct | 370 | 450 |
| Tryptophan | 280 | 300-350 |
| Falvin | 380-490 | 520-560 |
| Melanin | 340-400 | 360-560 |

Endogenous fluorescent molecules may also have different fluorescent lifetimes and/or fluorescent lifetimes that are sensitive to a surrounding environment. Environmental factors that may affect fluorescent lifetimes of endogenous fluorescent molecules include, changes in tissue architecture, morphology, oxygenation, pH, vascularity, cell structure and/or cell metabolic state. In some embodiment, a fluorescent lifetime (or average of combined lifetimes) for a healthy tissue may be different than for an unhealthy tissue. Analyzing fluorescent lifetimes detected from a patient's tissue that has been illuminated with a short or ultrashort optical pulse may allow a clinician to detect an earlier stage of a disease in the patient than other assessment techniques. For example, some types of skin cancer may be detected at an early stage using fluorescent lifetime analysis before the cancer is visible to the unaided eye.

In some embodiments, the presence and/or relative concentrations of certain biological molecules may be detected to determine a patient's condition. For some biological molecules, the oxidation state of the molecule may provide an indication of the patient's condition. A fluorescent lifetime for the molecule may be altered based upon an oxidation state of the molecule. Analysis of detected fluorescent lifetimes may be used to determine the relative concentrations of an oxidized state and a reduced state of a biological molecule in the tissue of a patient. The relative concentrations may indicate a condition of the patient. In some cases, some biological molecules (e.g., NADH) may bind to other molecules (e.g., proteins) in a cell as well as have an unbound or free solution state. The bound and unbound states may have different fluorescent lifetimes. Assessment of a cell or tissue may include determining relative concentrations of molecules in free versus bound forms based upon fluorescent lifetimes.

Certain biological molecules may provide an indication of a variety of diseases and conditions including cancer (e.g., melanoma), tumors, bacterial infection, virial infection, and diabetes. As an example, cancerous cells and tissues may be differentiated from healthy cells and tissues by analyzing fluorescent lifetimes from certain biological molecules (e.g., NAD(P)H, riboflavin, flavin). A cancerous tissue may have a higher concentration of one or more of these biological molecules than a healthy tissue. As another example, diabetes in individuals may be assessed by detecting fluorescent lifetimes associated with biological molecules that are indicative of glucose concentration, such as hexokinase and glycogen adduct. As another example, general changes due to aging may be assessed by detecting concentrations of collagen and lipofuscin based on fluorescent lifetimes.

In some embodiments, exogenous fluorescent molecules may be incorporated into a region of tissue, and be used alternatively, or in addition to, endogenous fluorescent molecules. In some cases, exogenous fluorescent markers may be included with a probe or provided as a marker to identify the presence of a target (e.g., a particular molecule, bacteria, or virus) in the sample. Examples of exogenous fluorescent molecules include fluorescent stains, organic dyes, fluorescent proteins, enzymes, and/or quantum dots. Such exogenous molecules may be conjugated to a probe or functional group (e.g., molecule, ion, and/or ligand) that specifically binds to a particular target or component suspected to be present in the sample. Attaching an exogenous fluorescent molecule to a probe may allow the identification of the target by detecting a fluorescent lifetime indicative of the exogenous fluorescent molecule. In some embodiments, exogenous fluorescent molecules may be included in a composition (e.g., gel or liquid) that can be easily applied to a patient (e.g., topical application to skin, ingestion for gastrointestinal tract imaging).

As may be appreciated, a compact, POC imaging instrument may allow a clinician to evaluate and/or diagnose a patient's condition in a non-invasive manner. By imaging an accessible region of tissue with an imaging device rather than by extracting a biological sample from a patient, assessments of the patient may be performed in a manner that reduces the amount of time involved in obtaining results, reduces the invasiveness of a procedure, reduces the cost, and/or facilitates the ability of clinicians to treat patients without moving the patient to a remote testing location or sending a sample of a patient to a testing facility.

Another application for time-domain, fluorescent lifetime imaging is in the area of microscopy. Fluorescence lifetime imaging microscopy (FLIM) may be performed by exciting a sample viewed microscopically with a short or ultrashort optical pulse, and detecting the fluorescence from the sample with a time-binning photodetector array. The detected fluorescence may be analyzed at the pixel level to determine lifetimes for corresponding imaged portions within the field of view of the microscope, and lifetime data may be mapped to a resulting image of the sample. Accordingly, sample properties may be determined at the microscopic level based on fluorescent lifetimes.

Pulsed optical sources and time-binning photodetector arrays may also be used in time-domain applications that do not involve fluorescent lifetime analysis. One such application includes time-of-flight (TOF) imaging. In TOF imaging, optical pulses may be used to illuminate a distant object. Imaging optics may be used to collect backscattered radiation from the pulses and form an image of the distant object on a time-binning photodetector array. At each pixel in the array, the arrival time of photons may be determined (e.g., determining when a peak of a backscattered pulse occurs). Since the arrival time is proportional to the distance between the object and the photodetector array, a three-dimensional map of the object may be created that shows surface topography of the imaged object.

V. Configurations

Various configurations and embodiments of the apparatus and methods may be implemented. Some example configurations are described in this section, but the invention is not limited to only the listed configurations and embodiments.

(1) A pulsed optical source comprising a semiconductor diode configured to emit light, and a driving circuit that includes a transistor coupled to a terminal of the semiconductor diode, wherein the driving circuit is configured to receive a unipolar pulse and apply a bipolar electrical pulse to the semiconductor diode responsive to receiving the unipolar pulse.

(2) The pulsed optical source of configuration (1), wherein the bipolar electrical pulse comprises a first pulse having a first magnitude and first polarity that is followed by a second pulse of opposite polarity having a second magnitude different from the first magnitude.

(3) The pulsed optical source of (2), wherein the second magnitude is between 25% and 90% of the first magnitude.

(4) The pulsed optical source of any one of (1)-(3), further comprising multiple wire bonds connected to a terminal of the semiconductor diode.

(5) The pulsed optical source of any one of (1)-(4), further comprising a pulse generator coupled to the driving circuit and configured to form the unipolar pulse and output the unipolar pulse to the driving circuit.

(6) The pulsed optical source of (5), wherein the pulse generator, driving circuit, and semiconductor diode are located on a same printed circuit board.

(7) The pulsed optical source of (5), wherein the pulse generator, driving circuit, and semiconductor diode are located on a same substrate.

(8) The pulsed optical source of any one of (1)-(7), wherein a pulse length of the unipolar pulse is between 50 ps and 500 ps.

(9) The pulsed optical source of any one of (5)-(8), wherein the pulse generator comprises a first logic gate that forms the unipolar pulse from two differential clock signals.

(10) The pulsed optical source of (9), wherein the first logic gate comprises an emitter-coupled logic gate.

(11) The pulsed optical source of (9) or (10), wherein the pulse generator further comprises a fan-out gate configured to receive a single clock signal and output four clock signals to the first logic gate.

(12) The pulsed optical source of any one of (9)-(11), wherein the pulse generator further comprises an adjustable delay element configured to vary a pulse length of the unipolar pulse in increments between 1 ps and 5 ps.

(13) The pulsed optical source of any one of (9)-(12), wherein the transistor has current-carrying terminals connected between a cathode of the semiconductor diode and a reference potential and has a gate terminal coupled to the first logic gate.

(14) The pulsed optical source of (13), further comprising a capacitor connected between the gate terminal of the transistor and an output from the first logic gate.

(15) The pulsed optical source of any one of (1)-(14), wherein the transistor comprises a high-electron-mobility field-effect transistor.

(16) The pulsed optical source of any one of (1)-(15), wherein the transistor is configured to switch up to 4 amps through the semiconductor diode for a duration between 50 ps and 2 ns.

(17) The pulsed optical source of any one of (9)-(13), further comprising a second logic gate connected in parallel with the first logic gate and arranged to form a second unipolar pulse from the two differential clock signals, wherein an output from the second logic gate is coupled to the gate terminal of the transistor.

(18) The pulsed optical source of any one of (1)-(17), wherein a drain terminal of the transistor connects directly to a cathode of the semiconductor diode.

(19) The pulsed optical source of (18), further comprising a first capacitor and resistor connected in parallel to the drain terminal.

(20) The pulsed optical source of (18) or (19), further comprising a second capacitor connected between an anode of the semiconductor diode and a source terminal of the transistor.

(21) The pulsed optical source of any one of (5)-(20), wherein the pulse generator and driving circuit are configured to modulate the semiconductor diode with the bipolar electrical pulse at a repetition rate of between about 30 Hz and about 200 MHz.

(22) The pulsed optical source of any one of (1)-(21), wherein an optical pulse having a full-width-half maximum duration between 50 ps and 500 ps is emitted from the semiconductor diode responsive to application of the bipolar electrical pulse.

(23) The pulsed optical source of any one of (1)-(21), wherein the optical pulse has a characteristic wavelength selected from the following group: 270 nm, 280 nm, 325 nm, 340 nm, 370 nm, 380 nm, 400 nm, 405 nm, 410 nm, 450 nm, 465 nm, 470 nm, 490 nm, 515 nm, 640 nm, 665 nm, 808 nm, and 980 nm.

(24) The pulsed optical source of any one of (1)-(23), wherein a tail of the optical pulse remains below at least 20 dB from the peak of the pulse after 250 ps from the peak of the pulse.

(25) The pulsed optical source of any one of (1)-(24), wherein the semiconductor diode comprises a laser diode.

(26) The pulsed optical source of (25), wherein the laser diode includes multiple quantum wells.

(27) The pulsed optical source of any one of (1)-(26), wherein the semiconductor diode is a light-emitting diode.

(28) The pulsed optical source of any one of (1)-(27), wherein the semiconductor diode is a slab-coupled optical waveguide laser diode.

(29) The pulsed optical source of any one of (1)-(28), further comprising a saturable absorber arranged to receive an optical pulse from the semiconductor diode.

(30) The pulsed optical source of any one of (1)-(29), wherein the saturable absorber is formed in a same substrate as the semiconductor diode.

(31) The pulsed optical source of any one of (1)-(4), (15), (16), (18), and (22)-(30), wherein the driving circuit comprises a transmission line pulse generator.

(32) The pulsed optical source of (31), further comprising a transmission line that is formed in a U shape.

(33) The pulsed optical source of claim (31) or (32), wherein the semiconductor diode is connected to a first end of the transmission line and further comprising a terminating impedance that is connected to a second end of the transmission line.

(34) The pulsed optical source of claim (33), further comprising a shorting transistor that is arranged to short the first end and second end of the transmission line to a reference potential.

(35) The pulsed optical source of any one of (1)-(34), further comprising a photodetector array having a plurality of pixels that are each configured to discriminate photon arrival times into at least two time bins during a single charge-accumulation interval, and an optical system arranged to form an image of an object, that is illuminated by the pulsed optical source, on the photodetector array.

(36) The pulsed optical source of (35), wherein the photodetector array is arranged to produce signals representative of fluorescent lifetime of at least one fluorescent molecule located at the distant object.

(37) The pulsed optical source of (35) or (36), further comprising signal processing electronics that are configured to receive the signals representative of fluorescent lifetime from the photodetector array and generate digital data for an electronic image of the object, wherein the electronic image indicates at least one characteristic of the object based on fluorescent lifetime.

(38) A method of producing an optical pulse, the method comprising acts of receiving at least one clock signal, producing an electrical pulse from the at least one clock signal, driving a gate terminal of a transistor with the electrical pulse, wherein a current carrying terminal of the transistor is connected to a semiconductor diode that is configured to emit light, and applying a bipolar current pulse to the semiconductor diode to produce an optical pulse responsive to activation of the transistor by the electrical pulse.

(39) The method of embodiment (38), wherein the electrical pulse is a unipolar pulse.

(40) The method of (38) or (39), further comprising adjusting a pulse duration and not a pulse amplitude of the unipolar pulse to control an amplitude of the optical pulse.

(41) The method of any one of (38)-(40), wherein the optical pulse has a full-width-half-maximum duration between 50 ps and 2 ns.

(42) The method of any one of (38)-(40), wherein the optical pulse has a full-width-half-maximum duration between 50 ps and 500 ps.

(43) The method of any one of (38)-(42), wherein the optical pulse has a characteristic wavelength selected from the following group: 270 nm, 280 nm, 325 nm, 340 nm, 370 nm, 380 nm, 400 nm, 405 nm, 410 nm, 450 nm, 465 nm, 470 nm, 490 nm, 515 nm, 640 nm, 665 nm, 808 nm, and 980 nm.

(44) The method of any one of (38)-(43), further comprising repeating the acts of receiving, producing, driving, and applying to produce a series of optical pulses at a repetition rate between 30 Hz and 200 MHz.

(45) The method of any one of (38)-(44), wherein the bipolar current pulse comprises a first pulse having a first amplitude and a second pulse having a second amplitude of opposite polarity and different magnitude from the first pulse.

(46) The method of (38)-(45), wherein the semiconductor diode comprises a laser diode or light-emitting diode.

(47) The method of any one of (38)-(46), further comprising differentially attenuating a portion of the optical pulse with a saturable absorber.

(48) The method of any one of (38)-(47), wherein the act of receiving at least one clock signal comprises receiving two differential clock signals at a logic gate coupled to the gate terminal of the transistor.

(49) The method of any one of (38)-(47), wherein the act of receiving at least one clock signal comprises receiving two differential clock signals at two logic gates coupled in parallel the gate terminal of the transistor.

(50) The method of any one of (38)-(49), wherein the act of producing the electrical pulse comprises processing two differential clock signals with a logic gate coupled to the gate terminal of the transistor to form the electrical pulse.

(51) The method of (50), further comprising setting a length of the electrical pulse by a phase delay between the two differential clock signals.

(52) The method of any one of (38)-(51), wherein the act of producing the electrical pulse comprises processing two differential clock signals with two logic gates coupled in parallel to the gate terminal of the transistor to form the electrical pulse.

(53) The method of any one of (38)-(52), further comprising illuminating a sample with optical pulses from the semiconductor diode, and detecting fluorescent lifetimes from the sample.

(54) The method of (53), further comprising distinguishing between at least two different fluorescent lifetimes having different decay rates associated with two different fluorescent molecules or environments in which the molecules are located, wherein the optical pulses are at a single characteristic wavelength.

(55) The method of (53) or (54), further comprising determining at least one property of the sample based on the detected fluorescent lifetimes.

(56) The method of (55), further comprising producing an electronic image of a region of the sample, and indicating the at least one characteristic that is based on fluorescent lifetime in the image.

(57) The method of any one of (38)-(52), further comprising illuminating a sample with optical pulses from the semiconductor diode, and discriminating arrival times of photons scattered back from the sample into at least two time bins with a single photodetector during a single charge accumulation interval for the single photodetector.

(58) The method of (57), further comprising producing an electronic, three-dimensional image of the sample based upon the discriminated arrival times.

(59) A fluorescent lifetime analysis system comprising a semiconductor diode configured to emit light, a driving circuit configured to apply a bipolar current pulse to the semiconductor diode to produce an optical pulse, an optical system arranged to deliver the optical pulse to a sample, and a photodetector configured to discriminate photon arrival times into at least two time bins during a single charge-accumulation interval of the photodetector.

(60) The system of (59), further comprising a pulse generator arranged to provide an electrical pulse to the current driving circuit, wherein the current driving circuit is configured to apply a bipolar pulse to the semiconductor diode responsive to receiving the electrical pulse.

(61) The system of (60), wherein the electrical pulse is a unipolar pulse having a duration between 50 ps and 2 ns.

(62) The system of (60) or (61), wherein the current driving circuit comprises a transistor having a gate terminal coupled to an output from the pulse generator and having current-carrying terminals connected between a terminal of the semiconductor diode and a reference potential.

(63) The system of (62), further comprising a first resistor and first capacitor connected in parallel between an anode and a cathode of the semiconductor diode, and a second resistor and second capacitor connected in parallel between a gate terminal of the transistor and a reference potential.

(64) The system of any one of (59)-(63), wherein the semiconductor diode comprises a laser diode or light-emitting diode.

(65) The system of any one of (59)-(63), further comprising multiple wire bonds connected to a terminal of the semiconductor diode.

(66) The system of any one of (59)-(63), wherein the optical pulse has a full-width-half-maximum duration between 50 ps and 500 ps.

(67) The system of any one of (59)-(63), wherein the optical pulse has a characteristic wavelength selected from the following group: 270 nm, 280 nm, 325 nm, 340 nm, 370 nm, 380 nm, 400 nm, 405 nm, 410 nm, 450 nm, 465 nm, 470 nm, 490 nm, 515 nm, 640 nm, 665 nm, 808 nm, and 980 nm.

(68) The system of any one of (59)-(63), further comprising an array of photodetectors in which the photodetector is located, the array of photodetectors configured to time-bin fluorescence from the sample during a single charge-accumulation interval for the optical pulse.

(69) The system of (68), further comprising imaging optics located between the sample and the photodetector array, wherein the imaging optics are arranged to form an image at the photodetector array of a region of the sample illuminated by the optical pulse.

(70) The system of (69), wherein the image formed at the photodetector array is an image of a microscopic region of the sample.

(71) A pulsed optical source comprising a semiconductor diode configured to emit light, a first logic gate configured to form a first pulse at an output of the first logic gate, a driving circuit coupled to the first logic gate, wherein the driving circuit is configured to receive the first pulse and apply a bipolar electrical pulse to the semiconductor diode to produce an optical pulse responsive to receiving the first pulse.

(72) The pulsed optical source of (71), wherein the first pulse is a unipolar pulse.

(73) The pulsed optical source of (72), further comprising a fan-out gate and a delay element coupled to the first logic gate, wherein the delay element delays at least one output from the fan-out gate.

(74) The pulsed optical source of (73), wherein the delay element is configured to vary a pulse length of the unipolar pulse in increments between 1 ps and 5 ps.

(75) The pulsed optical source of any one of (71)-(74), wherein the first logic gate is configured to form the first pulse from two differential clock signals.

(76) The pulsed optical source of any one of (71)-(75), wherein the bipolar electrical pulse comprises a first pulse having a first magnitude and first polarity that is followed by a second pulse of opposite polarity having a second magnitude different from the first magnitude.

(77) The pulsed optical source of (76), wherein the second magnitude is between 25% and 90% of the first magnitude.

(78) The pulsed optical source of any one of (71)-(77), further comprising multiple wire bonds connected to a terminal of the semiconductor diode.

(79) The pulsed optical source of any one of (75)-(78), further comprising a second logic gate configured to form a second pulse from the two differential clock signals, wherein the second logic gate is connected in parallel with the first logic gate and an output of the second logic gate is coupled to the driving circuit.

(80) The pulsed optical source of any one of (71)-(79), further comprising a transistor within the driving circuit having current carrying terminals connected between the semiconductor diode and a reference potential.

(81) The pulsed optical source of (80), wherein the optical pulse has a duration between 50 ps and 2 ns.

(82) A pulsed optical source comprising a semiconductor diode configured to emit light, and a driving circuit that includes a transistor coupled to a terminal of the semiconductor diode, wherein the driving circuit is configured to receive a unipolar pulse and apply a bipolar electrical pulse to the semiconductor diode responsive to receiving the unipolar pulse, wherein the transistor is connected in parallel with the semiconductor diode between a current source and a reference potential.

(83) The pulsed optical source of (82) optionally having features of any one of (2)-(4), (15), and (22)-(30), excluding features of (1), further comprising a resistor and a capacitor connected in parallel between the semiconductor diode and the reference potential.

(84) The pulsed optical source of (82) or (83), wherein the transistor is configured to be normally conducting and is pulsed off with the unipolar pulse.

(85) The pulsed optical source of any one of (82)-(84), further comprising a photodetector array having a plurality of pixels that are each configured to discriminate photon arrival times into at least two time bins during a single charge-accumulation interval, and an optical system arranged to form an image of an object, that is illuminated by the pulsed optical source, on the photodetector array.

(86) A pulsed optical source comprising a semiconductor diode configured to emit light, and plural first circuit branches connected to a first terminal of the semiconductor diode, each circuit branch comprising a transistor having its current-carrying terminals connected between a reference potential and the first terminal of the semiconductor diode.

(87) The pulsed optical source of (86) optionally having features of any one of (4), (15), (16) and (22)-(30), excluding features of (1), wherein a first reference potential in a first circuit branch of the plural first circuit branches has a different value from a second reference potential in a second circuit branch of the plural first circuit branches.

(88) The pulsed optical source of (86) or (87), wherein a first reference potential in a first circuit branch of the plural first circuit branches has a positive value and a second reference potential in a second circuit branch of the plural first circuit branches has a negative value.

(89) The pulsed optical source of any one of (86)-(88), further comprising in each circuit branch a resistor connected between a current-carrying terminal of the transistor and the reference potential.

(90) The pulsed optical source of any one of (86)-(89), further comprising in each circuit branch a capacitor connected between a current-carrying terminal of the transistor and a ground potential.

(91) The pulsed optical source of any one of (86)-(90), further comprising a photodetector array having a plurality of pixels that are each configured to discriminate photon arrival times into at least two time bins during a single charge-accumulation interval, and an optical system arranged to form an image of an object, that is illuminated by the pulsed optical source, on the photodetector array.

(92) A pulsed optical source comprising a radio-frequency amplifier providing a signal and an inverted signal, a logic gate configured to receive the signal and a phase-shifted inverted signal and output a pulse and an inverted pulse, a combiner configured to combine the pulse and inverted pulse onto a common output, and a semiconductor diode coupled to the common output and configured to produce an optical pulse responsive to receiving the pulse and inverted pulse.

(93) The pulsed optical source of (92) optionally having features of any one of (4), (15), (16) and (22)-(30), excluding features of (1), further comprising a variable attenuator arranged to attenuate the pulse or the inverted pulse.

(94) The pulsed optical source of (92) or (93), further comprising a delay element arranged to temporally delay the pulse or the inverted pulse.

(95) The pulsed optical source of any one of (92)-(94), further comprising a DC block connect to an input of the radio-frequency amplifier.

(96) The pulsed optical source of any one of (92)-(95), further comprising a photodetector array having a plurality of pixels that are each configured to discriminate photon arrival times into at least two time bins during a single charge-accumulation interval, and an optical system arranged to form an image of an object, that is illuminated by the pulsed optical source, on the photodetector array.

(97) A pulsed optical source comprising a radio-frequency logic gate configured to receive a first signal and an inverted version of the first signal and output a pulse and an inverted version of the pulse, and a semiconductor diode connect to the radio-frequency logic gate and arranged to receive the pulse at a first terminal of the semiconductor diode and the inverted version of the pulse at a second terminal of the semiconductor diode and emit an optical pulse.

(98) The pulsed optical source of (97) optionally having features of any one of (4), (15), (16) and (22)-(30), excluding features of (1), further comprising a first amplifier arranged to receive a periodic signal and output the first signal and the inverted version of the first signal, and a phase shifter arranged to vary a phase of the first signal or the inverted version of the first signal.

(99) The pulsed optical source of (97) or (98), further comprising a photodetector array having a plurality of pixels that are each configured to discriminate photon arrival times into at least two time bins during a single charge-accumulation interval, and an optical system arranged to form an image of an object, that is illuminated by the pulsed optical source, on the photodetector array.

VI. Conclusion

Having thus described several aspects of several embodiments of a pulsed laser, it is to be appreciated that various alterations, modifications, and improvements will readily occur to those skilled in the art. Such alterations, modifications, and improvements are intended to be part of this disclosure, and are intended to be within the spirit and scope of the invention. While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art.

While various inventive embodiments have been described and illustrated, those of ordinary skill in the art will readily envision a variety of other means and/or structures for performing the function and/or obtaining the results and/or one or more of the advantages described, and each of such variations and/or modifications is deemed to be within the scope of the inventive embodiments described. More generally, those skilled in the art will readily appreciate that all parameters, dimensions, materials, and configurations described are meant to be examples and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure may be directed to each individual feature, system, system upgrade, and/or method described. In addition, any combination of two or more such features, systems, and/or methods, if such features, systems, system upgrade, and/or methods are not mutually inconsistent, is included within the inventive scope of the present disclosure.

Further, though some advantages of the present invention may be indicated, it should be appreciated that not every embodiment of the invention will include every described advantage. Some embodiments may not implement any features described as advantageous. Accordingly, the foregoing description and drawings are by way of example only.

Numerical values and ranges may be described in the specification and claims as approximate or exact values or ranges. For example, in some cases the terms "about," "approximately," and "substantially" may be used in reference to a value. Such references are intended to encompass the referenced value as well as plus and minus reasonable variations of the value. For example, a phrase "between about 10 and about 20" is intended to mean "between exactly 10 and exactly 20" in some embodiments, as well as "between 10±δ1 and 20±δ2" in some embodiments. The amount of variation δ1, δ2 for a value may be less than 5% of the value in some embodiments, less than 10% of the value in some embodiments, and yet less than 20% of the value in some embodiments. In embodiments where a large range of values is given, e.g., a range including two or more orders of magnitude, the amount of variation δ1, δ2 for a value could be as high as 50%. For example, if an operable range extends from 2 to 200, "approximately 80" may encompass values between 40 and 120 and the range may be as large as between 1 and 300. When exact values are intended, the term "exactly" is used, e.g., "between exactly 2 and exactly 200."

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

The section headings used are for organizational purposes only and are not to be construed as limiting the subject matter described in any way.

Also, the technology described may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used, should be understood to control over dictionary definitions, definitions in documents incorporated by reference, and/or ordinary meanings of the defined terms.

The indefinite articles "a" and "an," as used in the specification and in the claims, unless clearly indicated to the contrary, should be understood to mean "at least one."

The phrase "and/or," as used in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

The claims should not be read as limited to the described order or elements unless stated to that effect. It should be understood that various changes in form and detail may be made by one of ordinary skill in the art without departing from the spirit and scope of the appended claims. All embodiments that come within the spirit and scope of the following claims and equivalents thereto are claimed.

What is claimed is:

1. A pulsed optical source comprising:
   a semiconductor diode configured to emit light; and
   a driving circuit that includes a transistor coupled to a terminal of the semiconductor diode, wherein the driving circuit is configured to receive a unipolar pulse and apply a bipolar electrical pulse to the semiconductor diode responsive to receiving the unipolar pulse, wherein an optical pulse having a full-width-half maximum duration between 50 ps and 500 ps is emitted from the semiconductor diode responsive to application of the bipolar electrical pulse.

2. The pulsed optical source of claim 1, wherein the bipolar electrical pulse comprises a first pulse having a first magnitude and first polarity that is followed by a second pulse of opposite polarity having a second magnitude different from the first magnitude.

3. The pulsed optical source of claim 2, wherein the second magnitude is between 25% and 90% of the first magnitude.

4. The pulsed optical source of claim 1, further comprising multiple wire bonds connected to a terminal of the semiconductor diode.

5. The pulsed optical source of claim 1, further comprising a pulse generator coupled to the driving circuit and configured to form the unipolar pulse and output the unipolar pulse to the driving circuit.

6. The pulsed optical source of claim 5, wherein the pulse generator, driving circuit, and semiconductor diode are located on a same printed circuit board.

7. The pulsed optical source of claim 5, wherein the pulse generator, driving circuit, and semiconductor diode are located on a same substrate.

8. The pulsed optical source of claim 5, wherein a pulse length of the unipolar pulse is between 50 ps and 500 ps.

9. The pulsed optical source of claim 5, wherein the pulse generator comprises a first logic gate that forms the unipolar pulse from two differential clock signals.

10. The pulsed optical source of claim 9, wherein the first logic gate comprises an emitter-coupled logic gate.

11. The pulsed optical source of claim 9, wherein the pulse generator further comprises a fan-out gate configured to receive a single clock signal and output four clock signals to the first logic gate.

12. The pulsed optical source of claim 9, wherein the pulse generator further comprises an adjustable delay element configured to vary a pulse length of the unipolar pulse in increments between 1 ps and 5 ps.

13. The pulsed optical source of claim 5, wherein the pulse generator and driving circuit are configured to modulate the semiconductor diode with the bipolar electrical pulse at a repetition rate of between about 30 Hz and about 200 MHz.

14. The pulsed optical source of claim 1, wherein the optical pulse has a characteristic wavelength selected from the following group: 270 nm, 280 nm, 325 nm, 340 nm, 370 nm, 380 nm, 400 nm, 405 nm, 410 nm, 450 nm, 465 nm, 470 nm, 490 nm, 515 nm, 640 nm, 665 nm, 808 nm, and 980 nm.

15. The pulsed optical source of claim 1, wherein a tail of the optical pulse remains below at least 20 dB from the peak of the pulse after 250 ps from the peak of the pulse.

16. The pulsed optical source of claim 1, wherein the semiconductor diode comprises a laser diode.

17. The pulsed optical source of claim 16, wherein the laser diode includes multiple quantum wells.

18. The pulsed optical source of claim 1, wherein the semiconductor diode is a light-emitting diode.

19. The pulsed optical source of claim 1, wherein the semiconductor diode is a slab-coupled optical waveguide laser diode.

20. The pulsed optical source of claim 1, further comprising a saturable absorber arranged to receive an optical pulse from the semiconductor diode.

21. The pulsed optical source of claim 20, wherein the saturable absorber is formed in a same substrate as the semiconductor diode.

22. The pulsed optical source of claim 1, further comprising:
a photodetector array having a plurality of pixels that are each configured to discriminate photon arrival times into at least two time bins during a single charge-accumulation interval; and
an optical system arranged to form an image of an object, that is illuminated by the pulsed optical source, on the photodetector array.

23. The pulsed optical source of claim 22, wherein the photodetector array is arranged to produce signals representative of fluorescent lifetime of at least one fluorescent molecule located at the distant object.

24. The pulsed optical source of claim 23, further comprising signal processing electronics that are configured to receive the signals representative of fluorescent lifetime from the photodetector array and generate digital data for an electronic image of the object, wherein the electronic image indicates at least one characteristic of the object based on fluorescent lifetime.

25. The pulsed optical source of claim 9, wherein the transistor has current-carrying terminals connected between a cathode of the semiconductor diode and a reference potential and has a gate terminal coupled to the first logic gate.

26. The pulsed optical source of claim 25, further comprising a capacitor connected between the gate terminal of the transistor and an output from the first logic gate.

27. The pulsed optical source of claim 25, wherein the transistor comprises a high-electron-mobility field-effect transistor.

28. The pulsed optical source of claim 25, wherein the transistor is configured to switch up to 4 amps through the semiconductor diode for a duration between 50 ps and 2 ns.

29. The pulsed optical source of claim 25, further comprising a second logic gate connected in parallel with the first logic gate and arranged to form a second unipolar pulse from the two differential clock signals, wherein an output from the second logic gate is coupled to the gate terminal of the transistor.

30. The pulsed optical source of claim 25, wherein a drain terminal of the transistor connects directly to a cathode of the semiconductor diode.

31. The pulsed optical source of claim 30, further comprising a first capacitor and resistor connected in parallel to the drain terminal.

32. The pulsed optical source of claim 30, further comprising a second capacitor connected between an anode of the semiconductor diode and a source terminal of the transistor.

33. A method of producing an optical pulse, the method comprising:
receiving at least one clock signal;
producing an electrical pulse from the at least one clock signal;
driving a gate terminal of a transistor with the electrical pulse, wherein a current carrying terminal of the transistor is connected to a semiconductor diode that is configured to emit light; and
applying a bipolar current pulse to the semiconductor diode to produce an optical pulse responsive to activation of the transistor by the electrical pulse.

34. The method of claim 33, wherein the electrical pulse is a unipolar pulse.

35. The method of claim 34, further comprising adjusting a pulse duration and not a pulse amplitude of the unipolar pulse to control an amplitude of the optical pulse.

36. The method of claim 33, wherein the optical pulse has a full-width-half-maximum duration between 50 ps and 2 ns.

37. The method of claim 33, wherein the optical pulse has a full-width-half-maximum duration between 50 ps and 500 ps.

38. The method of claim 33, wherein the optical pulse has a characteristic wavelength selected from the following group: 270 nm, 280 nm, 325 nm, 340 nm, 370 nm, 380 nm, 400 nm, 405 nm, 410 nm, 450 nm, 465 nm, 470 nm, 490 nm, 515 nm, 640 nm, 665 nm, 808 nm, and 980 nm.

39. The method of claim 33, further comprising repeating the acts of receiving, producing, driving, and applying to produce a series of optical pulses at a repetition rate between 30 Hz and 200 MHz.

40. The method of claim 33, wherein the bipolar current pulse comprises a first pulse having a first amplitude and a second pulse having a second amplitude of opposite polarity and different magnitude from the first pulse.

41. The method of claim 33, wherein the semiconductor diode comprises a laser diode or light-emitting diode.

42. The method of claim 33, further comprising differentially attenuating a portion of the optical pulse with a saturable absorber.

43. The method of claim 33, wherein the act of receiving at least one clock signal comprises receiving two differential clock signals at a logic gate coupled to the gate terminal of the transistor.

44. The method of claim 33, wherein the act of receiving at least one clock signal comprises receiving two differential clock signals at two logic gates coupled in parallel the gate terminal of the transistor.

45. The method of claim 33, wherein the act of producing the electrical pulse comprises processing two differential clock signals with a logic gate coupled to the gate terminal of the transistor to form the electrical pulse.

46. The method of claim 45, further comprising setting a length of the electrical pulse by a phase delay between the two differential clock signals.

47. The method of claim 33, wherein the act of producing the electrical pulse comprises processing two differential clock signals with two logic gates coupled in parallel to the gate terminal of the transistor to form the electrical pulse.

48. The method of claim 33, further comprising:
illuminating a sample with optical pulses from the semiconductor diode; and
detecting fluorescent lifetimes from the sample.

49. The method of claim 48, further comprising distinguishing between at least two different fluorescent lifetimes having different decay rates associated with two different fluorescent molecules or environments in which the molecules are located, wherein the optical pulses are at a single characteristic wavelength.

50. The method of claim 48, further comprising determining at least one property of the sample based on the detected fluorescent lifetimes.

51. The method of claim 50, further comprising:
producing an electronic image of a region of the sample; and
indicating the at least one characteristic that is based on fluorescent lifetime in the image.

52. The method of claim 33, further comprising:
illuminating a sample with optical pulses from the semiconductor diode; and
discriminating arrival times of photons scattered back from the sample into at least two time bins with a single photodetector during a single charge accumulation interval for the single photodetector.

53. The method of claim 52, further comprising producing an electronic, three-dimensional image of the sample based upon the discriminated arrival times.

54. A fluorescent lifetime analysis system comprising:
a semiconductor diode configured to emit light;
a driving circuit configured to apply a bipolar current pulse to the semiconductor diode to produce an optical pulse;
an optical system arranged to deliver the optical pulse to a sample; and
a photodetector configured to discriminate photon arrival times into at least two time bins during a single charge-accumulation interval of the photodetector.

55. The system of claim 54, further comprising a pulse generator arranged to provide an electrical pulse to the current driving circuit, wherein the current driving circuit is configured to apply a bipolar pulse to the semiconductor diode responsive to receiving the electrical pulse.

56. The system of claim 55, wherein the electrical pulse is a unipolar pulse having a duration between 50 ps and 2 ns.

57. The system of claim 54, wherein the semiconductor diode comprises a laser diode or light-emitting diode.

58. The system of claim 54, further comprising multiple wire bonds connected to a terminal of the semiconductor diode.

59. The system of claim 54, wherein the optical pulse has a full-width-half-maximum duration between 50 ps and 500 ps.

60. The system of claim 54, wherein the optical pulse has a characteristic wavelength selected from the following group: 270 nm, 280 nm, 325 nm, 340 nm, 370 nm, 380 nm, 400 nm, 405 nm, 410 nm, 450 nm, 465 nm, 470 nm, 490 nm, 515 nm, 640 nm, 665 nm, 808 nm, and 980 nm.

61. The system of claim 54, further comprising an array of photodetectors in which the photodetector is located, the array of photodetectors configured to time-bin fluorescence from the sample during a single charge-accumulation interval for the optical pulse.

62. The system of claim 61, further comprising imaging optics located between the sample and the photodetector array, wherein the imaging optics are arranged to form an image at the photodetector array of a region of the sample illuminated by the optical pulse.

63. The system of claim 55, wherein the current driving circuit comprises a transistor having a gate terminal coupled to an output from the pulse generator and having current-carrying terminals connected between a terminal of the semiconductor diode and a reference potential.

64. The system of claim 63, further comprising:
a first resistor and first capacitor connected in parallel between an anode and a cathode of the semiconductor diode; and
a second resistor and second capacitor connected in parallel between a gate terminal of the transistor and a reference potential.

65. The system of claim 62, wherein the image formed at the photodetector array is an image of a microscopic region of the sample.

66. A pulsed optical source comprising:
a semiconductor diode configured to emit light;
a driving circuit that includes a transistor coupled to a terminal of the semiconductor diode, wherein the driving circuit is configured to receive a unipolar pulse and apply a bipolar electrical pulse to the semiconductor diode responsive to receiving the unipolar pulse; and
a pulse generator coupled to the driving circuit and configured to form the unipolar pulse and output the unipolar pulse to the driving circuit, wherein the pulse generator and driving circuit are configured to modulate the semiconductor diode with the bipolar electrical pulse at a repetition rate of between about 30 Hz and about 200 MHz.

67. The pulsed optical source of claim 66, wherein an optical pulse having a full-width-half maximum duration between 50 ps and 500 ps is emitted from the semiconductor diode responsive to application of the bipolar electrical pulse.

68. The pulsed optical source of claim 66, wherein the bipolar electrical pulse comprises a first pulse having a first magnitude and first polarity that is followed by a second pulse of opposite polarity having a second magnitude different from the first magnitude.

69. The pulsed optical source of claim 66, wherein the pulse generator comprises a first logic gate that forms the unipolar pulse from two differential clock signals.

70. The pulsed optical source of claim 66, wherein the pulse generator further comprises an adjustable delay element configured to vary a pulse length of the unipolar pulse in increments between 1 ps and 5 ps.

71. A pulsed optical source comprising:
a semiconductor diode configured to emit light;
a driving circuit that includes a transistor coupled to a terminal of the semiconductor diode, wherein the driving circuit is configured to receive a unipolar pulse and apply a bipolar electrical pulse to the semiconductor diode responsive to receiving the unipolar pulse;

a photodetector array having a plurality of pixels that are each configured to discriminate photon arrival times into at least two time bins during a single charge-accumulation interval; and an optical system arranged to form an image of an object, that is illuminated by the pulsed optical source, on the photodetector array.

72. The pulsed optical source of claim 71, wherein an optical pulse having a full-width-half maximum duration between 50 ps and 500 ps is emitted from the semiconductor diode responsive to application of the bipolar electrical pulse.

73. The pulsed optical source of claim 71, further comprising a pulse generator coupled to the driving circuit and configured to form the unipolar pulse and output the unipolar pulse to the driving circuit, wherein the pulse generator and driving circuit are configured to modulate the semiconductor diode with the bipolar electrical pulse at a repetition rate of between about 30 Hz and about 200 MHz.

74. The pulsed optical source of claim 73, wherein the pulse generator comprises a first logic gate that forms the unipolar pulse from two differential clock signals.

75. The pulsed optical source of claim 73, wherein the pulse generator further comprises an adjustable delay element configured to vary a pulse length of the unipolar pulse in increments between 1 ps and 5 ps.

* * * * *